United States Patent [19]

Takaya et al.

[11] Patent Number: 4,584,290
[45] Date of Patent: Apr. 22, 1986

[54] CEPHEM COMPOUNDS

[75] Inventors: Takao Takaya, Kawanishi; Takashi Masugi, Ikeda; Takashi Ogino, Kobe; Hisashi Takasugi, Hamagutinishi; Hideaki Yamanaka, Hirakata, all of Japan

[73] Assignee: Fujisawa Pharmaceutical Co., Ltd., Osaka, Japan

[21] Appl. No.: 556,413

[22] Filed: Nov. 30, 1983

[30] Foreign Application Priority Data

Dec. 6, 1982 [GB] United Kingdom ............. 8234755
Jan. 5, 1983 [GB] United Kingdom ............. 8300122
Jun. 28, 1983 [GB] United Kingdom ............. 8317496
Nov. 8, 1983 [GB] United Kingdom ............. 8329768

[51] Int. Cl.$^4$ ............... C07D 501/38; A61K 31/545
[52] U.S. Cl. ............................. 514/206; 544/25; 544/26; 544/27
[58] Field of Search ............... 544/25, 21, 27, 26; 424/246; 514/203, 204, 206

[56] References Cited

U.S. PATENT DOCUMENTS 4,415,562 11/1983 Farge et al. ............. 424/246

Primary Examiner—Nicholas S. Rizzo
Attorney, Agent, or Firm—Oblon, Fisher, Spivak, McClelland & Maier

[57] ABSTRACT

The invention relates to novel compounds of high antimicrobial activity of the formula:

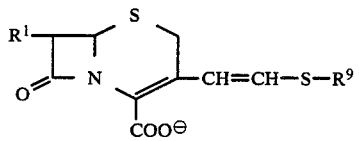

wherein
$R^1$ is amino or acylamino; and
$R^9$ is a group of the formula:

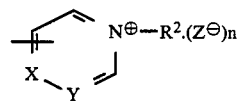

wherein
$R^2$ is organic group,
X is CH or N,
Z is acid residue
Y is CH or N and n is O; or
Y is N⊕—$R^2$ wherein $R^2$ is as defined above and n is 1, or a group of the formula:

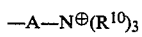

wherein
$R^{10}$ is lower alkyl and
A is lower alkylene.

6 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities, to processes for preparation thereof, to pharmaceutical composition comprising the same, and to a method of using the same therapeutically for the treatment of infectious diseases in human being and animals.

Accordingly, it is one object of the present invention to provide new cephem compounds and pharmaceutically acceptable salts thereof, which are highly active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I):

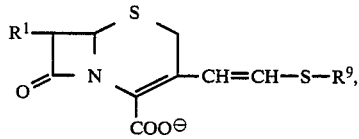

(I)

wherein
R$^1$ is amino or acylamino; and
R$^9$ is a group of the formula:

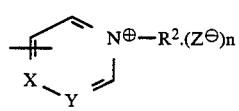

wherein
R$^2$ is organic group,
X is CH or N,
Z is acid residue
Y is CH or N and n is 0; or
Y is N$^⊕$-R$^2$ wherein R$^2$ is as defined above and n is 1, or a group of the formula:

wherein
R$^{10}$ is lower alkyl and
A is lower alkylene.

According to the present invention, the new cephem compounds (I) can be prepared by various processes which are illustrated in the following schemes.

Process 1

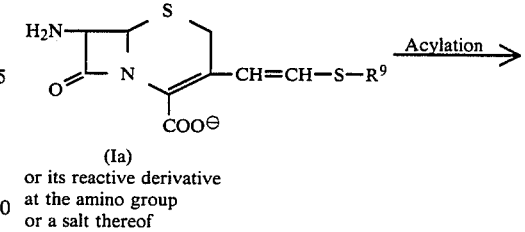

(Ia)
or its reactive derivative
at the amino group
or a salt thereof

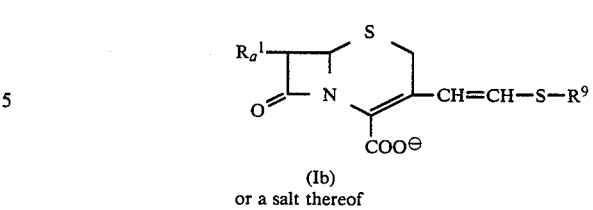

(Ib)
or a salt thereof

Process 2

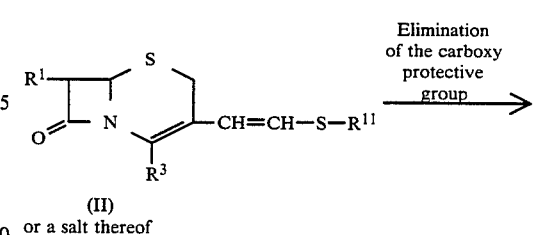

(II)
or a salt thereof

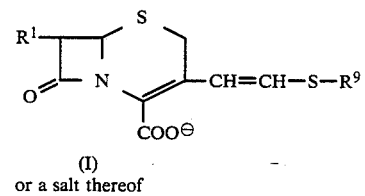

(I)
or a salt thereof

Process 3

R$^1$─[cephem]─CH=CH─S─R$^{12}$
    COOH (III)
or a salt thereof reaction preparing
quaternary
ammonium salt
──────────→

R$^1$─[cephem]─CH=CH─S─R$^9$
    COO$^⊖$ (I)
or a salt thereof

Process 4

R$_b^1$─[cephem]─CH=CH─S─R$^9$
    COO$^⊖$ (Ic)
or a salt thereof

Elimination
of amino
protective
group
──────────→

-continued

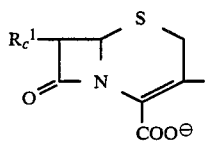

(Id) or a salt thereof

Process 5

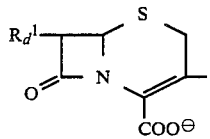

(Ie) or a salt thereof

Alkylation →

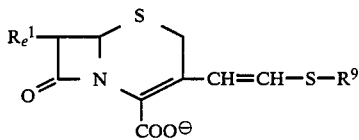

(If) or a salt thereof

Process 6

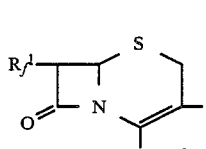

(Ig) or a salt thereof

Elimination of the carboxy protective group →

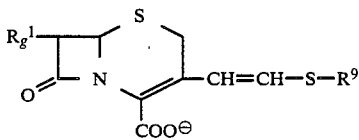

(Ih) or a salt thereof

Process 7

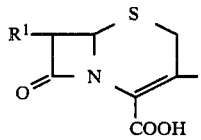

(VIII) or a salt thereof

+ HS—R$^{11}$ →

(XIVa) or a salt thereof

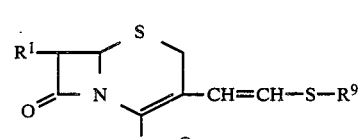

(I) or a salt thereof

Process 8

-continued

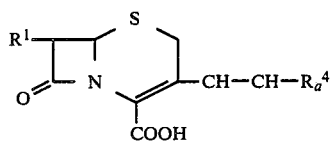

(VIc) or a salt thereof

+ HS—R$^{11}$ →

(XIVa) or a salt thereof

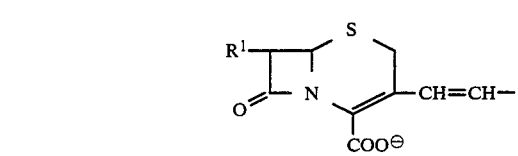

(I) or a salt thereof wherein
R$^1$ and R$^9$ are each as defined above;
R$_a^1$ is acylamino;
R$_b^1$ is acylamino having protected amino group;
R$_c^1$ is acylamino having amino group;
R$^3$ is a protected carboxy;
R$_a^4$ is a group which can be substituted with a group of the formula: —S—R$^9$ wherein R$^9$ is as defined above;
R$^{11}$ is a group of the formula:

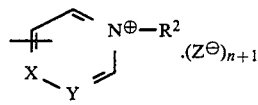

wherein R$^2$, X, Z, Y and n are each as defined above, or a group of the formula:

—A—N$^{\oplus}$(R$^{10}$)$_3$·Z$^{\ominus}$ wherein
A, R$^{10}$ and Z are each as defined above;
R$^{12}$ is a group of the formula:

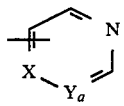

wherein
X is as defined above, and
Y$_a$ is CH or N,
or a group of the formula:

—A—N(R$^{10}$)$_2$ wherein
A and R$^{10}$ are each as defined above;
R$_d^1$ is acylamino having a pyridyl(lower)alkoxyimino group;
R$_e^1$ is acylamino having a lower alkyl pyridinio(lower)alkoxyimino group;
R$_f^1$ is acylamino having a protected carboxy(lower)alkoxyimino group, a protected carboxy(lower)alkenyloxyimino group or protected carboxycyclo(lower)alkoxyimino; and $R_g^1$ is acylamino having a carboxy(lower)alkoxyimino group, a carboxy(lower)alkenyloxyimino group or a carboxycyclo(lower)alkoxyimino group.

Among the starting compounds in the present invention, the compound (II) is novel and can be prepared by the processes which are illustrated in the following schemes.

Process A-(1)

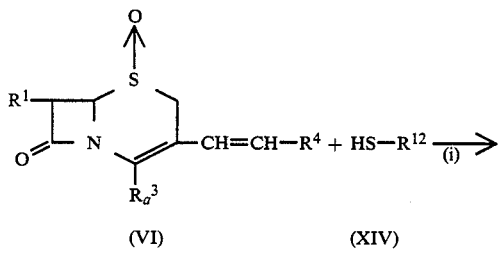

(VI)
or a salt thereof (XIV)
or a salt thereof

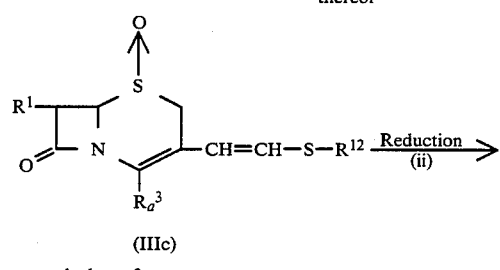

(IIIc)
or a salt thereof

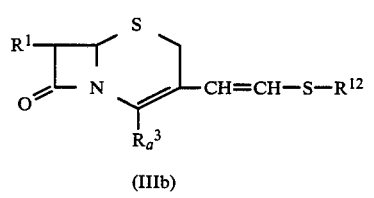

(IIIb)
or a salt thereof

Process A-(2)

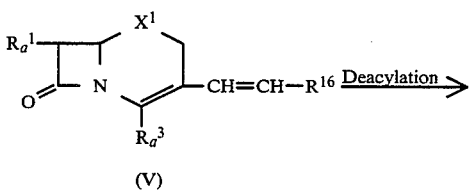

(V)
or a salt thereof

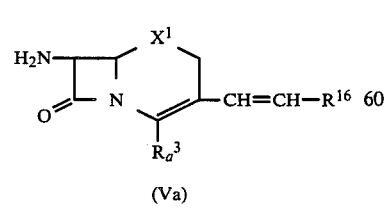

(Va)
or a salt thereof

Process A-(3)

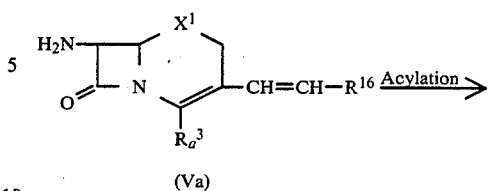

(Va)
or its reactive derivative
at the amino group
or a salt thereof

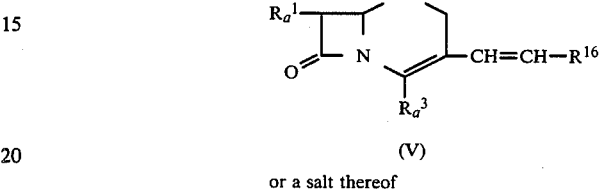

(V)
or a salt thereof

Process A-(4)

Elimination of the carboxy protective group (Vb)
or a salt thereof (Vc)
or a salt thereof Process B-(1)

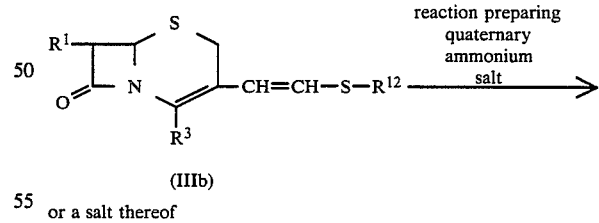

(IIIb)
or a salt thereof

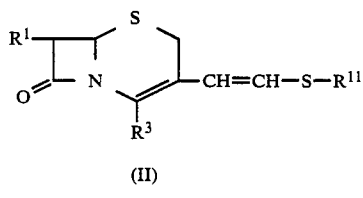

(II)
or a salt thereof

Process B-(2)

-continued

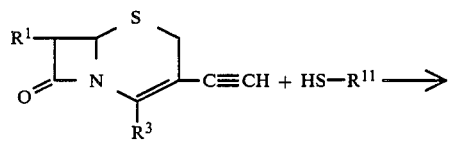

(VIIIa)
or a salt thereof (XIVa)
or a salt thereof

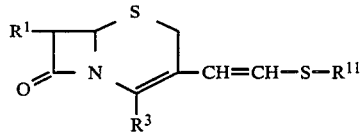

(II)
or a salt thereof

Process B-(3)

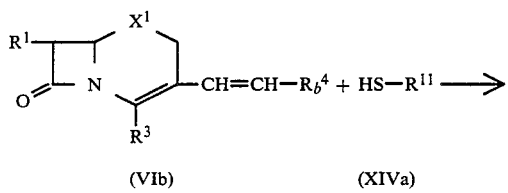

(VIb)
or a salt thereof (XIVa)
or a salt thereof

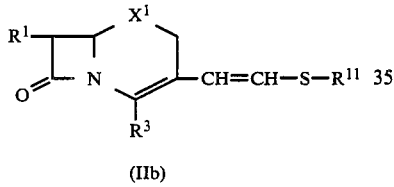

(IIb)
or a salt thereof

Process B-(4)

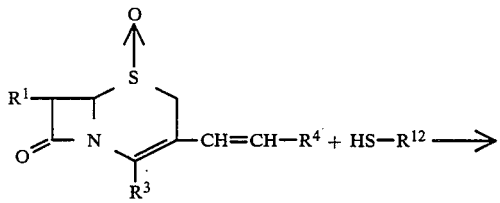

(VIa)
or a salt thereof (XIV)
or a salt thereof

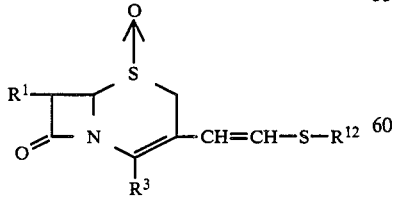

(IIId)
or a salt thereof

Process B-(5)

-continued

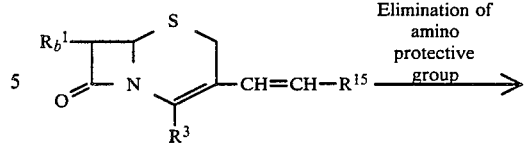

(IV)
or a salt thereof

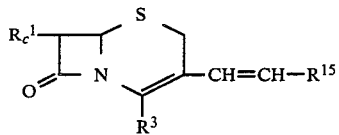

(IVa)
or a salt thereof

Process B-(6)

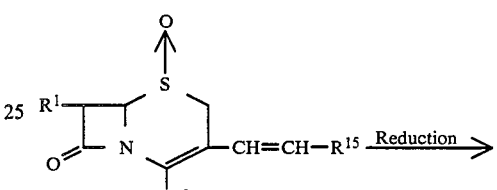

(IVb)
or a salt thereof

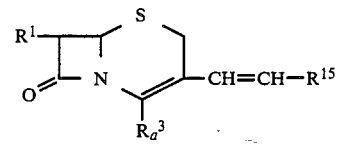

(IVc)
or a salt thereof

Process C-(1)

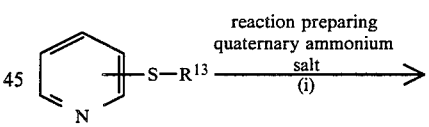

(IX)
or a salt thereof

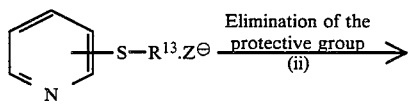

(X)
or a salt thereof

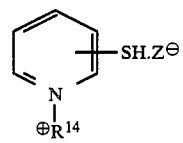

(XI)
or a salt thereof

Process C-(2)

-continued

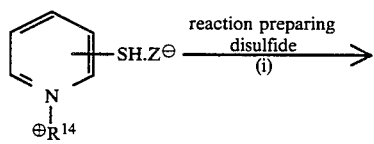

(XI)
or a salt thereof

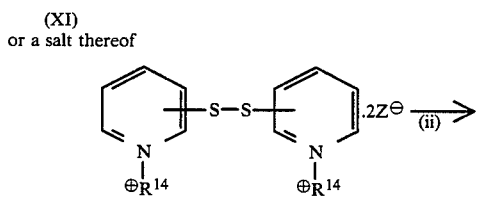

(XII)
or a salt thereof

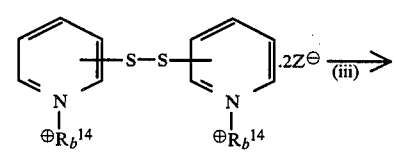

(XIIa)
or a salt thereof

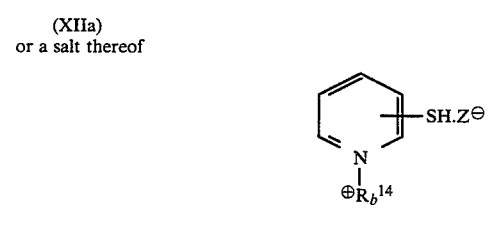

(XIa)
or a salt thereof

Process C-(3)

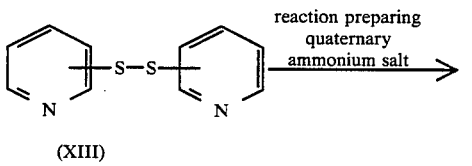

(XIII)
or a salt thereof

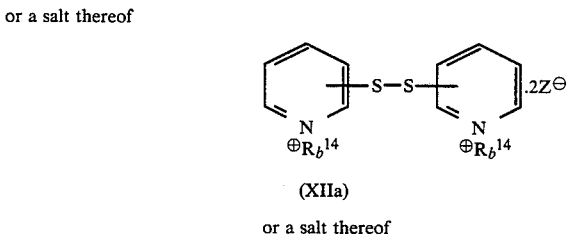

(XIIa)
or a salt thereof wherein
$R^1$, $R_a^1$, $R_b^1$, $R_c^1$, $R^3$, $R^{11}$, $R^{12}$ and Z are each as defined above;
$R_a^3$ is carboxy or a protected carboxy;
$R^{13}$ is a mercapto protective group;
$R^{14}$ is amino(lower)alkyl;
$R_a^{14}$ is protected amino(lower)alkyl;
$R_b^{14}$ is N,N-di(lower)alkylamino(lower)alkyl;
$R^4$ is a group which can be substituted with a group of the formula: $-S-R^{12}$ wherein $R^{12}$ is as defined above;
$R_b^4$ is a group which can be substituted with a group of the formula: $-S-R^{11}$ wherein $R^{11}$ is as defined above;
$X^1$ is $-S-$ or

$R^{15}$ is a group of the formula: $-R^4$ and $-S-R^{11}$ wherein $R^4$ and $R^{11}$ are each as defined above; and
$R^{16}$ is a group of the formula: $-R^4$ and $S-R^{12}$ wherein $R^4$ and $R^{12}$ are each as defined above.

Regarding the object compounds(I), (Ib), (Ic), (Id), (Ie), (If), (Ig) and (Ih) and the starting compounds(II), (IIa), (IIb), (III), (IIIa), (IIIb), (IIIc), (IIId), (IV), (IVa), (IVb), (IVc), (V), (Va), (Vb), (Vc), (VI), (VIa), (VIb), and (VIc), it is to be understood that said object and starting compounds include cis isomer, trans isomer and a mixture thereof. For example, with regard to the object compound (I), cis isomer means one geometrical isomer having the partial structure represented by the following formula:

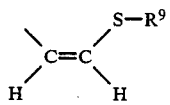

(wherein $R^9$ is as defined above) and trans isomer means the other geometrical isomer having the partial structure represented by the following formula:

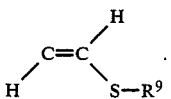

(wherein $R^9$ is as defined above).

Suitable pharmaceutically acceptable salts of the object compounds (I) are conventional non-toxic salts and include an organic acid salt (e.g. acetate, maleate, tartrate, methanesulfonate, benzenesulfonate, formate, toluenesulfonate, trifluoroacetate, etc.), an inorganic acid salt (e.g. hydrochloride, hydrobromide, hydriodide, sulfate, phosphate, etc.), a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

The term "higher" is intended to mean 7 to 20 carbon atom(s), unless otherwise indicated.

Suitable "acyl" and "acyl moiety" in the term "acyl-amino" as mentioned above may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Aliphatic acyl such as lower or higher alkanoyl (e.g. formyl, acetyl, succinyl, hexanoyl, heptanoyl, stearoyl, etc.);

lower or higher alkoxycarbonyl (e.g. methoxycarbonyl, ethoxycarbonyl, t-butoxycarbonyl, t-pentyloxycarbonyl, heptyloxycarbonyl, etc.);

lower or higher alkanesulfonyl (e.g. methanesulfonyl, ethanesulfonyl, etc.); or the like;
Aromatic acyl such as
aroyl (e.g. benzoyl, toluoyl, naphthoyl, etc.);
ar(lower)alkanoyl such as phenyl(lower)alkanoyl (e.g. phenylacetyl, phenylpropionyl, etc.);
aryloxycarbonyl (e.g. phenoxycarbonyl, naphthyloxycarbonyl, etc.);
aryloxy(lower)alkanoyl (e.g. phenoxyacetyl, phenoxypropionyl, etc.);
arylglyoxyloyl (e.g. phenylglyoxyloyl, naphthylglyoxyloyl, etc.);
arenesulfonyl (e.g. benzenesulfonyl, p-toluenesulfonyl, etc.); or the like;
Heterocyclic acyl such as
heterocycliccarbonyl (e.g. thenoyl, furoyl, nicotinoyl, etc.);
heterocyclic(lower)alkanoyl (e.g. thienylacetyl, thiazolylacetyl, thiadiazolylacetyl, tetrazolylacetyl, etc.);
heterocyclicthio(lower)alkanoyl (e.g. thienylthioacetyl, thiazolylthioacetyl, isothiazolylthioacetyl, thiadiazolylthioacetyl, tetrazolylthioacetyl, etc.);
heterocyclicglyoxyloyl (e.g. thiazolylglyoxyloyl, thienylglyoxyloyl, etc.); or the like; in which suitable heterocyclic moiety in the term "heterocycliccarbonyl", "heterocyclic(lower)alkanoyl", "heterocyclicthio(lower)alkanoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as
unsaturated 3 to 8-membered more preferably 5 or 6-membered heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;
saturated 3 to 8-membered (more preferably 5 or 6-membered)heteromonocyclic group containing 1 to 4 nitrogen atom(s), for example, pyrrolidinyl, imidazolidinyl, piperidino, piperazinyl, etc.;
unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;
unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.;
saturated 3 to 8-membered (more preferably 5 or 6-membered)heteromonocyclic group containing 1 to 2 oxygen atom(s) and 1 to 3 nitrogen atom(s), for example, morpholinyl, sydnonyl, etc.;
unsaturated condensed heterocyclic group containing 1 to 2 oxygen atom(s) and 1 to 3 nitrogen atom(s), for example, benzoxazolyl, benzoxadiazolyl, etc.; unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;
saturated 3 to 8-membered (more preferably 5 or 6-membered) heteromonocyclic group containing 1 to 2 sulfur atom(s) and 1 to 3 nitrogen atom(s), for example, thiazolidinyl, etc.;
unsaturated 3 to 8-membered (more preferably 5 or 6-membered) heteromonocyclic group containing 1 to 2 sulfur atom(s), for example, thienyl, dihydrodithiinyl, dihydrodithionyl, etc.;
unsaturated condensed heterocyclic group containing 1 to 2 sulfur atom(s) and 1 to 3 nitrogen atom(s), for example, benzothiazolyl, benzothiadiazolyl, etc.; unsaturated 3 to 8-membered (more preferably 5 to 6-membered) heteromonocyclic group containing an oxygen atom, for example, furyl, etc.;
unsaturated 3 to 8-membered (more preferably 5 or 6-membered) heteromonocyclic group containing an oxygen atom and 1 to 2 sulfur atom(s), for example, dihydrooxathiinyl, etc.;
unsaturated condensed heterocyclic group containing 1 to 2 sulfur atom(s), for example, benzothienyl, benzodithiinyl, etc.; unsaturated condensed heterocyclic group containing an oxygen atom and 1 to 2 sulfur atom(s), for example, benzoxathiinyl, etc. and the like.

As to the heterocyclic group as mentioned above, the following points are to be noted. That is, in case that the heterocyclic group is specifically thiazolyl or thiadiazolyl group having amino or protected amino as a substituent in its molecule, said thiazolyl or thiadiazolyl group include tautomeric isomers, which are caused by the specific behavior of the thiazole or thiadiazole ring. That is, for example, said amino- or protected aminothiazolyl or thiadiazolyl group is represented by the formula:

(A)

(wherein $R^6$ is amino or protected amino and Ya is CH or N), and in case that the group of the formula (A) takes the formula:

(A')

(wherein $R^6$ and Ya are each as defined above), said group of the formula
(A') can also be alternatively represented by its tautomeric formula:

(A")

(wherein Ya is as defined above and $R^{6'}$ is imino or protected imino).

That is, both of the said groups of the formulae (A') and (A") are in the state of tautomeric equilibrium which can be represented by the following equilibrium:

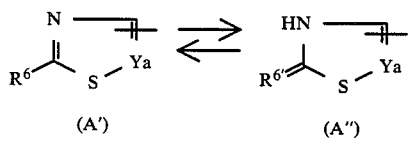

(wherein $R^6$, Ya and $R^{6'}$ are each as defined above).

These types of tautomerism between 2-aminothiazole or thiadiazole compounds and 2-iminothiazoline or thiadiazoline compounds as stated above have been well known in the arts, and it is obvious to a person skilled in arts that both of the tautomeric isomers are equilibrated and lie in the reciprocally convertible state, and accordingly it is to be understood that such isomers are included within the same category of the compound per se. Accordingly, the both of the tautomeric forms are clearly included within the scope of the present invention. In the present specification, the object and starting compounds including the group of such tautomeric isomers are represented by using one of the expressions therefor, i.e. 2-amino(or protected amino)thiazolyl or thiadiazolyl and the formula:

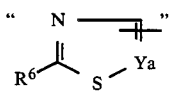

only for the convenient sake.

The acyl moiety as stated above may have one to ten, same or different, suitable substituent(s) such as lower alkyl (e.g. methyl, ethyl, etc.);

lower alkoxy (e.g. methoxy, ethoxy, propoxy, etc.);

lower alkylthio (e.g. methylthio, ethylthio, etc.);

lower alkylamino (e.g. methylamino, etc.); cyclo(lower-)alkyl (e.g. cyclopentyl, cyclohexyl, etc.);

cyclo(lower)alkeny (e.g. cyclohexenyl; cyclohexadienyl, etc.); halogen; amino; protected amino; hydroxy; protected hydroxy; cyano; nitro; carboxy; protected carboxy; sulfo; sulfamoyl; imino; oxo;

amino(lower)alkyl (e.g. aminomethyl, aminoethyl, etc.); carbamoyloxy;

a group of the formula: $=N-OR^7$ wherein $R^7$ is hydogen, lower alkyl (e.g. methyl, ethyl, propyl, etc.), lower alkenyl (e.g. vinyl, allyl, 2-butenyl, etc.), lower alkynyl (e.g. ethynyl, 2-propynyl, etc.), cyclo(lower-)alkyl (e.g. cyclopropyl, cyclohexyl, etc.), ar(lower-)alkyl such as phenyl(lower)alkyl (e.g. benzyl, phenethyl, etc.), carboxy(lower)alkyl (e.g. carboxymethyl, 1-carboxyethyl, carboxypropyl, carboxybutyl, etc.), protected carboxy(lower)alkyl, hydroxy(lower)alkyl (e.g. hydroxymethyl, hydroxyethyl, etc.), carboxy(lower)alkenyl (e.g. carboxyvinyl, carboxyallyl, carboxy-2-butenyl, etc.), protected carboxy(lower)alkenyl, pyridyl(lower)alkyl (e.g. (2-pyridyl)methyl, (3-pyridyl)methyl, etc.), and lower alkyl pyridinio(lower)alkyl (e.g. (1-methyl-2-pyridinio)methyl, (1-methyl-3-pyridinio)methyl, etc.), or the like.

In this connection, when the acyl moiety has a group of the formula: $=N-OR^7$, wherein $R^7$ is as defined above, as substituent(s), there are geometrical isomers (syn and anti isomers) due to the presence of double bond. And, for example, the syn isomer means one geometrical isomer having the group of the formula:

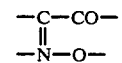

and the corresponding anti isomer means the other geometrical isomer having the group of the formula:

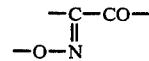

Suitable "protected amino" may include acylamino wherein "acyl" moiety can be referred to the ones as mentioned above, phosphonoamino, protected phosphonoamino, ar(lower)alkylamino such as benzylamino, phenethylamino, tritylamino; and the like.

Suitable "protected phosphono" may include esterified phosphono in which said ester may be the ones such as lower alkyl ester (e.g. methyl ester, ethyl ester, propyl ester, isopropyl ester, butyl ester, isobutyl ester, t-butyl ester, pentyl ester, t-pentyl ester, hexyl ester, etc.) or the like.

Suitable "protected hydroxy" may include acyloxy wherein "acyl" moiety can be referred to the ones as mentioned above.

Suitable "protected carboxy" and "protected carboxy moiety" in the terms "protected carboxy(lower-)alkyl" and "protected carboxy(lower)alkenyl" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.] lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl-2-oxo-1,3-dioxol-4-yl(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.];

lower alkenyl ester (e.g. vinyl ester, allyl ester, etc.);

lower alkynyl ester (e.g. ethynyl ester, propynyl ester, etc.);

ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.);

aryl ester which may have at least one suitable substituent(s) (e.g. phenyl ester, 4-chlorophenyl ester, tolyl ester, tert-butylphenyl ester, xylyl ester, mesityl ester, cumenyl ester, etc.);

phthalidyl ester; and the like.

Preferable examples of the esterified carboxy as mentioned above may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.), and phenyl(lower)alkoxycarbonyl (e.g. benzyloxycarbonyl, benzhydryloxycarbonyl, etc.) which may have a nitro group.

Suitable "organic group" may include lower alkyl which may have suitable substituent(s).

Suitable "lower alkyl" may include straight or branched one, having 1 to 6 carbon atom(s), such as methyl, ethyl, propyl, isopropyl, butyl, t-butyl, pentyl, hexyl or the like.

The aforesaid "lower alkyl" may have 1 to 3 suitable substituent(s) such as amino, hydroxy, di(lower)alkylamino (e.g. dimethylamino, diethylamino, etc.), morpholino, piperazinyl substituted with lower alkyl (e.g. methylpiperazinyl, etc.), piperazinylcarbonyl substituted with lower alkyl (e.g. methylpiperazinylcarbonyl, etc.), formimidoylamino, or the like.

Suitable "mercapto protective group" may include aromatic acyl such as aroyl (e.g. benzoyl, toluoyl, etc.) and the like.

Suitable "amino(lower)alkyl" may include aminomethyl, aminoethyl, aminopropyl, and the like.

Suitable "protected amino(lower)alkyl" may include phthalimidoethyl, phthalimidopropyl, and the like.

Suitable "N,N-di(lower)alkylamino(lower)alkyl" may include N,N-dimethylaminoethyl, N,N-dimethylaminopropyl, and the like.

Suitable "halogen" may include chlorine, bromine, fluorine and iodine.

Suitable "acid residue" may include acyloxy, azido, halogen and the like, wherein acyl moiety in the term "acyloxy" and halogen can be referred to the ones as exemplified above.

Suitable "lower alkylene" may include straight or branched one, having 1 to 6 carbon atom(s), such as methylene, ethylene, trimethylene, propylene, butylene, or the like.

Suitable $R^4$, $R_a^4$ and $R_b^4$ may include aforesaid acid residue, etc.

Suitable "carboxy(lower)alkyl", "pyridyl(lower)alkoxyimino", "lower alkyl pyridinio(lower)alkoxyimino", "protected carboxy(lower)alkoxyimino", "protected carboxy(lower)alkenyloxyimino", "carboxy(lower)alkoxyimino" and "carboxy(lower)alkenyloxyimino" can be referred to the ones as mentioned above.

Preferred embodiments of the object compounds (I) are as follows.

Preferred embodiment of $R^1$ is amino;

aminothiazolyl(lower)alkanoylamino having a lower alkoxyimino group;

aminothiazolyl(lower)alkanoylamino having a lower alkenyloxyimino group;

aminothiazolyl(lower)alkanoylamino having a lower alkynyloxyimino group;

aminothiazolyl(lower)alkanoylamino having a carboxy(lower)alkoxyimino group;

aminothiazolyl(lower)alkanoylamino having a protected carboxy(lower)alkoxyimino group, more preferably lower alkoxycarbonyl(lower)alkoxyimino-2-aminothiazolylacetamido and ar(lower)alkoxycarbonyl(lower)alkoxyimino-2-aminothiazolylacetamido;

aminothiazolyl(lower)alkanoylamino having a hydroxy(lower)alkoxyimino group;

aminothiazolyl(lower)alkanoylamino having a carboxy(lower)alkenyloxyimino group;

aminothiazolyl(lower)alkanoylamino having a protected carboxy(lower)alkenyloxyimino group, more preferably aminothiazolyl(lower)alkanoylamino having an ar(lower)alkoxycarbonyl(lower)alkenyloxyimino group;

aminothiazolyl(lower)alkanoylamino having a pyridyl(lower)alkoxyimino group;

aminothiazolyl(lower)alkanoylamino having a 1-(lower alkyl)pyridinio(lower)alkoxyimino group;

protected aminothiazolyl(lower)alkanoylamino having a lower alkoxyimino group, preferably acylaminothiazolyl(lower)alkanoylamino having a lower alkoxyimino group, or ar(lower)alkylaminothiazolyl(lower)alkanoylamino having a lower alkoxyimino group;

protected aminothiazolyl(lower)alkanoylamino having a lower alkynyloxyimino group, preferably ar(lower)alkylaminothiazolyl(lower)alkanoylamino having a lower alkynyloxyimino group;

protected aminothiazolyl(lower)alkanoylamino having a protected carboxy(lower)alkoxyimino group, preferably acylaminothiazolyl(lower)alkanoylamino having a lower alkoxycarbonyl(lower)alkoxyimino group, or ar(lower)alkylaminothiazolyl(lower)alkanoylamino having an ar(lower)alkoxycarbonyl(lower)alkoxyimino group;

protected aminothiazolyl(lower)alkanoylamino having a protected carboxy(lower)alkenyloxyimino group, preferably ar(lower)alkylaminothiazolyl(lower)alkanoylamino having an ar(lower)alkoxycarbonyl(lower)alkenyloxyimino group;

protected aminothiazolyl(lower)alkanoylamino having a pyridyl(lower)alkoxyimino group, preferably lower alkanoylaminothiazolyl(lower)alkanoylamino having a pyridyl(lower)alkoxyimino group;

aminothiadiazolyl(lower)alkanoylamino having a lower alkoxyimino group;

aminothiadiazolyl(lower)alkanoylamino having a lower alkenyloxyimino group;

aminothiadiazolyl(lower)alkanoylamino having a lower alkynyloxyimino group;

aminothiadiazolyl(lower)alkanoylamino having a hydroxy(lower)alkoxyimino group;

aminothiadiazolyl(lower)alkanoylamino having a carboxy(lower)alkoxyimino group;

protected aminothiadiazolyl(lower)alkanoylamino having a lower alkoxyimino group, more preferably phosphonoaminothiadiazolyl(lower)alkanoylamino having a lower alkoxyimino group;

thiazolyl(lower)alkanoylamino having a carboxy(lower)alkoxyimino group;

thiadiazolyl(lower)alkanoylamino having a lower alkoxyimino group;

isothiazolylthio(lower)alkanoylamino substituted with hydrogen and carboxy;

aminothiazolyl hydroxy substituted (lower)alkanoylamino group;
dihydrooxathiinyl(lower)alkanoylamino having a lower alkoxyimino group;
hydroxy ar(lower)alkanoylamino having a lower alkoxyimino group;
aminopyrimidinyl(lower)alkanoylamino having a lower alkenyloxyimino group;
aminopyridyl(lower)alkanoylamino having a lower alkoxyimino group;
protected aminopyridyl(lower)alkanoylamino having a lower alkoxyimino group, preferably lower alkanoylaminopyridyl(lower)alkanoylamino having a lower alkoxyimino group;
aminothiazolyl(lower)alkanoylamino having a carboxycyclo(lower)alkoxyimino group;
protected aminothiazolyl(lower)alkanoylamino having a protected carboxycyclo(lower)alkoxyimino group, preferably ar(lower)alkylaminothiazolyl(lower)alkanoylamino having a lower alkoxycarbonylcyclo(lower)alkoxyimino group; and
$R^9$ is a group of the formula:

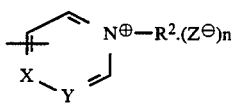

wherein
$R^2$ is lower alkyl, amino(lower)alkyl, hydroxy(lower)alkyl, carboxy(lower)alkyl, di(lower)alkylamino(lower)alkyl, morpholino(lower)alkyl, lower alkylpiperazinyl(lower)alkyl, lower alkylpiperazinylcarbonyl(lower)alkyl or formimidoylamino(lower)alkyl;
X is CH or N;
Z is halogen; and
Y is CH or N and n is 0; or
Y is $N^\oplus$—$R^2$ and n is 1, or a group of the formula:

wherein $R^{10}$ is lower alkyl and A is lower alkylene.

The processes for preparing the object compounds of the present invention are explained in detail in the following.

Process 1

The object compound (Ib) or a salt thereof can be prepared by subjecting the compound (Ia) or its reactive derivative at the amino group or a salt thereof to acylation reaction.

Suitable reactive derivative at the amino group of the compound (Ia) may include Schiff's base type imino or its tautomeric enamine type isomer formed by the reaction of the compound (Ia) with a carbonyl compound such as aldehyde, ketone or the like; a silyl derivative formed by the reaction of the compound (Ia) with a silyl compound such as bis(trimethylsilyl)acetamide, mono(trimethylsilyl)acetamide or the like; a derivative formed by reaction of the compound (Ia) with phosphorus trichloride or phosgene, and the like.

Suitable acylating agent to be used in the present acylation reaction may include conventional one and can be shown by the formula: $R^5$—OH (VII) (wherein $R^5$ is acyl) or its reactive derivative or a salt thereof.

Suitable salt of the compounds (Ia) and (VII) may include an acid addition salt such as an organic acid salt (e.g. acetate, maleate, tartrate, methanesulfonate, benzenesulfonate, toluenesulfonate, etc.) or an inorganic acid salt (e.g. hydrochloride, hydrobromide, sulfate, phosphate, etc.); a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative of the compound (VII) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid etc.), dialkylphosphorous acid, sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hyroxysuccinimide, N-hydroxyphthalimide, 1-hydroxy-6-chloro-1H-benzotriazole, etc.), and the like. These reactive derivatives can optionally be selected from them according to the kind of the compound (VII) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

When the compound (VII) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower-)alkylmorphorine, N,N-di(lower)alkylbenzylamine, or the like. The reaction temperature is not critical, and the reaction is usually carried out under cooling or at ambient temperature.

In the present reaction, a syn isomer of the object compound (Ib) can be obtained preferably by conducting the present reaction of the compound (Ia) with the corresponding syn isomer of the starting compound (VII).

Process 2

The object compound (I) or a salt thereof can be prepared by subjecting the compound (II) or a salt thereof to elimination reaction of the carboxy protective group.

Suitable salt of the compound (II) can be referred to the salt exemplified for the compound (I).

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid. Suitable base may include conventional inorganic base and an organic base.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitably be selected in accordance with the kind of the carboxy protective group and the elimination method.

The elimination using Lewis acid is preferable to eliminate substituted or unsubstituted ar(lower)alkyl ester and carried out by reacting the compound (II) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof.

The reductive elimination can be applied preferably for elimination of the protective group such as halo(lower)alkyl (e.g. 2-iodoethyl, 2,2,2-trichloroethyl, etc.) ester, ar(lower)alkyl (e.g. benzyl, etc.) ester or the like. The reduction method applicable for the elimination reaction may include, for example, reduction by using a combination of a metal (e.g. zinc, zinc amalgam, etc.) or a salt of chromium compound (e.g. chromous chloride, chromous acetate, etc.) and an organic or an inorganic acid (e.g. acetic acid, propionic acid, hydrochloric acid, etc.); and conventional catalytic reduction in the presence of a conventional metallic catalyst (e.g. palladium carbon, Raney nickel, etc.).

The reaction temperature is not critical, and the reaction is usually carried out under cooling, at ambient temperature or under warming.

The present elimination reaction of the carboxy protective group includes, within its scope, the cases that another protected carboxy, acylamino and/or protected amino group(s) are converted into the corresponding free carboxy and/or amino group(s) during the reaction or the post-treating step of the present process.

Process 3

The object compound (I) or a salt thereof can be prepared by subjecting the compound (III) or a salt thereof to reaction preparing quaternary ammonium salt.

Suitable salt of the compound (III) can be referred to the ones as exemplified for the compound (I).

The agent to be used in the present reaction preparing quaternary ammonium salt may include conventional one such as mono (or di) lower alkyl sulfate (e.g. dimethyl sulfate, etc.), lower alkyl lower alkanesulfonate (e.g. methyl methanesulfonate, etc.), halo(lower)alkane (e.g. bromomethane, iodomethane, iodoethane, etc.), protected carboxy(lower)alkyl halide (e.g. benzhydryl bromoacetate, etc.), amino(lower)alkyl halide (e.g. aminoethyl bromide, aminoethyl iodide, aminopropyl bromide, aminopropyl iodide, etc.), hydroxy(lower)alkyl halide (e.g. 2-hydroxyethyl bromide, 2-hydroxyethyl iodide, etc.), di(lower)alkylamino(lower)alkyl halide (e.g. 2-N,N-dimethylaminoethyl bromide, 2-N,N-dimethylaminoethyl iodide, 3-N,N-dimethylaminopropyl bromide, 3-N,N-dimethylaminopropyl iodide, etc.), morpholino(lower)alkyl halide (e.g. 2-morpholinoethyl bromide, 2-morpholinoethyl iodide, etc.), lower alkyl-piperazinyl(lower)alkyl halide (e.g. 3-(4-methyl-1-piperazinyl)propyl bromide, 3-(4-methyl-1-piperazinyl)propyl iodide, etc.), lower alkylpiperazinyl-carbonyl(lower)alkyl halide (e.g. 1-methyl-4-piperazinylcarbonylmethyl bromide, 1-methyl-4-piperazinylcarbonylmethyl iodide, etc.), (2,2-dimethyl-1,3-dioxolan-4-yl)methyl trifluoromethanesulfonate, or the like.

When lower alkyl ester of an acid is used as an agent, the reaction is usually carried out in a solvent such as water, acetone, tetrahydrofuran, ethanol, ether, dimethylformamide or any other solvent which does not adversely influence the reaction.

The present reaction is preferably carried out in the presence of a conventional base such as an inorganic base or an organic base.

The reaction temperature is not critical and the reaction is usually carried out under cooling to heating around boiling point of the solvent.

Process 4

The object compound (Id) or a salt thereof can be prepared by subjecting the compound (Ic) or a salt thereof to elimination reaction of amino protective group.

Suitable salt of the compound (Ic) can be referred to the salt, exemplified for the compound (I).

The elimination reaction is carried out in accordance with a conventional method such as hydrolysis; reduction; a method treating the compound (Ic) wherein protected amino moiety is acylamino with iminohalogenating agent, iminoetherifying agent and then, if necessary, hydrolysing the resultant; or the like. The hydrolysis may include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, for example, tertpentyloxycarbonyl, lower alkanoyl (e.g. formyl, acetyl, etc.), cycloalkoxycarbonyl, substituted or unsubstituted aralkoxycarbonyl, aralkyl (e.g. trityl), substituted phenylthio, substituted aralkylidene, substituted alkylidene, substituted cycloalkylidene or the like. Suitable acid includes an organic or inorganic acid such as formic acid, trifluoroacetic acid, benzenesulfonic acid, p-toluenesulfonic acid, hydrochloric acid and the like, and the most suitable acid is an acid which can easily be removed from the reaction mixture by a conventional manner such as distillation under reduced pressure, for example, formic acid, trifluoroacetic acid, hydrochloric acid, etc. The acids can be selected according to the kind of the protective group to be eliminated. When the elimination reaction is conducted with an acid, it can be carried out in the presence or absence of a solvent. Suitable solvent includes water, a conventional organic solvent or a mixture thereof.

The elimination reaction using trifluoroacetic acid may be carried out in the presence of anisole. The hydrolysis using hydrazine is commonly applied for eliminating a phthaloyl, succinyl type aminoprotective group.

The elimination using base is used for eliminating an acyl group such as trifluoroacetyl. Suitable base may include an inorganic base and an organic base.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, etc.), 2-pyridylmethoxycarbonyl, etc. Suitable reduction may include, for example, reduction with an alkali metal borohydride (e.g. sodium borohydride, etc.), reduction with a combination of a metal (e.g. tin, zinc, iron, etc.) or the said metal together with a metal salt compound (e.g. chromous chloride, chromous acetate, etc.) and an organic or inorganic acid (e.g. acetic acid, propionic acid, hydrochloric acid, etc.); and catalytic reduction. Suitable catalyst includes a conventional one, for example, Raney nickel, platinum oxide, palladium carbon and the like.

Among the protective groups, the acyl group can generally be eliminated by hydrolysis. Especially, halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g. phosphorus oxychloride, etc.) and an iminoetherifying agent such as lower alkanol (e.g. methanol, ethanol, etc.), if necessary, followed by hydrolysis.

The reaction temperature is not critical and may suitably be selected in accordance with the kind of the amino protective group and the elimination method as mentioned above, and the reaction is preferably carried out under a mild condition such as under cooling or at slightly elevated temperature.

The present invention includes, within its scope, the cases that another protected amino, protected hydroxy and/or protected carboxy group(s) are converted into the corresponding free amino, the free hydroxy and/or the free carboxy group(s) during the reaction or the post-treating step of the present process.

Process 5

The object compound (If) or a salt thereof can be prepared by reacting the compound (Ie) or a salt thereof with a lower alkylating agent.

Suitable salt of the compound (Ie) can be referred to the ones as exemplified for the compound (I).

The lower alkylating agent to be used in the present alkylation reaction may include conventional one such as mono (or di) lower alkyl sulfate (e.g. dimethyl sulfate, etc.), lower alkyl(lower)alkenesulfonate (e.g. methyl methanesulfonate, etc.), halo(lower)alkane (e.g. bromomethane, iodomethane, iodoethane, etc.), or the like.

When lower alkyl ester of an acid is used as a lower alkylating agent, the reaction is usually carried out in a solvent such as water, acetone, tetrahydrofuran, ethanol, ether, dimethylformamide or any other solvent which does not adversely influence the reaction.

The present reaction is preferably carried out in the presence of a conventional base such as an inorganic base or an organic base.

The reaction temperature is not critical and the reaction is usually carried out under cooling to heating around boiling point of the solvent.

Process 6

The compound (Ih) or a salt thereof can be prepared by subjecting the compound (Ig) or a salt thereof to elimination reaction of the carboxy protective group.

The present reaction can be carried out in a similar manner to that of aforementioned Process 2.

The present elimination reaction of the carboxy protective group includes, within its scope, the cases that acylamino and/or protected amino group(s) are converted into that corresponding amino group during the reaction or the post-treating step of the present process.

Process 7

The object compound (I) or a salt thereof can be prepared by reacting the compound (VIII) or a salt thereof with the compound (XIVa) or a salt thereof.

Suitable salt of the compound (VIII) can be referred to the ones exemplified for the compound (I).

The present reaction can be carried out in a similar manner to that of Process A-(1)-(i) as mentioned below.

Process 8

The object compound (I) or a salt thereof can be prepared by reacting the compound (VIc) or a salt thereof with the compound (XIVa) or a salt thereof.

Suitable salt of the compound (VIc) can be referred to the ones exemplified for the compound (I).

The present reaction can be carried out in a similar manner to that of Process A-(1)-(i) as mentioned below.

The present reaction includes, within its scope, the case that the resultant amino(lower)alkyl group for $R^2$ is converted into formimidoylamino(lower)alkyl group, by a conventional manner.

The present invention includes, within its scope, the cases that the one type of tautomeric isomer is converted into the other type of isomer during the reaction and/or the post-treating step of the each process.

The object compound (I) may be transformed into its pharmaceutically acceptable salt as aforementioned by a conventional method.

The processes for preparing the starting compounds of the present invention are explained in detail in the following.

Process A-(1)

(i): (VI)+(XIV)→(IIIc)

The object compound (IIIc) or a salt thereof can be prepared by reacting the compound (VI) or a salt thereof with the compound (XIV) or a salt thereof.

Suitable salt of the compound (VI) can be referred to the ones exemplified for the compound (I).

Suitable salt of the compound (XIV) may include an alkali metal salt (e.g. sodium salt, potassium salt, etc.).

The present reaction may be carried out in a solvent such as water, phosphate buffer, acetone, chloroform, acetonitrile, nitrobenzene, methylene chloride, ethylene chloride, formamide, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (VI) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under heating. The present reaction is preferably carried out in the presence of alkali metal halide (e.g. sodium iodide, potassium iodide, etc.), alkali metal thiocyanate (e.g. sodium thiocyanate, potassium thiocyanate, etc.) etc.

(ii): (IIIc)→(IIIb)

The compound (IIIb) or a salt thereof can be prepared by reducing the compound (IIIc) or a salt thereof.

The present reduction can be carried out by a conventional method which is applied for the transformation of

into —S—, for example, by using phosphorus trichloride, a combination of stannous chloride and acetyl chloride, a combination of an alkali metal iodide (e.g. sodium iodide, etc.) and trihaloacetic anhydride (e.g. trifluoroacetic anhydride, etc.), and the like.

The present reduction is usually carried out in a solvent such as acetone, dioxane, acetonitrile, dimethylformamide benzene, hexane, chloroform, methylene chloride, ethylene chloride, tetrahydrofuran, ethyl acetate, or any other solvent which does not adversely affect the reaction.

The reaction temperature is not critical and the reaction is usually carried out under cooling or at ambient temperature.

Process A-(2)

(V)→(Va)

The compound (Va) or a salt thereof can be prepared by subjecting the compound (V) or a salt thereof to deacylation reaction.

The present deacylation reaction is carried out in accordance with a conventional method such as hydrolysis; reduction; deacylation using Lewis acid; deacylation method by reacting the compound (V) with iminohalogenating agent and then with iminoetherifying agent, and, if necessary, subjecting the resulting compound to hydrolysis; or the like.

Among these methods, "the deacylation method by reacting the compound (V) with iminohalogenating agent and then with iminoetherifying agent, and, if necessary, subjecting the resulting compound to hydrolysis" is preferable method.

Suitable iminohalogenating agent may include phosphorus halide (e.g. phosphorus trichloride, phosphorus pentachloride, phosphorus tribromide, phosphorus pentabromide, etc.), phosphorus oxychloride, thionyl chloride, phosgene and the like. The reaction temperature is not critical, and the reaction is usually carried out under cooling or at ambient temperature.

In case that the compound (V) has a free carboxy group at the 4-position, this reaction is preferably carried out by protecting the free carboxy group with a sililating agent (e.g. trimethylsilyl chloride, trimethylsilylacetamide, bis(trimethylsilyl)acetamide, etc.) before this reaction.

Suitable iminoetherifying agent reacted with thus obtained reaction product may include an alcohol, metal alkoxide and the like. Suitable alcohol may include alkanol (e.g. methanol, ethanol, propanol, isopropanol, butanol, t-butanol, 1,3-butanediol, etc.) which may be substituted with alkoxy (e.g. methoxy, ethoxy, propoxy, isopropoxy, butoxy, etc.). Suitable metal alkoxide may include alkali metal alkoxide (e.g. sodium alkoxide, potassium alkoxide, etc.), alkaline earth metal alkoxide (e.g. calcium alkoxide, barium alkoxide, etc.) and the like. The reaction temperature is not critical, and the reaction is usually carried out under cooling or at ambient temperature.

Thus obtained product is, if necessary, subjected to hydrolysis. The hydrolysis can readily be carried out by pouring the reaction mixture obtained above into water, but there may be previously added a hydrophilic solvent (e.g. methanol, ethanol, etc.), a base (e.g. alkali metal bicarbonate, trialkylamine, etc.) or an acid (e.g. diluted hydrochloric acid, acetic acid, etc.) to the water.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present invention includes, within its scope, the case that the protected carboxy is transformed into the free carboxy group according to reaction conditions and kinds of the protective groups in the course of the reaction or in posttreatment. The hydrolysis may include a method using an acid or a base and the like. These methods may be selected depending on the kind of the acyl groups to be eliminated.

Suitable acid may include an organic or an inorganic acid, for example, formic acid, trifluoroacetic acid, benzenesulfonic acid, p-toluenesulfonic acid, hydrochloric acid and the like. The acid suitable for the reaction can be selected according to the kind of acyl group to be eliminated. When the deacylation reaction is conducted with the acid, it can be carried out in the presence or absence of a solvent. Suitable solvent may include an organic solvent, water or a mixed solvent thereof. When trifluoroacetic acid is used, the deacylation reaction may be preferably carried out in the presence of anisole.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]undecene-5- or the like. The hydrolysis using a base is often carried out in water or a hydrophilic organic solvent or a mixed solvent thereof.

The reduction may include, for example, reduction with an alkali metal borohydride (e.g. sodium borohydride, etc.), catalytic reduction and the like.

The reaction temperature is not critical, and the reaction is usually carried out under cooling to warming.

Process A—(3)

(Va)→(Vb)

The compound (Vb) or a salt thereof can be prepared by subjecting the compound (Va) or its reactive derivative at the amino group or a salt thereof to acylation reaction.

The present reaction can be carried out in a similar manner to that of aforementioned Process 1.

Process A—(4)

(Vb)-(Vc)

The compound (Vc) or a salt thereof can be prepared by subjecting the compound (Vb) or a salt thereof to elimination reaction of the carboxy protective group.

The present reaction can be carried out in a similar manner to that of aforementioned Process 2.

Process B-(1)

(IIIb)-(II)

The object compound (II) or a salt thereof can be prepared by subjecting the compound (IIIb) or a salt thereof to reaction preparing quaternary ammonium salt.

Suitable salt of the compound (II) or (IIIb) can be referred to the ones as exemplified for the compound (I).

The present reaction can be carried out in a similar manner to that of aforementioned Process 3.

Process B-(2)

The object compound (II) or a salt thereof can be prepared by reacting the compound (VIIIa) or a salt thereof with the compound (XIVa) or a salt thereof.

Suitable salt of the compound (VIIIa) can be referred to the ones exemplified for the compound (I).

The present reaction can be carried out in a similar manner to that of aforementioned Process A-(1)-i).

Process B-(3)

The object compound (IIb) or a salt thereof can be prepared by reacting the compound (VIb) or a salt thereof with the compound (XIVa) or a salt thereof.

Suitable salt of the compound (VIb) can be refered to the ones exemplified for the compound (I).

The present reaction can be carried out in a similar manner to that of aforementioned Process A-(1)-i).

Process B-(4)

The object compound (IIId) or a salt thereof can be prepared by reacting the compound (VIa) or a salt thereof with the compound (XIV) or a salt thereof.

Suitable salt of the compound (VIa) can be refered to the ones exemplified for the compound (I).

The present reaction can be carried out in a similar manner to that of aforementioned Process A-(1)-i).

Process B-(5)

The object compound (IVa) or a salt thereof can be prepared by subjecting the compound (IV) or a salt thereof to elimination reaction of amino protective group.

The present reaction can be carried out in a similar manner to that of aforementioned Process 4.

Process B-(6)

The object compound (IVc) or a salt thereof can be prepared by subjecting the compound (IVb) or a salt thereof to reduction reaction.

The present reaction can be carried out in a similar manner to that of aforementioned Process A-(1)-ii).

Process C-(1)-i)

The object compound (X) or a salt thereof can be prepared by subjecting the compound (IX) or a salt thereof to reaction preparing quaternary ammonium salt.

The agent to be used in the present reaction preparing quaternary ammonium salt may include conventional one such as N-[2-halo(lower)alkyl]phthalimide (e.g. N-(2-bromoethyl)phthalamide, N-(2-bromopropyl)phthalimide, etc.), or the like.

The present reaction can be carried out in a similar manner to that of aforementioned Process 3:

Process C-(1)-ii)

The object compound (XI) or a salt thereof can be prepared by subjecting the compound (X) or a salt thereof to elimination reaction of the protective group.

The present reaction can be carried out in a similar manner to that of aforementioned Process 4.

Process C-(2)-i

The object compound (XII) or a salt thereof can be prepared by subjecting the compound (XI) or a salt thereof to reaction preparing disulfide.

The present reaction can be carried out by conventional manner.

Process C-(2)-ii

The object compound (XIIa) or a salt thereof can be prepared by subjecting the compound (XII) or a salt thereof to alkylation reaction of amino moiety.

The agent to be used in the present reaction may include conventional one such as a combination of formaldehyde and formic acid, or the like.

Process C-(2)-iii

The object compound (XIa) or a salt thereof can be prepared by subjecting the compound (XIIa) or a salt thereof to reaction preparing thiol.

The agent to be used in the present reaction may include conventional one such as triphenylphosphine.

Process C-(3)

The object compound (XIIa) or a salt thereof can be prepared by subjecting the compound (XIII) or a salt thereof to reaction preparing quaternary ammonium salt.

The present reaction can be carried out in a similar manner to that of aforementioned Process 3.

The object compounds (I) and pharmaceutically acceptable salts thereof of the present invention are novel compounds which exhibit high antibacterial activity and inhibit the growth of a wide variety of pathogenic microorganisms including Gram-positive and Gram-negative bacteria and are useful as antimicrobial agents. For therapeutic purpose, the compounds according to the present invention can be used in the form of conventional pharmaceutical preparation which contain said compounds, as an active ingredient, in admixture with a pharmaceutically acceptable carrier such as an organic or an inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives such as lactose, fumaric acid, citric acid, tartaric acid, stearic acid, maleic acid, succinic acid, malic acid magnesium stearate, terra alba, sucrose, corn starch, talc, gelatin, agar, pectin, peanut oil, olive oil, cacao butter, ethylene glycol, and the like.

While the dosage of the compounds will vary depending upon the age and condition of the patient, an average single dose of about 10 mg, 50 mg, 100 mg, 250 mg, 500 mg, and 1000 mg of the compounds according to the present invention was proved to be effective for treating infectious diseases, caused by pathogenic bacteria. In general, amounts between 1 mg/body and about 6,000 mg/body or even more may be administered per day.

In order to illustrate the usefulness of the object compound, anti-microbial activities of representative compounds of the present invention are shown below.

Minimal inhibitory concentration (A) Test Method

In vitro antibacterial activity was determined by the two-fold agar-plate dilution method as described below.

One loopful of an overnight culture of each test strain in trypticase-soy broth ($10^8$ viable cells per ml) was streaked on heart infusion agar (HI-agar) containing graded concentrations of representative test compound, and the minimal inhibitory concentration (MIC) was expressed in terms of µg/ml after incubation at 37° C. for 20 hours.

(B) Test Compounds (1) 7-[2-Ethoxyimino-2-(5-amino-1,2,4-thiadiazol-3-yl)acetamido]-3-[2-(1-methyl-3-pyridinio)thiovinyl]-3-cephem-4-carboxylate (syn isomer) (trans isomer).

(2) 7-[2-Allyloxyimino-2-(5-amino-1,2,4-thiadiazol-3-yl)acetamido]-3-{2-[1-(3-aminopropyl)-3-pyridinio]-thiovinyl}-3-cephem-4-carboxylate hydrochloride (syn isomer) (cis isomer).

(3) 7-[2-Allyloxyimino-2-(2-aminothiazol-4-yl)acetamido]-3-{2-[1-(3-N,N-dimethylaminopropyl)-3-pyridinio]thiovinyl}-3-cephem-4-carboxylate hydrochloride (syn isomer) (cis isomer).

(4) 7-[2-Allyloxyimino-2-(5-amino-1,2,4-thiadiazol-3-yl)acetamido]-3-{2-[1-(3-N,N-dimethylaminopropyl)-3-pyridinio]thiovinyl}-3-cephem-4-carboxylate hydrochloride (syn isomer) (cis isomer).

(C) Test Results

| Test strain | M.I.C. (µg/ml) Test Compounds | | | |
| --- | --- | --- | --- | --- |
|  | (1) | (2) | (3) | (4) |
| *Escherichia coli* 31 | <0.025 | 0.050 | <0.025 | 0.100 |
| *Klebsiella pneumoniae* 20 | 0.050 | 0.200 | 0.100 | 0.100 |
| *Staphylococcus aureus* 209P JC-1 | 0.390 | 0.200 | 0.200 | 0.200 |

The following preparations and examples are given for the purpose of illustrating the present invention in more detail.

Preparation of the starting compounds of the present invention.

Preparation 1

(1) A mixture of benzhydryl 7-tert-butoxycarbonylamino-3-(2-tosyloxyvinyl)-3-cephem-4-carboxylate-1-oxide (trans isomer) (7 g) and 3-mercaptopyridine (1.33 g) in dimethylformamide (50 ml) containing diisopropylethylamine (4.5 g) was stirred at ambient temperature for 2 hours. The resulting solution was poured into a mixture of ice-cooled water (200 ml) and ethylacetate (200 ml). The separated organic layer was washed in turn with water, 10% aqueous hydrochloric acid and a saturated aqueous solution of sodium bicarbonate and brine. The solvent was evaporated in vacuo to give benzhydryl 7-tert-butoxycarbonylamino-3-[2-(3-pyridyl)thiovinyl]-3-cephem-4-carboxylate-1-oxide. (trans isomer) (5.2 g).

IR (Nujol): 3400–3200 (broad), 1780, 1710, 1490 cm$^{-1}$

NMR (DMSO-d$_6$) δ: 1.42 (9H, s), 3.65 and 4.57 (2H, ABq, J=20 Hz), 5.05 (1H, d, J=5 Hz), 5.78 (1H, dd, J=5, 8 Hz), 6.33 (1H, d, J=8 Hz), 6.93 (1H, s), 7.0–8.8 (14H, m).

(2) The following compound was obtained according to a similar manner to that of Preparation 1-1).

(1) Benzhydryl 7-tert-butoxycarbonylamino-3-[2-(2-pyridyl)thiovinyl]-3-cephem-4-carboxylate-1-oxide (trans isomer).

IR (Nujol): 3400–3200, 1780, 1710, 1700, 1550 cm$^{-1}$

NMR (CDCl$_3$) δ: 1.50 (9H, s), 3.30, 4.23 (2H, ABq, J=18 Hz), 4.50 (1H, d, J=5 Hz), 5.7–5.87 (2H, m), 6.97 (1H, s), 7.0–7.67 (16H, m), 8.43 (1H, d, J=5 Hz).

(2) Benzhydryl 7-tert-butoxycarbonylamino-3-[2-(2-pyrimidinyl)thiovinyl]-3-cephem-4-carboxylate-1-oxide (trans isomer).

IR (Nujol): 3400–3300, 1785, 1710, 1550, 1500 cm$^{-1}$

NMR (CDCl$_3$) δ: 1.50 (9H, s), 3.28 and 4.23 (2H, ABq, J=18 Hz), 5.53 (1H, d, J=5 Hz), 5.7–5.85 (2H, m), 7.03 (1H, s), 7.1–7.67 (14H, m), 8.57 (2H, d, J=5 Hz).

(3) Benzhydryl 7-tert-butoxycarbonylamino-3-[2-(2-pyrazinyl)thiovinyl]-3-cephem-4-carboxylate-1-oxide (trans isomer).

IR (Nujol): 3400, 1788, 1710, 1500 cm$^{-1}$

NMR (DMSO-d$_6$) δ: 1.50 (9H, s), 3.78 and 4.65 (2H, ABq, J=18 Hz), 5.10 (1H, d, J=5 Hz), 5.85 (1H, dd, J=5, 10 Hz), 6.43 (1H, d, J=10 Hz), 7.03 (1H, s), 7.0–7.8 (12H, m), 8.53 (2H, m), 8.77 (1H, m).

(4) Benzhydryl 7-tert-butoxycarbonylamino-3-[2-(3-pyridyl)thiovinyl]-3-cephem-4-carboxylate-1-oxide (cis isomer).

IR (Nujol): 3400–3200 (broad), 1780, 1700, 1490 cm$^{-1}$

NMR (CDCl$_3$) δ: 1.48 (9H, s), 3.72 (2H, d-d, J=18 Hz), 4.50 (1H, d, J=5 Hz), 5.67–6.00 (2H, m), 6.27 (1H, d, J=10 Hz), 6.88 (1H, d, J=10 Hz), 7.1–7.83 (12H, m), 8.45–8.73 (2H, m).

(5) Benzhydryl 7-tert-butoxycarbonylamino-3-[2-(2-pyridyl)thiovinyl]-3-cephem-4-carboxylate-1-oxide (cis isomer).

IR (Nujol): 3350, 1780, 1710, 1570 cm$^{-1}$

NMR (CDCl$_3$) δ: 1.55 (9H, s), 3.50 and 4.35 (2H, ABq, J=18 Hz), 5.83 (2H, m), 6.50 (1H, b s), 7.00 (1H, s), 7.05–8.50 (15H, m).

(6) Benzhydryl 7-[2-ethoxyimino-2-(5-amino-1,2,4-thiadiazol-3-yl)acetamido]-3-[2-(5-nitro-2-pyridyl)thiovinyl]-3-cephem-4-carboxylate-1-oxide (syn isomer) (trans isomer)

Preparation 2

(1) To a solution of benzhydryl 7-tert-butoxycarbonylamino-3-[2-(3-pyridyl)thiovinyl]-3-cephem-4-carboxylate-1-oxide (trans isomer) (12.3 g) in dimethylformamide (70 ml) was added phosphorus trichloride (5.5 g) at −40° C. After being stirred at the same temperature for 30 minutes, the reaction mixture was poured into a mixture of ethyl acetate (200 ml) and water (100 ml). The separated organic layer was washed in turn with 5% aqueous sodium bicarbonate, water, and brine. The solvent was evaporated in vacuo to give benzhydryl 7-tert-butoxycarbonylamino-3-[2-(3-pyridyl)thiovinyl]-3-cephem-4-carboxylate (trans isomer) (11.1 g).

IR (Nujol): 3200, 1775, 1710, 1700, 1510 cm$^{-1}$

NMR (DMSO-d$_6$) δ: 1.45 (9H, s), 3.64 and 4.08 (2H, ABq, J=18 Hz), 3.18 (1H, d, J=5 Hz), 3.50 (1H, dd, J=5, 8 Hz), 6.95 (1H, s), 7.0–8.8 (14H, m)

(2) The following compound was obtained according to a similar manner to that of Preparation 2-1).

(1) Benzhydryl 7-tert-butoxycarbonylamino-3-[2-(2-pyridyl)thiovinyl]-3-cephem-4-carboxylate (trans isomer).

IR (Nujol): 3300, 1770, 1700, 1670 cm$^{-1}$

NMR (CDCl$_3$) δ: 1.53 (9H, s), 3.65, 4.1 (2H, ABq, J=16 Hz), 5.07 (1H, d, J=5 Hz), 5.50 (1H, dd, J=5 Hz, 8 Hz), 7.00 (1H, s), 7.1–8.0 (15H, m), 8.50 (1H, d, J=4 Hz).

(2) Benzhydryl 7-tert-butoxycarbonylamino-3-[2-(2-pyrazinyl)thiovinyl]-3-cephem-4-carboxylate (trans isomer)

IR (Nujol): 3280, 1772, 1703, 1500 cm$^{-1}$

NMR (DMSO-d$_6$) δ: 1.43 (9H, s), 3.67 and 4.07 (2H, ABq, J=18 Hz), 5.18 (1H, d, J=5 Hz), 5.57 (1H, d, J=5,8 Hz), 7.00 (1H, s), 7.0–7.7 (12H, m), 8.02 (1H, d, J=8 Hz), 8.50 (2H, m). 8.70 (1H, m).

(3) Benzhydryl 7-tert-butoxycarbonylamino-3-[2-(3-pyridyl)thiovinyl]-3-cephem-4-carboxylate (cis isomer), IR (Nujol): 3300, 3200, 1785, 1710, 1525 cm$^{-1}$ NMR (CDCl$_3$) δ: 1.47 (9H, s), 3.82 (2H, b-s), 5.04 (1H, d, J=5 Hz), 5.32–5.72 (2H, m), 6.25 and 6.78 (1H, dx2, J=10 Hz), 7.11–7.83 (2H, m), 8.33–8.78 (2H, m).

(4) Benzhydryl 7-tert-butoxycarbonylamino-3-[2-(2-pyridyl)thiovinyl]-3-cephem-4-carboxylate (cis isomer).

IR (Nujol): 3300, 1795, 1715, 1670 cm$^{-1}$

NMR (CDCl$_3$) δ: 1.45 (9H, s), 3.78 (2H, b s), 5.00 (1H, d, J=5 Hz), 5.50 (1H, dd, J=5 Hz, 8 Hz), 6.93 (1H, s), 6.83 (1H, d, J=10 Hz), 7.10–8.50 (15H, m).

(5) Benzhydryl 7-[2-ethoxyimino-2-(5-amino-1,2,4-thiadiazol-3-yl)acetamido]-3-[2-(2-dimethylaminoethyl)thiovinyl]-3-cephem-4-carboxylate (syn isomer) (trans isomer).

(6) Benzhydryl 7-[2-ethoxyimino-2-(5-amino-1,2,4-thiadiazol-3-yl)acetamido]-3-[2-(5-nitro-2-pyridyl)thiovinyl]-3-cephem-4-carboxylate (syn isomer) (trans isomer).

IR (Nujol): 3300, 1780, 1680, 1620, 1595, 1570, 1520 cm$^{-1}$

NMR (DMSO-d$_6$) δ: 1.32 (3H, t, J=7 Hz), 3.92 (2H, b s), 4.25 (2H, q, J=7 Hz), 5.34 (1H, d, J=4 Hz), 6.00 (1H, d-d, J=4, 8 Hz), 7.01 (1H, s), 7.20–7.91 (12H, m), 8.42 (1H, d, J=3 Hz), 8.57 (1H, d, J=3 Hz), 9.26 (1H, d, J=3 Hz), 9.68 (1H, d, J=8 Hz).

Preparation 3

(1) To a cooled solution of benzhydryl 7-tert-butoxycarbonylamino-3-[2-(3-pyridyl)thiovinyl]-3-cephem-4-carboxylate (trans isomer) (4.7 g) in acetonitrile (100 ml) was added p-toluenesulfonic acid (5.3 g). The reaction mixture was stirred at ambient temperature for 2 hours. After removal of the solvent, the residue was dissolved in ethyl acetate and 5% aqueous sodium bicarbonate. The separated organic layer was washed in turn with water and brine, dried over magnesium sulfate. The solvent was evaporated in vacuo to give benzhydryl 7-amino-3-[2-(3-pyridyl)thiovinyl]-3-cephem-4-carboxytate (trans isomer) (3.2 g).

IR (Nujol): 3200 (broad), 1770, 1710, 1650 cm$^{-1}$

NMR (DMSO-d$_6$) δ: 3.60 and 4.10 (2H, ABq, J=18 Hz), 4.85 (1H, d, J=4 Hz), 5.08 (1H, d, J=4 Hz), 6.83 (1H, d, J=16 Hz), 7.10 (1H, s), 7.1–8.8 (16H, m).

(2) The following compound was obtained according to a similar manner to that of Preparation 3-1).

Benzhydryl 7-amino-3-[2-(2-pyridyl)thiovinyl]-3-cephem-4-carboxylate (trans isomer).

IR (Nujol): 1760–1770, 1710, 1650 cm$^{-1}$

NMR (CDCl$_3$) δ: 3.43–3.80 (2H, m), 4.73 (1H, d, J=4 Hz), 5.00 (1H, d, J=4 Hz), 7.00 (1H, s), 7.1–7.75 (15H, m), 8.45 (1H, d, J=4 Hz).

Preparation 4

To a solution of benzhydryl 7-tert-butoxycarbonylamino-3-[2-(2-pyrimidinyl)thiovinyl]-3-cephem-4-carboxylate-1-oxide (trans isomer) (4.8 g) in N,N-dimethylformamide (25 ml) was added phosphorus trichloride (0.8 ml) at −30° C. After being stirred for an hour at −30° C., the reaction mixture was poured into a mixture of ethyl acetate (300 ml) and water (300 ml). The separated organic layer was washed in turn with 5% aqueous solium bicarbonate, water and brine. The solvent was evaporated in vacuo to give benzhydryl 7-tert-butoxycarbonylamino-3-[2-(2-pyrimidinyl)thiovinyl]-3-cephem-4-carboxylate (trans isomer) and it was added with acetonitrile (100 ml) and p-toluene sulfonic acid (3.5 g). The mixture was stirred for 2 hours at 35° C. After removal of the solvent the residue was dissolved in ethyl acetate and 5% aqueous sodium bicarbonate. The separated organic layer was washed in turn with water and bine, dried over magnesium sulfate. The solvent was evaporated in vacuo to give benzhydryl 7-amino-3-[2-(2-pyrimidinyl)thiovinyl]-3-cephem-4-carboxylate (trans isomer) (2.5 g).

IR (Nujol): 3300–3400, 1770, 1720, 1560, 1550 cm$^{-1}$

NMR (DMSO-d$_6$) δ: 3.65, 4.04 (2H, ABq, J=18 Hz), 4.8–5.2 (2H, m), 6.90 (1H, d, J=18 Hz), 7.00 (1H, s), 7.17–7.67 (13H, m), 8.68 (2H, d, J=5 Hz).

Preparation 5

(1) To a solution of benzhydryl 7-amino-3-[2-(3-pyridyl)thiovinyl]-3-cephem-4-carboxylate (trans isomer) (3 g) in tetrahydrofuran (30 ml) containing monotrimethylsilyl acetamide (5 g) was added 2-ethoxyimino-2-(5-amino-1,2,4-thiadiazol-3-yl)acetyl chloride hydrochloride (syn isomer) (1.8 g) under stirring at −10°-0° C. The reaction mixture was stirred at the same temperature for 30 minutes. After addition of ethyl acetate (150 ml) and a small amount of water, the separated organic layer was washed in turn with saturated aqueous sodium bicarbonate and brine, dried over magnesium sulfate. The solvent was evaporated in vacuo to give benzhydryl 7-[2-ethoxyimino-2-(5-amino-1,2,4-thiadiazol-3-yl)acetamido]-3-[2-(3-pyridyl)thiovinyl]-3-cephem-4-carboxylate (syn isomer) (trans isomer) (3.1 g).

IR (Nujol): 3300, 3150, 1780, 1720, 1680, 1610, 1520 cm$^{-1}$

NMR (DMSO-d$_6$) δ: 1.27 (3H, t, J=7 Hz), 3.6–4.2 (2H, m), 4.20 (2H, q, J=7 Hz), 5.25 (1H, d, J=5 Hz), 5.85 (1H, dd, J=5, 8 Hz), 6.82 (1H, d, J=16 Hz), 6.90 (1H, s), 7.0–7.7 (11H, m), 7.5–8.8 (6H, m), 9.61 (1H, d, J=8 Hz).

(2) The following compounds were obtained according to a similar manner to that Preparation 5-1).

(1) Benzhydryl 7-[2-methoxyimino-2-(2-formamidothiazol-4-yl)acetamido]-3-[2-(3-pyridyl)thiovinyl]-3-cephem-4-carboxylate (syn isomer) (trans isomer).

IR (Nujol): 3300, 1780, 1700, 1650, 1550 cm$^{-1}$

NMR (DMSO-d$_6$) δ: 3.92 (3H, s), 3.70 and 4.15 (2H, ABq, J=17 Hz), 5.27 (1H, d, J=4 Hz), 5.88 (1H, d, J=4, 8 Hz), 6.86 (1H, d, J=16 Hz), 6.92 (1H, s), 7.2–8.8 (16H, m), 9.7 (1H, d, J=8 Hz), 11.6 (1H, s).

(2) Benzhydryl 7-[2-ethoxyimino-2-(5-amino-1,2,4-thiadiazol-3-yl)acetamido]-3-[2-(2-pyridyl)thiovinyl]-3-cephem-4-carboxylate (syn isomer) (trans isomer).

IR (Nujol): 3390, 3250, 1760, 1715, 1660, 1620 cm$^{-1}$

NMR (DMSO-d$_6$) δ: 9.62 (1H, d, J=8 Hz), 8.48 (1H, d, J=4 Hz), 8.12 (2H, b-s), 7.17–7.78 (14H, m), 7.00 (1H, d, J=16 Hz), 6.97 (1H, s), 5.93 (1H, dd, J-8 Hz, 5 Hz), 5.30 (1H, d, J=5 Hz), 4.22 (2H, q, J=7 Hz), 3.93 (2H, ABq, J=18 Hz), 1.32 (3H, t, J=7 Hz).

(3) Benzhydryl 7-[2-ethoxyimino-2-(5-amino-1,2,4-thiadiazol-3-yl)acetamido]-3-[2-(2-pyrimidinyl)thiovinyl]-3-cephem-4-carboxylate (syn isomer) (trans isomer).

mp 164°–167° C. (dec.)

IR (Nujol): 3300, 3150, 1770, 1720, 1670, 1620 cm$^{-1}$

NMR (DMSO-d$_6$) δ: 1.27 (3H, t, J=5 Hz), 3.87(2H, ABq, J=18 Hz), 4.20 (2H, q, J=7 Hz), 5.28 (1H, d, J=5 Hz), 5.88 (1H, dd, J=8 Hz, 5 Hz), 6.23 (1H, d, J=16 Hz), 6.93 (1H, s), 7.2–7.6 (11H, m), 8.07 (2H, b-s), 8.65 (2H, d, J=5 Hz), 9.58 (1H, d, J=8 Hz).

(4) Benzhydryl 7-[2-(2- tritylaminothiazol-4-yl)glyoxylamido]-3-[2-(3-pyridyl)thiovinyl]-3-cephem-4-carboxylate (syn isomer) (trans isomer).

IR (Nujol): 1780, 1710, 1660 cm$^{-1}$

NMR (DMSO-d$_6$) δ: 3.67–4.02 (2H, m), 5.27 (1H, d, J=5 Hz), 5.68 (1H, dd, J=8 Hz, 5 Hz), 6.93 (1H, s), 7.06–7.7 (27H, m), 7.87 (1H, s), 7.85–8.83 (4H, m), 9.75 (1H, d, J=8 Hz).

(5) 7-[2-Carboxymethoxyimino-2-(5-amino-1,2,4-thiadiazol-3-yl)acetamido]-3-[2-(3-pyridyl)thiovinyl]-3-cephem-4-carboxylic acid (syn isomer) (trans isomer).

IR (Nujol): 3300, 1760, 1600, 1400, 1160, 1050 cm$^{-1}$

NMR (DMSO-d$_6$) δ: 3.40–3.70 (2H, m), 4.37 (2H, s), 5.03 (1H, d, J=5 Hz), 5.67 (1H, dd, J=8 Hz, 5 Hz), 6.50 (1H, d, J=16 Hz), 7.37 (1H, d, J=16 Hz), 7.30–8.57 (4H, m), 11.17 (1H, d, J=8 Hz).

(6) Benzhydryl 7-[2-(3-benzhydryloxycarbonylpropoxyimino)-2-(5-amino-1,2,4-thiadiazol-3-yl)acetamido]-3-[2-(3-pyridyl)thiovinyl]-3-cephem-4-carboxylate (syn isomer) (trans isomer).

(7) Benzhydryl 7-[2-(1-methyl 1-benzhydryloxycarbonylethoxyimino)-2-(5-amino-1,2,4-thiadiazol-3-yl)acetamido]-3-[2-(3-pyridyl)thiovinyl]-3-cephem-4-carboxylate (syn isomer) (trans isomer).

Preparation 6

(1) To a solution of benzhydryl 7-[2-metoxyimino-2-(2-formamidothiazol-4-yl)acetamido]-3-[2-(3-pyridyl)-thiovinyl]-3-cephem-4-carboxylate (syn isomer) (trans isomer) (2 g) in methanol (20 ml) was added conc. hydrochloric acid (0.85 ml) at ambient temperature and the resultant mixture was stirred at 25°–30° C. for 2 hours. Water and ethyl acetate were added to the reaction mixture and the resultant mixture was adjusted to pH 7.0 with saturated aqueous sodium bicarbonate. The separated organic layer was evaporated in vacuo to give a yellowish residue. A mixture of this residue and trifuluoroacetic acid (5 ml) containing anisole (1 ml) in dichloromethane (10 ml) was stirred at 5°–10° C. for an hour. The mixture was poured into diisopropyl ether (100 ml) to give precipitate, which was collected by filtration and dissolved in 5% aqueous sodium bicarbonate at pH 5.5. The resulting solution was chromatographed on macropourous non-ionic resin "Diaion-HP-20" and eluted with 20% aqueous solution of isopropyl alcohol. The fractions containing object compound were concentrated and acidified at pH 2.2 with conc. hydrochloric acid to give 7-[2-methoxyimino-2-(2-aminothiazol-4-yl)acetamido]-3-[2-(3-pyridyl)thiovinyl]-3-cephem-4-carboxylic acid (syn isomer) (trans isomer) (0.07 g).

IR (Nujol): 3300, 1770, 1670, 1540 cm$^{-1}$

NMR (DMSO-d$_6$) δ: 3.60 and 4.00 (2H, ABq, J=18 Hz), 3.82 (3H, s), 5.15 (1H, d, J=5 Hz), 5.68 (1H, dd, J=5, 8 Hz), 6.73 (1H, s), 6.90, 7.17 (2H, 2xd, J=16 Hz), 7.0–8.8 (4H, m), 9.58 (1H, d, J=8 Hz).

(2) The following compounds were obtained according to a similar manner to that of Preparation 6-1).

(1) 7-[2-Ethoxyimino-2-(5-amino-1,2,4-thiadiazol-3-yl)acetamido]-3-[2-(3-pyridyl)thiovinyl]-3-cephem-4-carboxylic acid (syn isomer) (trans isomer).

IR (Nujol): 3300, 1770, 1670, 1620, 1530 cm$^{-1}$

NMR (DMSO-d$_6$) δ: 1.25 (3H, t, J=7 Hz), 3.80 (2H, ABq, J=18 Hz), 4.20 (2H, q, J=7 Hz), 5.15 (1H, d, J=5 Hz), 5.73 (1H, dd, J=5, 8 Hz), 6.88 and 7.14 (2H, 2xd, J=16 Hz), 7.3–8.8 (4H, +2H m), 9.52 (1H, d, J=8 Hz).

(2) 7-[2-Ethoxyimino-2-(5-amino-1,2,4-thiadiazol-3-yl)acetamido]-3-[2-(2-pyridyl)thiovinyl]-3-cephem-4-carboxylic acid (syn isomer) (trans isomer).

mp 180°–184° C. (dec.).

IR (Nujol): 3450, 3300, 3200, 2400–2600, 1775, 1680, 1655, 1615 cm$^{-1}$

NMR (DMSO-d$_6$) δ: 1.23 (3H, t, J=7 Hz), 3.83 (2H, ABq, J=18 Hz), 4.17 (2H, q, J=7 Hz), 5.18 (1H, d, J=5 Hz), 5.77 (1H, dd, J=8 Hz, 5 Hz), 7.03 (1H, d, J=16 Hz), 7.1–7.83 (4H, m), 8.07 (2H, b-s), 8.48 (1H, d, J=4 Hz), 9.55 (1H, d, J=8 Hz).

(3) 7-[2-Ethoxyimino-2-(5-amino-1,2,4-thiadiazol-3-yl)acetamido]-3-[2-(2-pyrimidinyl)thiovinyl]-3-cephem-4-carboxylic acid (syn isomer) (trans isomer).

mp 194°–196° C. (dec.).

IR (Nujol): 3250, 3150, 2450–2550, 1760, 1670, 1655, 1620 cm$^{-1}$

NMR (DMSO-d$_6$) δ: 1.32 (3H, t, J=7 Hz), 3.72 (2H, ABq, 18 Hz), 4.17 (2H, q, J=7 Hz), 5.28 (1H, d, J=5 Hz), 5.85 (1H, dd, J=8 Hz, 5 Hz), 7.13 (1H, d, J=16 Hz), 7.48 (1H, d, J=16 Hz), 7.33 (1H, m), 8.15 (2H, b-s), 8.70 (2H, d, J=5 Hz), 9.62 (1H, d, J=8 Hz).

(4) 7-[2-Ethoxyimino-2-(5-amino-1,2,4-thiadiazol-3-yl)acetamido]-3-[2-(5-nitro-2-pyridyl)thiovinyl]-3-cephem-4-carboxylic acid (syn isomer) (trans isomer).

IR (Nujol): 1780, 1690, 1600, 1580, 1520 cm$^{-1}$

NMR (DMSO-d$_6$) δ: 1.35 (3H, t, J=7 Hz), 3.7–4.45 (4H, m), 5.30 (1H, d, J=4 Hz), 5.90 (1H, dd, 4, 8 Hz), 7.3–9.3 (3H, m), 9.71 (1H, d, J=8 Hz).

(5) 7-[2-(3-Carboxypropoxyimino)-2-(5-amino-1,2,4-thiadiazol-3-yl)acetamido]-3-[2-(3-pyridyl)thiovinyl]-3-cephem-4-carboxylic acid (syn isomer) (trans isomer).

IR (Nujol): 3300, 1770, 1670, 1620, 1530 cm$^{-1}$

NMR (DMSO-d$_6$) δ: 1.6–2.7 (4H, m), 3.8–4.3 (4H, m), 5.23 (1H, d, J=4 Hz), 5.82 (1H, dd, J=4, 8 Hz), 7.06 (2H, s), 7.2–8.8 (4H, m), 9.62 (1H, d, J=8 Hz).

(6) 7-[2-(1-Methyl-1-carboxyethoxyimino)-2-(5-amino-1,2,4-thiadiazol-3-yl)acetamido]-3-[2-(3-pyridyl)thiovinyl]-3-cephem-4-carboxylic acid (syn isomer) (trans isomer).

IR (Nujol): 3300, 1770, 1670, 1610, 1520 cm$^{-1}$

NMR (DMSO-d$_6$) δ: 1.48 (6H, s), 3.5–4.2 (2H, m), 5.15 (1H, d, J=5 Hz), 5.85 (1H, dd, J=5, 8 Hz), 7.0 (2H, s), 7.2–8.8 (4H, m), 9.43 (1H, d, J=8 Hz).

Preparation 7

(1) A mixture of benzhydryl 7-tert-butoxycarbonylamino-3-[2-(2-pyridyl)thiovinyl]-3-cephem-4-carboxylate (trans isomer) (5.0 g) N,N-dimethylformamide (25 ml) and methyl iodide (5 ml) was allowed to stand for 9 days at ambient temperature. The reaction mixture was poured into diisopropyl ether and the resultant oily residue was triturated with ethyl acetate and collected by filtration to give benzhydryl 7-tert-butoxycarbonylamino-3-[2-(1-methyl-2-pyridinio)thiovinyl]-3-cephem-4-carboxylate iodide (trans isomer) (5.2 g).

IR (Nujol): 3400, 1775, 1705–1695, 1650, 1600 cm$^{-1}$

NMR (DMSO-d$_6$) δ: 1.38 (9H, b-s), 4.00 (2H, ABq, J=18 Hz), 4.23 (3H, s), 5.23 (1H, d, J=5 Hz), 5.65 (1H), dd, J=8 Hz, 5 Hz), 7.00 (1H, s), 7.17–7.55 (11H, m), 7.8–8.5 (4H, m), 9.2 (1H, d, J=5 Hz).

(2) The following compound was obtained according to a similar manner to that of Preparation 7-1).

(1) Benzhydryl 7-tert-butoxycarbonylamino-3-[2-(1-methyl-3-pyridinio)thiovinyl]-3-cephem-4-carboxylate iodide (trans isomer).

IR (Nujol): 3350–3450, 1775, 1710, 1660, 1620 cm$^{-1}$

NMR (DMSO-d$_6$) δ: 1.4 (9H, s), 3.5–4.1 (2H, m), 4.35 (3H, s), 5.22 (1H, d, J=5 Hz), 5.58 (1H, dd, J=5 Hz, 8 Hz), 6.97 (1H, s), 7.1–7.6 (12H, m), 8.0–8.9 (11H, m), 9.1 (1H, broad s).

(2) Benzhydryl 7-tert-butoxycarbonylamino-3-[2-(4-methyl-2-pyrazinio)thiovinyl]-3-cephem-4-carboxylate iodide (trans isomer).

IR (Nujol): 3350, 1785, 1717 cm$^{-1}$

NMR (DMSO-d$_6$) δ: 1.47 (9H, s), 3.70 and 4.17 (2H, ABq, J=17 Hz), 4.33 (3H, s), 5.23 (1H, d, J=5 Hz), 5.60 (1H, dd, J=5 Hz, 8 Hz), 7.00 (1H, s), 7.2–7.6 (12H, m), 8.05 (1H, d, J=8 Hz), 8.87 (1H, d, J=4 Hz), 9.30 (1H, d, J=4 Hz), 9.33 (1H, s).

(3) Benzhydryl 7-tert-butoxycarbonylamino-3-[2-(1-methyl-3-pyridinio)thiovinyl]-3-cephem-4-carboxylate iodide (cis isomer).

IR (Nujol): 3400–3200 (broad), 1770, 1710, 1660, 1620, 1520 cm$^{-1}$

NMR (DMSO-d$_6$) δ: 1.40 (9H, s), 3.65 and 3.95 (2H, ABq, J=18 Hz), 4.3 (3H, s), 5.18 (1H, d, J=5 Hz), 5.56 (1H, d-d, J=5 Hz, 8 Hz), 6.85 (1H, d, J=8 Hz), 6.88 (1H, s), 7.03–7.73 (10H, m), 7.75–9.15 (4H, m).

(4) Benzhydryl 7-tert-butoxycarbonylamino-3-[2-(1-methyl-2-pyridinio)thiovinyl]-3-cephem-4-carboxylate iodide (cis isomer).

IR (Nujol): 3300, 1780, 1720, 1680, 1615, 1565 cm$^{-1}$

NMR (DMSO-d$_6$) δ: 1.47 (9H, s), 3.5–4.20 (2H, m), 4.15 (3H, s), 5.25 (1H, d, J=5 Hz), 5.67 (1H, dd, J=5 Hz, 8 Hz), 6.73 (1H, d, J=10 Hz), 7.03 (1H, d, J=10 Hz), 6.93 (1H, s), 7.3–9.10 (15 H, m).

(5) Benzhydryl 7-[2-hydroxy-2-(2-tritylaminothiazol-4-yl)acetamido]-3-[2-(1-methyl-3-pyridinio)thiovinyl]-3-cephem-4-carboxylate iodide (trans isomer).

NMR (DMSO-d$_6$) δ: 3.5–4.1 (2H, m), 4.33 (3H, s), 4.9 (1H, s), 5.23 (1H, d, J=5 Hz), 5.77 (1H, dd, J=8 Hz, 5 Hz), 6.53 (1H, s), 6.95 (1H, s), 7.02–7.67 (27H, m), 7.68–9.3 (4H, m).

(6) Benzhydryl 7-[2-ethoxyimino-2-(5-amino-1,2,4-thiadiazol-3-yl)acetamido]-3-[2-(1-benzhydryloxycarbonylmethyl-3-pyridinio)thiovinyl]-3-cephem-4-carboxylate bromide (syn isomer) (trans isomer).

IR (Nujol): 3250–3400, 1780, 1750, 1720, 1660, 1620 cm$^{-1}$

NMR (DMSO-d$_6$) δ: 1.13 (3H, t, J=6 Hz), 3.45 (2H, m), 4.2 (2H, q, J=7 Hz), 5.33 (1H, d, J=5 Hz), 5.75–6.10 (3H, m), 6.95 (1H, s), 7.03 (1H, s), 7.00 (1H, d, J=16 Hz), 7.2–7.7 (21H, m), 8.0–9.33 (3H, m).

Preparation 8

To a solution of benzhydryl 7-[2-(2-tritylaminothiazol-4-yl)glyoxylamido]-3-[2-(3-pyridyl)thiovinyl]-3-cephem-4-carboxylate (syn isomer) (trans isomer) (3.1 g) in a mixture of methanol (16 ml) and tetrahydrofuran (16 ml) was added sodium borohydride (0.033 g) under ice-cooling and the mixture was stirred for 10 minutes. The reaction mixture was adjusted to pH 7.0 with 10% hydrochloric acid and extracted with ethyl acetate. The separated organic layer was washed with a saturated aqueous solution of sodium chloride, dried over magnesium sulfate and concentrated in vacuo to give benzhydryl 7-[2-(2-tritylaminothiazol-4-yl)-2-hydroxyacetamido]-3-[2-(3-pyridyl)thiovinyl]-3-cephem-4-carboxylate (trans isomer) (2.84 g).

IR (Nujol): 3300, 1780, 1720, 1680 cm$^{-1}$

NMR (DMSO-d$_6$) δ: 3.56–4.02 (2H, m), 4.9 (1H, s), 5.22 (1H, d, J=5 Hz), 5.77 (1H, dd, J=8 Hz, 5 Hz), 6.45 (1H, s), 6.93 (1H, s), 7–7.67 (27H, m), 7.6–8.7 (4H, m).

Preparation 9-1)

To an ice-cooled solution of 7-[2-ethoxyimino-2-(5-amino-1,2,4-thiadiazol-3-yl)acetamido]-3-[2-(5-nitro-2-pyridyl)thiovinyl]-3-cephem-4-carboxylic acid (syn isomer) (trans isomer) (1.35 g) in an aqueous solution of sodium bicarbonate (30 ml) was added sodium hydrosulfite (4.05 g) under stirring. The mixture was stirred for 30 minutes at room temperature and cooled in an ice-bath and acidified to pH 3.5 with 10% hydrochloric acid. The precipitate was collected, washed and dried to give 1.05 g of 7-[2-ethoxyimino-2-(5-amino-1,2,4-thiadiazol-3-yl)acetamido]-3-[2-(5-amino-2-pyridyl)thiovinyl)-3-cephem-4-carboxylic acid (syn isomer) (trans isomer).

IR (Nujol): 3300, 1770, 1670, 1620, 1530 cm$^{-1}$

NMR (DMSO-d$_6$) δ: 1.27 (3H, t, J=6 Hz), 3.85 (2H, b s), 4.20 (2H, q, J=6 Hz), 5.17 (1H, d, J=5 Hz), 5.77 (1H, dd, J=5, 8 Hz), 7.0–7.5 (4H, m), 8.10 (1H, s), 9.52 (1H, d, J=8 Hz).

Preparation 9-2)

To a suspension of phosphorus pentachloride in toluene was added 2-ethoxyimino-2-(5-amino-1,2,4-thiadiazol-3-yl)acetic acid (syn isomer) under cooling at 0° C. and stirring, which was continued for 45 minutes at 4° to 8° C. The reaction mixture was poured into ice-cold water under stirring. The organic layer was separated out, washed with cold water and brine, dried over magnesium sulfate and evaporated to dryness. The residue was triturated in diisopropyl ether and the mixture was stirred for 10 minutes at 3° C. The resulting precipitate was filtered, washed with cold diisopropyl ether and dried to give 2-ethoxyimino-2-(5-dichlorophosphorylamino-1,2,4-thiadiazol-3-yl)acetyl chloride (syn isomer). mp 115° C.

IR (Nujol): 1780, 1590, 1530, 1220, 1050, 960, 910 cm$^{-1}$

NMR (acetone-d$_6$) δ: 1.37 (3H, t, J=7 Hz), 4.45 (2H, q, J=7 Hz).

Analysis for C$_6$H$_6$N$_4$O$_3$PSCl$_3$:

| | C | H | N | Cl | P |
|---|---|---|---|---|---|
| calc'd | 20.48 | 1.71 | 15.93 | 30.33 | 8.82 |
| found | 20.79 | 1.78 | 16.22 | 30.63 | 8.98 |

Preparation 10

The following compound was obtained according to a similar manner to that of Preparation 1-1).

Benzhydryl 7-[2-allyloxyimino-2-(5-amino-1,2,4-thiadiazol-3-yl)acetamido]-3-[2-(3,4-tetramethylenepyridazin-6-yl)thiovinyl]-3-cephem-4-carboxylate-1-oxide (syn isomer) (trans isomer).

IR (Nujol): 1780, 1710, 1660, 1610, 1520 cm$^{-1}$

NMR (DMSO-d$_6$) δ: 1.76 (4H, m), 2.90 (4H, m), 3.84 (2H, ABq, J=18 Hz), 4.68 (2H, d, J=5 Hz), 5.17 (1H, d, J=5 Hz), 5.28 (2H, m), 5.96 (1H, dd, J=5 Hz, 8 Hz), 6.05 (1H, m), 6.96 (1H, s), 7.1–7.7 (13H, m), 8.06 (2H, broad s), 9.08 (1H, d, J=8 Hz).

Preparation 11

The following compounds were obtained according to a similar manner to that of Preparation 2-1).

(1) Benzhydryl 2-[2-allyloxyimino-2-(5-amino-1,2,4-thiadiazol-3-yl)acetamido]-3-[2-(1,3,4-thiadiazol-2-yl)thiovinyl]-3-cephem-4-carboxylate (syn isomer) (trans isomer).

IR (Nujol): 3300 (broad), 1790, 1740, 1690, 1640 cm$^{-1}$

NMR (DMSO-d$_6$) δ: 3.40 (2H, s), 4.57–4.90 (2H, m), 4.93–5.67 (4H, m), 5.67–6.13 (2H, m), 6.13–6.90 (2H, m), 6.97 (1H, s), 7.0–7.57 (10H, m), 9.60 (1H, s).

(2) Benzhydryl 7-tert-butoxycarbonylamino-3-{2-[1-(2-N,N-dimethylaminoethyl)-1H-tetrazol-5-yl]thiovinyl}-3-cephem-4-carboxylate (trans isomer).

IR (Nujol): 3300, 3350, 1780, 1710, 1600 cm$^{-1}$

NMR (CDCl$_3$) δ: 1.50 (9H, m), 2.50 (6H, s), 3.05 (2H, m), 3.67 (2H, m), 4.50 (2H, m), 5.03 (1H, d, J=5 Hz), 5.60 (1H, m), 6.95 (1H, s), 7.33 (10H, m).

(3) Benzhydryl 7-[2-allyloxyimino-2-(5-amino-1,2,4-thiadiazol-3-yl)acetamido]-3-[2-(3,4-tetramethylenepyridazin-6-yl)thiovinyl]-3-cephem-4-carboxylate (syn isomer) (trans isomer).

IR (Nujol): 1770, 1710, 1670, 1610, 1520 cm$^{-1}$

NMR (DMSO-d$_6$) δ: 1.80 (4H, m), 2.80 (4H, m), 3.86 (2H, ABq, J=18 Hz), 4.66 (2H, d, J=5 Hz), 5.27 (1H, d, J=5 Hz), 5.30 (1H, m), 5.88 (1H, dd, J=5 Hz, 8 Hz), 5.90 (1H, m), 6.96 (1H, s), 6.8–7.7 (13H, m), 9.64 (1H, d, J=8 Hz).

(4) Benzhydryl 7-[2-allyloxyimino-2-(2-formamidothiazol-4-yl)-acetamido]-3-{2-[1-(3-N,N-dimethylaminopropyl)-3-pyridinio]-thiovinyl}-3-cephem-4-carboxylate chloride hydrochloride (syn isomer) (cis isomer).

NMR (DMSO-d$_6$) δ: 2.5 (2H, m), 3.45 (2H, m), 3.8 (2H, m), 4.6–4.7 (4H, m), 5.28 (1H, d, J=5 Hz), 5.3 (2H, m), 5.95 (2H, m), 6.50 (1H, d, J=10 Hz), 6.90 (1H, s), 7.2–7.6 (14H, m), 8.5 (1H, s), 8.2–9.8 (5H, m).

(5) Benzhydryl 7-[2-ethoxyimino-2-(5-amino-1,2,4-thiadiazol-3-yl)acetamido]-3-(2-tosyloxyvinyl)-3-cephem-4-carboxylate (syn isomer) (cis isomer).

IR (Nujol): 3300, 1770, 1720, 1670, 1530 cm$^{-1}$

NMR (DMSO-d$_6$) δ: 1.30 (3H, t, J=7 Hz), 2.43 (3H, s), 3.60 (2H, m), 4.23 (2H, q, J=7 Hz), 5.23 (1H, d, J=5 Hz), 5.91 (1H, m), 6.00 (1H, d, J=7 Hz), 6.62 (1H, d, J=7 Hz), 6.84 (1H, s), 7.33 (12H, m), 7.84 (2H, d, J=8 Hz), 8.12 (2H, br. s), 9.58 (1H, d, J=9 Hz).

(6) Benzhydryl 7-[2-ethoxyimino-2-(5-amino-1,2,4-thiadiazol-3-yl)acetamido]-3-(2-tosyloxyvinyl)-3-cephem-4-carboxylate (syn isomer) (trans isomer).

IR (Nujol): 3300, 1780, 1720, 1670, 1530 cm$^{-1}$

NMR (DMSO-d$_6$) δ: 1.26 (3H, t, J=7 Hz), 2.40 (3H, s), 3.70 (2H, m), 4.20 (2H, q, J=7 Hz), 5.21 (1H, d, J=5 Hz), 5.90 (1H, dd, J=5 Hz, 9 Hz), 6.50 (1H, d, J=12 Hz), 6.88 (1H, s), 7.32 (13H, m), 7.80 (2H, d, J=8 Hz), 8.10 (2H, br. s), 9.57 (1H, d, J=9 Hz).

(7) Benzhydryl 7-[2-allyloxyimino-2-(5-amino-1,2,4-thiadiazol-3-yl)acetamido]-3-(2-tosyloxyvinyl)-3-cephem-4-carboxylate (syn isomer) (cis isomer).

IR (Nujol): 3300, 3200, 1770, 1720, 1680, 1530 cm$^{-1}$

NMR (DMSO-d$_6$) δ: 2.38 (3H, s), 3.53 (2H, m), 4.65 (2H, d, J=5 Hz), 5.04–5.57 (2H, m), 5.18 (1H, d, J=5 Hz), 5.67–6.10 (2H, m), 5.95 (1H, d, J=7 Hz), 6.60 (1H, d, J=7 Hz), 6.80 (1H, s), 7.32 (12H, m), 7.80 (2H, d, J=8 Hz), 8.09 (2H, br. s), 9.59 (1H, d, J=9 Hz).

(8) Benzhydryl 7-[2-allyloxyimino-2-(5-amino-1,2,4-thiadiazol-3-yl)acetamido]-3-(2-tosyloxyvinyl)-3-cephem-4-carboxylate (syn isomer) (trans isomer).

IR (Nujol): 1770, 1715, 1670, 1620, 1520 cm$^{-1}$

NMR (DMSO-d$_6$) δ: 2.40 (3H, s), 3.55 and 3.93 (2H, ABq, J=17 Hz), 4.70 (2H, J=4, 5 Hz), 5.1–5.6 (2H, m), 5.23 (1H, d, J=5 Hz), 5.7–6.2 (1H, m), 5.95 (1H, dd, J=5 Hz, 8 Hz), 6.53 (1H, d, J=11 Hz), 6.90 (1H, s), 7.1–7.6 (11H, m), 7.47 (2H, d, J=9 Hz), 7.86 (2H, d, J=9 Hz), 9.67 (1H, d, J=8 Hz).

(9) Benzhydryl 7-[2-tert-butoxycarbonylmethoxyimino-2-(2-formamidothiazol-4-yl)acetamido]-3-(2-tosyloxyvinyl)-3-cephem-4-carboxylate (syn isomer) (cis isomer).

IR (Nujol): 3250, 1780, 1720, 1672 cm$^{-1}$

NMR (DMSO-d$_6$) δ: 1.43 (9H, s), 2.36 (3H, s), 3.8 (2H, m), 4.6 (2H, br. s), 5.23 (1H, d, J=5 Hz), 6.0 (1H, m), 6.0 (1H, d, J=7 Hz), 6.60 (1H, d, J=7 Hz), 6.83 (1H, s), 7.3–8.0 (15H, m), 8.52 (1H, s), 9.60 (1H, d, J=8 Hz).

(10) Benzhydryl 7-[2-methoxyimino-2-(5-amino-1,2,4-thiadiazol-3-yl)acetamido]-3-(2-tosyloxyvinyl)-3-cephem-4-carboxylate (syn isomer) (trans isomer).

mp: 115°–120° C. (dec.)

IR (Nujol): 3300, 3200, 1770, 1720, 1680, 1630, 1595, 1525, 1495 cm$^{-1}$

NMR (DMSO-d$_6$) δ: 2.40 (3H, s), 3.35 (2H, br. s), 3.93 (3H, s), 5.22 (1H, d, J=5 Hz), 5.90 (1H, dd, J=5 Hz, 8 Hz), 6.52 (1H, d, J=12 Hz), 6.88 (1H, s), 7.23 (1H, d, J=12 Hz), 7.33 (10H, br. s), 7.47 (2H, d, J=8 Hz), 7.82 (2H, d, J=8 Hz), 8.10 (2H, br. s), 9.60 (1H, d, J=8 Hz).

Preparation 12

The following compounds were obtained according to a similar manner to that of Preparation 3-1).

(1) Benzhydryl-7-amino-3-[2-(3-pyridyl)thiovinyl]-3-cephem-4-carboxylate (cis isomer).

NMR (DMSO-d$_6$) δ: 3.80 (2H, s), 4.87 (1H, d, J=4 Hz), 5.12 (1H, d, J=4 Hz), 6.60 (2H, dd, J=10 Hz, 16 Hz), 6.92 (1H, s), 7.04–7.84 (11H, m), 8.12–8.72 (3H, broad).

(2) Benzhydryl 7-amino-3-(2-tosyloxyvinyl)-3-cephem-4-carboxylate-1-oxide (trans isomer).

IR (Nujol): 3400, 1765, 1715, 1620, 1580 cm$^{-1}$

NMR (DMSO-d$_6$) δ: 3.45 and 4.28 (2H, Abq, J=18 Hz), 4.82 (1H, dd, J=8 Hz, 5 Hz), 6.63 and 7.20 (2H, dd, J=12 Hz), 6.87 (1H, s), 7.10–7.57 (10H, m).

(3) Benzhydryl 7-amino-3-{2-[1-(2-N,N-dimethylaminoethyl)-1H-tetrazol-5-yl]thiovinyl}-3-cephem-4-carboxylate (trans isomer).

PREPARATION 13

The following compounds were obtained according to a similar manner to that of Preparation 5-1).

(1) Benzhydryl 7-[2-allyloxyimino-2-(5-amino-1,2,4-thiadiazol-3-yl)acetamido]-3-(2-tosyloxyvinyl)-3-cephem-4-carboxylate-1-oxide (syn isomer) (trans isomer).

NMR (DMSO-d$_6$) δ: 2.43 (3H, s), 3.60 and 4.15 (2H, ABq, J=18 Hz), 4.71 (2H, d, J=5 Hz), 5.07 (1H, d, J=5 Hz), 5.10–5.60 (2H, m), 5.98 (1H, dd, J=5 Hz, 8 Hz), 5.80–6.3 (1H, m), 6.76 (1H, d, J=12 Hz), 6.95 (1H, s), 7.1–7.7 (13H, m), 7.91 (2H, d, J=9 Hz), 9.10 (1H, d, J=9 Hz).

(2) Benzhydryl 7-[2-allyloxyimino-2-(5-amino-1,2,4-thiadiazol-3-yl)acetamido]-3-[2-(3pyridyl)thiovinyl]-3-cephem-4-carboxylate (syn isomer) (cis isomer).

NMR (DMSO-d$_6$) δ: 3.85 (2H, broad), 4.70 (2H, d, J=5 Hz), 5.30 (1H, d, J=5 Hz), 5.10–5.57 (2H, m), 5.80–6.13 (2H, m), 6.63 (2H, s), 6.93 (1H, s), 7.17–7.67 (10H, m), 7.67–8.67 (4H, m), 9.70 (1H, d, J=8 Hz).

(3) Benzhydryl 7-[3-hydroxy-2-(2-tritylaminothiazol-4-yl)-propionamido]-3-[2-(3-pyridyl)thiovinyl]-3-cephem-4-carboxylate (trans isomer).

IR (Nujol): 3350, 1770, 1710, 1670, 1650, 1620, 1570, 1520 cm$^{-1}$

NMR (DMSO-d$_6$) δ: 3.30–4.05 (5H, m), 4.95 (1H, d, J=5 Hz,) 5.85 (1H, m), 6.20 (1H, s), 6.53 (1H, d, J=16 Hz), 7.00 (1H, s), 7.15–7.50 (26H, m), 7.70–8.65 (5H, m).

(4) Benzhydryl 7-[2-methoxyimino-2-(5-amino-1,2,4-thiadiazol-3-yl)acetamido]-3-[2-(3-pyridyl)thiovinyl]-3-cephem-4-carboxylate (syn isomer) (cis isomer).

IR (Nujol): 3300, 3150, 1780, 1730, 1680, 1620, 1530 cm$^{-1}$

NMR (DMSO-d$_6$) δ: 3.83 (2H, m), 3.92 (3H, s), 5.28 (1H, d, J=5 Hz), 5.95 (1H, dd, J=5 Hz, 8 Hz), 6.32 (1H, d, J=10 Hz), 6.68 (1H, d, J=10 Hz), 6.90 (1H, s), 7.15–7.60 (10H, m), 7.65–8.70 (6H, m), 9.60 (1H, d, J=8 Hz).

(5) Benzhydryl 7-[2-allyloxyimino-2-(5-amino-1,2,4-thiadiazol-3-yl)acetamido]-3-[2-(3-pyridyl)thiovinyl]-3-cephem-4-carboxylate (syn isomer) (trans isomer).

NMR (DMSO-d$_6$) δ: 3.95, 4.19 (2H, ABq, J=18 Hz), 4.66 (2H, d, J=5 Hz), 5.1–5.6 (2H, m), 5.23 (1H, d, J=5 Hz), 5.91 (1H, dd, J=5 Hz, 8 Hz), 6.8–7.7 (13H, m), 6.92 (1H, s), 7.87 (1H, dd, J=2 Hz, 8 Hz), 8.11 (2H, br. s), 8.55 (2H, m), 9.65 (1H, d, J=8 Hz).

(6) Benzhydryl 7-[2-ethoxyimino-2-(5-amino-1,2,4-thiadiazol-3-yl)acetamido]-3-(2-tosyloxyvinyl)-3-cephem-4-carboxylate-1-oxide (syn isomer) (cis isomer).

IR (Nujol): 3320, 3150, 1800, 1720, 1660, 1520 cm$^{-1}$

NMR (DMSO-d$_6$) δ: 1.30 (3H, t, J=7 Hz), 2.39 (3H, s), 3.83 (2H, m), 4.23 (2H, q, J=7 Hz), 5.05 (1H, d, J=5 Hz), 6.06 (1H, m), 6.16 (1H, d, J=7 Hz), 6.67 (1H, d, J=7 Hz), 6.86 (1H, s), 7.33 (12H, m), 7.85 (2H, d, J=8 Hz), 8.95 (1H, d, J=9 Hz).

(7) Benzhydryl 7-[2-ethoxyimino-2-(5-amino-1,2,4-thiadiazol-3-yl)acetamido]-3-(2-tosyloxyvinyl)-3-cephem-4-carboxylate-1-oxide (syn isomer) (trans isomer).

NMR (DMSO-d$_6$) δ: 1.33 (3H, t, J=7 Hz), 3.67 (2H, m), 4.26 (2H, q, J=7 Hz), 5.10 (1H, d, J=5 Hz), 6.07 (1H, dd, J=5 Hz, 9 Hz), 6.77 (1H, d, J=12 Hz), 6.95 (1H, s), 7.38 (13H, m), 7.88 (2H, d, J=7 Hz), 9.05 (1H, d, J=9 Hz).

(8) Benzhydryl 7-[2-allyloxyimino-2-(5-amino-1,2,4-thiadiazol-3-yl)acetamido]-3-(2-tosyloxyvinyl)-3-cephem-4-carboxylate-1-oxide (syn isomer) (cis isomer).

NMR (DMSO-d$_6$) δ: 2.36 (3H, s), 3.80 (2H, m), 4.68 (2H, d, J=5 Hz), 4.95–5.53 (3H, m), 5.70–6.30 (2H, m), 6.15 (1H, d, J=7 Hz), 6.65 (1H, d, J=7 Hz), 6.84 (1H, s), 7.34 (12H, m), 7.83 (2H, d, J=8 Hz), 9.02 (1H, d, J=8 Hz).

(9) Benzhydryl 7-[2-allyloxyimino-2-(5-amino-1,2,4-thiadiazol-3-yl)acetamido]-3-(2-tosyloxyvinyl)-3-cephem-4-carboxylate-1-oxide (syn isomer) (trans isomer).

NMR (DMSO-d$_6$) δ: 2.43 (3H, s), 3.60 and 4.15 (2H, ABq, J=19 Hz), 4.71 (2H, d, J=5 Hz), 5.07 (1H, d, J=5 Hz), 5.1–5.6 (2H, m), 5.99 (1H, dd, J=5 Hz, 8 Hz), 5.8–6.3 (1H, m), 6.76 (1H, d, J=12 Hz), 6.95 (1H, s), 7.1–7.7 (13H, m), 7.91 (2H, d, J=9 Hz), 9.10 (1H, d, J=9 Hz).

(10) Benzhydryl 7-[2-allyloxyimino-2-(5-amino-1,2,4-thiadiazol-3-yl)acetamido]-3-{2-[1-(2-N,N-dimethylaminoethyl)-1H-tetrazol-5-yl]thiovinyl}-3-cephem-4-carboxylate (syn isomer) (trans isomer).

IR (Nujol): 3250, 1770, 1715, 1640, 1520 cm$^{-1}$

NMR (DMSO-d$_6$) δ: 2.20 (6H, s), 3.30–4.00 (4H, m), 4.67 (2H, d, J=5 Hz), 5.15–5.50 (3H, m), 5.70–6.15 (1H, m), 6.70–7.10 (3H, m), 7.33 (10H, m), 9.67 (1H, d, J=8 Hz).

(11) Benzhydryl 7-[2-methoxyimino-2-(5-amino-1,2,4-thiadiazol-3-yl)acetamido]-3-(2-tosyloxyvinyl)-3-cephem-4-carboxylate-1-oxide (syn isomer) (trans isomer).

mp: 135°–140° C. (dec.)

IR (Nujol): 3300, 3150, 3050, 1790, 1720, 1675, 1625, 1595, 1520, 1495 cm$^{-1}$ NMR (DMSO-d$_6$) δ: 2.40 (3H, s), 3.72 and 4.35 (2H, ABq, J=15 Hz), 3.93 (3H, s), 5.07 (1H, d, J=5 Hz), 6.05 (1H, dd, J=5 Hz, 8 Hz), 680 (1H, d, J=12 Hz), 6.93 (1H, s), 7.27 (1H, d, J=12 Hz), 7.20–7.60 (10H+2H), 7.50 (2H, d, J=8 Hz), 7.85 (2H, d, J=8 Hz), 9.10 (1H, d, J=8 Hz).

(12) Benzhydryl 7-[2-tert-butoxycarbonylmethoxyimino-2-(2-formamidothiazol-4-yl)acetamido]-3-(2-tosyloxyvinyl)-3-cephem-4-carboxylate-1-oxide (syn isomer) (cis isomer).

IR (Nujol): 3300, 1790, 1720, 1675 cm$^{-1}$

NMR (DMSO-d$_6$) δ: 1.43 (9H, s), 2.38 (3H, s), 3.8 (2H, m), 4.67 (2H, br. s), 5.12 (1H, d, J=5 Hz), 6.1 (1H, m), 6.1–6.8 (2H, m), 6.90 (1H, s), 7.6–8.0 (15H, m), 8.55 (1H, s), 8.9 (1H, d, J=8 Hz).

Preparation 14

The following compounds were obtained according to a similar manner to that of Preparation 6-1).

(1) 7-[2-Allyloxyimino-2-(5-amino-1,2,4-thiadiazol-3-yl)acetamido]-3-[2-(1,3,4-thiadiazol-2-yl)thiovinyl]-3-cephem-4-carboxylic acid (syn isomer) (trans isomer).

IR (Nujol): 3300, 1760, 1670, 1620, 1520 cm$^{-1}$

NMR (DMSO-d$_6$) δ: 2.0 (1H, s), 3.6–4.16 (2H, m), 4.72 (2H, s), 5.22 (1H, d, J=5 Hz), 4.84–5.56 (3H, m), 5.84 (1H, dd, J=8 Hz, 5 Hz), 7.22 (2H, s), 9.6 (1H, s).

(2) 7-[2-Allyloxyimino-2-(5-amino-1,2,4-thiadiazol-3-yl)acetamido]-3-[2-(3-pyridyl)thiovinyl]-3-cephem-4-carboxylic acid (syn isomer) (cis isomer).

IR (Nujol): 3300, 1770, 1670, 1610, 1525 cm$^{-1}$

NMR (DMSO-d$_6$) δ: 3.92 (2H, s), 4.73 (2H, d, J=5 Hz), 5.27 (1H, d, J=5 Hz), 5.10–5.60 (2H, m), 5.77–6.07 (2H, m), 6.75 (2H, ABq, J=10 Hz, 14 Hz), 7.30–8.73 (4H, m), 9.65 (1H, d, J=8 Hz).

(3) 7-[2-Methoxyimino-2-(5-amino-1,2,4-thiadiazol-3-yl)acetamido]3-[2-(3-pyridyl)thiovinyl]-3-cephem-4-carboxylic acid (syn isomer) (cis isomer).

IR (Nujol): 3300, 3170, 1770, 1670, 1615, 1520 cm$^{-1}$

NMR (DMSO-d$_6$) δ: 3.93 (2H, ABq, J=18 Hz), 3.96 (3H, s), 5.27 (1H, d, J=5 Hz), 5.87 (1H, dd, J=5 Hz, 8 Hz), 6.63 (1H, d, J=11 Hz), 6.85 (1H, d, J=11 Hz), 7.33–7.67 (4H, m), 8.13 (2H, br. s), 9.67 (1H, d, J=8 Hz).

(4) 7-[2-Allyloxyimino-2-(5-amino-1,2,4-thiadiazol-3-yl)acetamido]-3-{2-[1-(2-N,N-dimethylaminoethyl)-1H-tetrazol-5-yl]thiovinyl}-3-cephem-4-carboxylic acid (syn isomer) (trans isomer).

IR (Nujol): 3300, 3150, 2650, 2400, 1765, 1695, 1670, 1600, 1520 cm$^{-1}$

NMR (Dcl-D$_2$O) δ: 3.05 (6H, m), 3.50–4.20 (4H, m), 4.70–5.05 (4H, m), 5.20–5.70 (2H, m), 6.15 (1H, d, J=16 Hz), 7.23 (1H, d, J=16 Hz).

(5) 7[2-Allyloxyimino-2-(5-amino-1,2,4-thiadiazol-3-yl)acetamido]-3-[2-(3,4-tetramethylenepyridazin-6-yl)thiovinyl]-3-cephem-4-carboxylic acid (syn isomer) (trans isomer).

IR (Nujol): 3200, 1770, 1670, 1620, 1560, 1520 cm$^{-1}$

NMR (DMSO-d$_6$) δ: 1.78 (4H, m), 2.50–3.20 (4H, m), 3.83 (2H, ABq, J=18 Hz), 4.67 (2H, d, J=5 Hz), 5.25 (1H, d, J=5 Hz), 5.28 (2H, m), 5.80 (1H, dd, J=5 Hz, 8 Hz), 5.87 (1H, m), 7.25 (1H, dd, J=15 Hz), 7.48 (1H, s), 8.10 (2H, broad s), 9.60 (1H, d, J=8 Hz).

(6) 7-[2-Allyloxyimino-2-(5-amino-1,2,4-thiadiazol-3-yl)acetamido]-3-[2-(3-pyridyl)thiovinyl]-3-cephem-4-carboxylic acid (syn isomer) (trans isomer).

IR (Nujol): 3150, 1765, 1670, 1520 cm$^{-1}$

NMR (DMSO-d$_6$) δ: 3.85 (2H, m), 4.70 (2H, d, J=5 Hz), 5.20 (1H, d, J=5 Hz), 5.2–5.6 (2H, m), 5.83 (1H, dd, J=5 Hz, 8 Hz), 5.8–6.3 (1H, m), 7.43 (1H, dd, J=5 Hz, 8 Hz), 7.93 (1H, dd, J=2 Hz, 8 Hz), 8.13 (2H, br. s), 8.60 (2H, m), 9.61 (1H, d, J=8 Hz).

(7) 7-[2-Ethoxyimino-2-(5-amino-1,2,4-thiadiazol-3-yl)acetamido]-3-(2-tosyloxyvinyl)-3-cephem-4-carboxylic acid (syn isomer) (cis isomer).

IR (Nujol): 3300, 3200, 1770, 1760, 1620, 1520 cm$^{-1}$,

NMR (DMSO-d$_6$) δ: 1.27 (3H, t, J=7 Hz), 2.43 (3H, s), 3.59 (2H, m), 4.18 (2H, q, J=7 Hz), 5.13 (1H, d, J=5 Hz, 5.81 (1H, dd, J=5 Hz, 8 Hz), 6.07 (1H, d, J=7 Hz), 6.67 (1H, d, J=7 Hz), 7.48 (2H, d, J=9 Hz), 7.87 (2H, d, J=9 Hz), 8.06 (2H, br. s), 9.48 (1H, d, J=8 Hz).

(8) 7[2-Ethoxyimino-2-(5-amino-1,2,4-thiadiazol-3-yl)acetamido]-3-(2-tosyloxyvinyl)-3-cephem-4-carboxylic acid (syn isomer) (trans isomer).

IR (Nujol): 3300, 3200, 1770, 1670, 1620, 1520 cm$^{-1}$

NMR (DMSO-d$_6$) δ: 1.22 (3H, t, J=7 Hz), 2.40 (3H, s), 3.65 (2H, m), 4.15 (2H, q, J=7 Hz), 5.12 (1H, d, J=5 Hz), 5.77 (1H, dd, J=5 Hz, 9 Hz), 6.60 (1H, d, J=12 Hz), 7.15 (1H, d, J=12 Hz), 7.45 (2H, d, J=8 Hz), 7.82 (2H, d, J=8 Hz), 8.04 (2H, br. s), 9.49 (1H, d, J=9 Hz).

(9) 7-[2-Allyloxyimino-2-(5-amino-1,2,4-thiadiazol-3-yl)acetamido]-3-(2-tosyloxyvinyl)-3-cephem-4-carboxylic acid (syn isomer) (trans isomer).

IR (Nujol): 3300, 3200, 1770, 1670, 1620, 1590, 1520 cm$^{-1}$

NMR (DMSO-d$_6$) δ: 2.41 (3H, s), 3.66 (2H, m), 4.67 (2H, d, J=4 Hz), 5.15 (1H, d, J=5 Hz), 5.2–5.6 (2H, m), 5.80 (1H, dd, J=5 Hz, 8 Hz), 6.60 (1H, d, J=11 Hz), 7.20 (1H, d, J=11 Hz), 7.47 (2H, d, J=8 Hz), 7.87 (2H, d, J=8 Hz), 8.10 (2H, br. s), 9.55 (1H, d, J=8 Hz).

(10) 7-[3-hydroxy-2-(2-aminothiazol-4-yl)propionamido-3-[2-(3-pyridyl)thiovinyl]-3-cephem-4-carboxylic acid (trans isomer).

IR (Nujol): 3250, 3150, 1770, 1660, 1600, 1520 cm$^{-1}$

NMR (DMSO-d$_6$) δ: 3.30–4.00 (5H, m), 5.03 (1H, d, J=5 Hz), 5.60 (1H, dd, J=5 Hz, 8 Hz), 6.30 (1H, br. s), 6.33 (1H, d, J=16 Hz), 6.90 (2H, s), 7.20–8.85 (6H, m).

(11)7-[2-Carboxymethoxyimino-2-(2-aminothiazol-4-yl)acetamido]-3-(2-tosyloxyvinyl)-3-cephem-4-carboxylic acid (syn isomer) (cis isomer).

IR (Nujol): 3300, 1775, 1705, 1650 (br.)

NMR (DMSO-d$_6$) δ: 2.46 (3H, s), 3.70 (2H, m), 4.66 (2H, br. s), 5.20 (1H, d, J=5 Hz), 5.85 (1H, m), 6.15 (1H, d, J=7 Hz), 6.70 (1H, d, J=7 Hz), 7.56, 7.93 (2H, ABq, J=8 Hz), 9.52 (1H, d, J=8 Hz).

(12) 7-[2-Methoxyimino-2-(5-amino-1,2,4-thiadiazol-3-yl)acetamido]-3-(2-tosyloxyvinyl)-3-cephem-4-carboxylic acid (syn isomer) (trans isomer).

mp: 145°–150° C. (dec.)

IR (Nujol): 3400, 3300, 3190, 2550, 1770, 1670, 1625, 1595, 1525 cm$^{-1}$

NMR (DMSO-d$_6$) δ: 2.43 (3H, s), 3.60 and 3.80 (2H, ABq, J=18 Hz), 3.93 (3H, s), 5.17 (1H, d, J=5 Hz), 5.83 (1H, dd, J=5 Hz, 8 Hz), 6.65 (1H, d, J=12 Hz), 7.18 (1H, d, J=12 Hz), 7.52 (2H, d, J=8 Hz), 7.88 (1H, d, J=8 Hz), 8.12 (2H, br. s), 9.58 (1H, d, J=8 Hz).

Preparation 15

The following compounds were obtained according to a similar manner to that of Preparation 7-1).

(1) Benzhydryl 7-[3-hydroxy-2-(2-tritylaminothiazol-4-yl)propionamido]-3-[2-(1-methyl-3-pyridinio)thiovinyl]-3-cephem-4-carboxylate iodide (trans isomer).

IR (Nujol): 3300, 3150, 1770, 1710, 1670, 1620, 1570, 1530 cm$^{-1}$

NMR (DMSO-$d_6$) δ: 3.30–3.90 (5H, m), 4.30 (3H, s), 5.20 (1H, d, J=5 Hz), 5.80 (1H, m), 6.33 (1H, s), 6.62 (1H, d, J=16 Hz), 7.10–7.67 (27H, m), 8.00–9.00 (3H, m), 9.17 (1H, br. s).

(2) Benzhydryl 7-[2-allyloxyimino-2-(5-amino-1,2,4-thiadiazol-3-yl)acetamido]-3-{2-[1-(4-methylpiperazin-1-ylcarbonylmethyl)-3-pyridinio]thiovinyl}-3-cephem-4-carboxylate iodide (syn isomer) (trans isomer).

IR (Nujol): 3350 (broad), 1780, 1710, 1670, 1620 cm$^{-1}$

NMR (DMSO-$d_6$) δ: 2.70–2.87 (8H, m), 3.23–3.63 (7H, m), 4.67 (2H, d, J=5 Hz), 5.07–5.53 (4H, m), 5.70–6.20 (3H, m), 6.97 (1H, s), 7.07–7.57 (10H, m), 7.90–9.43 (4H, m), 9.67 (1H, d, J=8 Hz).

(3) Benzhydryl 7-[2-allyloxyimino-2-1,2,4-thiadiazol-3-yl)acetamido]-3-[2-{1-[3-(4-methylpiperazin-1-yl)propyl]-3-pyridinio)thiovinyl]-3-cephem-4-carboxylate iodide (syn isomer) (trans isomer).

Preparation 16

To a solution of benzhydryl 7-[2-ethoxyimino-2-(5-amino-1,2,4-thiadiazol-3-yl)acetamido]-3-ethynyl-3-cephem-4-carboxylate (syn isomer) (294 mg) in a mixture of acetonitrile (2 ml) and water (1 ml) was added 3-mercapto-1-methylpyridinium chloride (97 mg) at room temperature. The reaction mixture was stirred for one hour at the same temperature and then evaporated to dryness in vacuo to give benzhydryl 7-[2-ethoxyimino-2-(5-amino-1,2,4-thiadiazol-3-yl)acetamido]-3-[2-(1-methyl-3-pyridinio)thiovinyl]-3-cephem-4-carboxylate chloride (syn isomer) (cis isomer) (360 mg).

mp: 140°–145° C. (dec.)

IR (Nujol): 3350, 1780, 1720, 1675, 1525 cm$^{-1}$.

Preparation 17

(1) To a mixture of 1-(3-aminopropyl)-3-mercaptopyridinium chloride hydrochloride (2.8 g) and diisopropylethylamine (0.5 ml) in N,N-dimethylformamide (30 ml) was added benzhydryl 7-[2-allyloxyimino-2-(2-formamidothiazol-4-yl)acetamido]-3-(2-tosyloxyvinyl)-3-cephem-4-carboxylate (syn isomer) (trans isomer) (3.0 g). The reaction mixture was stirred at ambient temperature for 4 hours and poured into ethylacetate (250 ml). The resulting precipitates were collected by filtration, wahsed with ethyl acetate and dried under reduced pressure to give benzhydryl 7-[2-allyloxyimino-2-(2-formamidothiazol-4-yl)acetamido]-3-{2-[1-(3-aminopropyl)-3-pyridinio]thiovinyl}-3-cephem-4-carboxylate chloride hydrochloride (syn isomer) (trans isomer) (3.5 g).

IR (Nujol): 1770, 1705, 1660, 1610 cm$^{-1}$

NMR (DMSO-$d_6$) δ: 2.50 (2H, m), 3.0 (2H, m), 3.98 (2H, br. s), 4.80 (2H, m), 5.33 (1H, d, J=5 Hz), 5.30 (2H, m), 5.95 (1H, dd, J=5 Hz, 8 Hz), 7.0 (1H, s), 7.2–7.7 (13H, m), 8.5 (1H, s), 8.9–9.6 (5H, m).

(2) The following compound was obtained according to a similar manner to that of Preparation 17-1).

Benzhydryl 7-[2-allyloxyimino-2-(2-formamidothiazol-4-yl)acetamido]-3-{2-[1-(3-N,N-dimethylaminopropyl)-3-pyridinio]thiovinyl}-3-cephem-4-carboxylate-1-oxide chloride hydrochloride (syn isomer) (cis isomer).

IR (Nujol): 1780, 1710, 1660, 1630 cm$^{-1}$

NMR (DMSO-$d_6$) δ: 2.7 (2H, m), 2.90 (6H, s), 3.1 (2H, m), 4.2 (2H, m), 4.8 (4H, m), 5.2 (1H, d, J=5 Hz), 5.3 (2H, m), 6.0 (2H, m), 6.95 (1H, s), 7.0–7.6 (13H, m), 8.0–9.4 (5H, m).

Preparation 18

(1) To a solution of benzhydryl 7-[2-allyloxyimino-2-(2-formamidothiazol-4-yl)acetamido]-3-{2-[1-(3-aminopropyl)-3-pyridinio]thiovinyl}-3-cephem-4-carboxylate chloride hydrochloride (syn isomer) (trans isomer) (3.5 g) in methanol (70 ml) was added conc. hydrochloric acid (1.90 ml). The mixture was stirred at ambient temperature for 3.5 hours and poured into ethyl acetate. The resulting precipitates were collected by filtration and washed with ethyl acetate to give benzhydryl 7-[2-allyloxyimino-2-(2-aminothiazol-4-yl)acetamido]-3-{2-[1-(3-aminopropyl)-3-pyridinio]thiovinyl}-3-cephem-4-carboxylate chloride dihydrochloride, (syn isomer) (trans isomer) (1.4 g).

NMR (DMSO-$d_6$) δ: 2.50 (2H, m), 2.9 (2H, m), 3.45 (2H, m), 4.85 (2H, m), 5.26 (1H, d, J=5 Hz), 5.2 (2H, m), 5.9 (2H, m), 6.95 (1H, s), 7.4 (12H, m), 7.6 (1H, s), 8.1–8.7 (3H, m), 8.9–9.6 (3H, m).

(2) The following compound was obtained according to a similar manner to that of Preparation 18-1).

Benzhydryl 7-[2-tert-butoxycarbonylmethoxyimino-2-(2-aminothiazol-4-yl)acetamido]-3-(2-tosyloxyvinyl)-3-cephem-4-carboxylate (syn isomer) (cis isomer).

IR (Nujol): 3300, 1780, 1718, 1672, 1630 cm$^{-1}$

NMR (DMSO-$d_6$) δ: 1.43 (9H, s), 2.40 (3H, s), 3.65 (2H, m), 4.60 (2H, broad s), 5.23 (1H, d, J=5 Hz), 6.0 (1H, m), 6.04 (1H, d, J=7 Hz), 6.67 (1H, d, J=7 Hz), 6.85 (1H, s), 7.3–8.0 (15H, m), 9.52 (1H, d, J=8 Hz).

Preparation 19

A suspension of 7-[2-ethoxyimino-2-(5-amino-1,2,4-thiadiazol-3-yl)acetamido]-3-[2-(1-methyl-3-pyridinio)-thiovinyl]-3-cephem-4-carboxylate (syn isomer) (trans isomer) (5.5 g) in water (300 ml) was adjusted to pH 6.5 with saturated sodium bicarbonate aqueous solution under cooling at 0°–5° C. and then added sodium borohydride (800 mg) portionwise under simultaneous adjusting to pH 7.0 with 1N-hydrochloric acid. The reaction mixture was stirred for one hour at 0°–5° C. and then adjusted to pH 3.0 with 6N-hydrochloric acid. A small amount of insolble materials was filtered off. The filtrate was subjected to column chromatography on a non-ionic adsorption resin, Diaion HP-20 (1 l). After washing the column with water and 30% aqueous methanol subsequently, fractions which was eluted with 50% aqueous methanol was evaporated and lyophilized to give 7-[2-ethoxyimino-2-(5-amino-1,2,4-thiadiazol-3-yl)acetamido]-3-[2-(1-methyl-1,2,5,6-tetrahydropyrid-3-yl)thiovinyl]-3-cephem-4-carboxylic acid (syn isomer) (trans isomer) (30 g).

mp: 160°–165° C. (dec.)

IR (Nujol): 3300, 1760, 1670, 1600, 1520 cm$^{-1}$

NMR (DMSO-$d_6$) δ: 1.33 (3H, t, J=7 Hz), 2.60 (3H, s), 3.1–2.8 (2H, m), 3.47 (4H, br. s), 3.77 (2H, br. s), 4.27 (2H, q, J=7 Hz), 5.17 (1H, d, J=5 Hz), 5.80 (1H, 2d, J=8 Hz, J=5 Hz), 6.13 (1H, broad s), 6.57 (1H, d, J=15 Hz), 7.10 (1H, d, J=15 Hz), 8.17 (2H, br. s), 9.56 (1H, d, J=8 Hz).

Preparation 20

(1)

(1) A mixture of 3-benzoylthiopyridine (8.6 g) and N-(2-bromoethyl)phthalimide (12.2 g) was heated for eight hours at 95°–100° C. and triturated in chloroform (100 ml) for 30 minutes at room temperature. The resulting precipitates were collected by filtration, washed with chloroform and dried to give 1-(2-phthalimidoethyl)-3-benzoylthiopyridinium bromide (8.3 g).

IR (Nujol): 1770, 1710, 1690, 1620, 1590, 1580 cm$^{-1}$.

(2) The following compound was obtained according to a similar manner to that of Preparation 20-1)-(1)

1-(3-Phthalimidopropyl)-3-benzoylthiopyridinium bromide.

IR (Nujol): 1760, 1695, 1610, 1440, 1390 cm$^{-1}$.

(2)

(1) A suspension of 1-(2-phthalimidoethyl)-3-benzoylthiopyridinium bromide (40 g) in 6N hydrochloric acid (510 ml) was heated under reflux for 10 hours and cooled to room temperature. The resulting precipitates were filtered off and washed with water. The filtrate and the washings were combined and washed with chloroform. The separated aqueous layer was evaporated to dryness under reduced pressure. The residue was triturated in acetone, and the resulting precipites were collected by filtlation and dried in vacuo to give 1-(2-aminoethyl)-3-mercaptopyridinium chloride hydrochloride (18.1 g).

mp: 180°–182° C.

IR (Nujol): 2300–2200, 1610, 1560, 1450, 1315 cm$^{-1}$

NMR (D$_2$O) δ: 3.73 (2H, t, J=7 Hz), 4.93 (2H, t, J=7 Hz), 7.91 (1H, dd, J=5 Hz, 8 Hz), 8.51 (1H, dd, J=2 Hz, 8 Hz), 8.67 (1H, dd, J=2 Hz, 5 Hz), 8.87 (1H, s).

(2) The following compound was obtained according to a similar manner to that of Preparation 20-2)-(1).

1-(3-Aminopropyl)-3-mercaptopyridinium chloride hydrochloride.

NMR (D$_2$O) δ: 2.47 (2H, m), 3.23 (2H, t, J=7 Hz), 4.71 (2H, t, J=7 Hz), 8.00 (1H, m), 8.50 (1H, dd, J=2 Hz), 8.70 (1H, dd, J=2 Hz, 5 Hz), 8.91 (1H, s).

(3) To a solution of 1-(2-aminoethyl)-3-mercaptopyridinium chloride hydrochloride (9.0 g) in water (45 ml) was added a solution of iodine (4.1 g) in ethanol (90 ml) at room temperature. The reaction mixture was evaporated to dryness under reduced pressure and the residue was triturated in ethanol. The resulting precipitates were collected by filtration, washed with ethanol and dried in vacuo to give 3,3'-[1,1'-di(2-aminoethyl)-pyridinium chloride]disulfide dihydrochloride (10.0 g).

NMR (D$_2$O) δ: 3.77 (4H, t, J=7 Hz), 5.03 (4H, t, J=7 Hz), 8.17 (2H, dd, J=5 Hz, 8 Hz), 8.75–9.05 (4H, m), 9.27 (2H, br. s).

(4) A mixture of 3,3'-[1,1'-di(2-aminoethyl)-pyridinium chloride]disulfide dihydrochloride (9.75 g), sodium bicarbonate (3.62 g), formic acid (9.91 g), 35% aqueous formaldehyde (8.13 g) and water (4.3 ml) was heated for 1.5 hours at 100° C. and cooled. To the mixture was added 6N hydrochloric acid (7.0 ml), and formic acid and any excess formaldehyde were evaporated. The residue was diluted with water (50 ml) and subjected to column chromatography on non-ionic adsorption resin "HP-20" (320 ml). The elution was carried out with water. The fractions containing the desired compound were combined and evaporated to dryness to give 3,3'-[1,1'-di(2-N,N-dimethylaminoethyl)pyridinium chloride]disulfide dihydrochloride (8.7 g) as oil.

NMR (D$_2$O) δ: 3.03 (12H, s), 3.95 (4H, t, J=7 Hz), 5.15 (4H, t, J=7 Hz), 8.13 (2H, m), 8.70–8.93 (4H, m), 9.27 (2H, br. s).

(5)

(1) To a solution of 3,3'-[1,1'-di(3-N,N-dimethylaminopropyl)pyridinium chloride]disulfide dihydrochloride (16.0 g) in water (80 ml) and methanol (160 ml) was added triphenylphosphine (7.84 g) at ambient temperature. The mixture was stirred at the same temperature for an hour and concentrated under reduced pressure to remove methanol. The residual aqueous solution was washed with chloroform twice and evaporated in vacuo. To the residue was added ethanol and the ethanol solution was concentrated to give 1-(3-N,N-dimethylaminopropyl)-3-mercaptopyridinium chloride hydrochloride (16.0 g).

NMR (D$_2$O) δ: 2.60 (2H, m), 3.0 (6H, s), 3.35 (2H, m), 3.70 (2H, m), 7.86 (1H, m), 8.60 (2H, m), 8.93 (1H, br. s).

(2) The following compound was obtained according to a similar manner to that of Preparation 20-5)-(1).

1-(2-N,N-Dimethylaminoethyl)-3-mercaptopyridinium chloride hydrochloride.

IR (Nujol): 2680–2550, 1620, 1555, 1440, 1405 cm$^{-1}$

NMR (D$_2$O) δ: 3.07 (6H, s), 3.93 (2H, t, J=7 Hz), 5.13 (2H, t, J=7 Hz), 8.08 (1H, dd, J=5 Hz, 8 Hz), 8.72 (1H, dd, J=2 Hz, 8 Hz), 8.90 (1H, dd, J=2 Hz, 5 Hz), 9.07 (1H, br. s).

(6) 3,3'-Dipyridyl disulfide (7.0 g) and 3-N,N-dimethylaminopropyl chloride hydrochloride (10.05 g) was stirred at 130° to 140° C. for 4 hours to give 3,3'-[1,1'-di(3-N,N-dimethylaminopropyl)pyridinium chloride]-disulfide dihydrochloride (17.0 g).

NMR (D$_2$O) δ: 2.6 (4H, m), 2.93 (12H, s), 3.33 (4H, m), 4.76 (4H, t, J=7 Hz), 8.08 (2H, m), 8.80 (4H, m), 9.20 (2H, br. s).

Preparation 21

(1) To a stirred mixture of triphenylphosphine (40.7 g) and zinc powder (18.5 g) in methylene chloride (250 ml) was added carbontetrabromide (45 g) at 20°–30° C. Benzhydryl 7-phenylacetamido-3-formyl-2-cephem-4-carboxylate (10 g) was added portionwise to the above reaction mixture, and the mixture was stirred for 30 minutes at room temperature. Triphenylphosphine oxide was solidified by addition of ethyl acetate to the reaction mixture and removed by filtration. The residue left by removal of the solvents was chromatographed on silica gel. The elution with chloroform containing ethyl acetate (10%) gave benzhydryl 7-phenylacetamido-3-(2,2-dibromovinyl)-2-cephem-4-carboxylate (4.4 g).

IR (Nujol): 3200, 1790, 1730, 1650, 1520 cm$^{-1}$

NMR (DMSO-d$_6$) δ: 3.55 (2H, s), 5.13 (1H, d, J=5 Hz), 5.45 (1H, dd, J=5, 8 Hz), 5.65 (1H, s), 6.90 (1H, s), 7.1 (1H, s), 7.2–7.7 (16H), 9.2 (1H, d, J=8 Hz).

(2) To a suspension of phosphorus pentachloride (13.74 g) in dichloromethane (150 ml) was dropwise added pyridine (5.34 ml) at −15° to −10° C. under stirring which was continued at the same temperature for 30 minutes. To the above mixture was added benzhydryl 7-phenylacetamido-3-(2,2-dibromovinyl)-2-cephem-4-carboxylate (29.4 g) at −5° C. After the reaction mixture was stirred at −5° for 1.5 hours, methanol (26.62 ml) was dropwise added to the reaction mixture under cooling at −20° and the mixture was stirred at −20° C. to −5° C. for 1.5 hours. Then water (30 ml) was added to the reaction mixture under ice-cooling. After the reaction mixture was stirred for an hour at the same temperature, diisopropylether (100 ml) was added to the reaction mixture at 0° C. The resultant precipitates were collected by filtration and washed in turn with water and diisopropyl ether to give benzhydryl 7-amino-3-(2,2-dibromovinyl)-2-cephem-4-carboxylate hydrochloride (25.23 g).

IR (Nujol): 1775, 1730, 1580 cm$^{-1}$

NMR (DMSO-d$_6$, δ): 5.03 (1H, d, J=4 Hz), 5.20 (1H, d, J=4 Hz), 5.70 (1H, s), 6.83 (1H, s), 7.08 (1H, s), 7.13–7.63 (10H, m).

(3) To a mixture of water (100 ml), ethyl acetate (100 ml) and tetrahydrofuran (100 ml) was added benzhydryl 7-amino-3-(2,2-dibromovinyl)-2-cephem-4-carboxylate hydrochloride (5 g), and the mixture was adjusted to pH 7.0 with saturated aqueous sodium bicarbonate. The organic layer was separated, washed with brine, dried over magnesium sulfate. The solution was evaporated in vacuo, and the residue was dissolved in dichloromethane (50 ml). On the other hand, acetic anhydride (3.2 ml) and formic acid (1.29 ml) was stirred at 40° to 45° C. for 30 minutes.

This solution was added to the dichloromethane solution obtained above under ice-cooling and the resultant mixture was stirred at the same temperature for an hour. After water and ethyl acetate were added to the reaction mixture, the organic layer was separated and washed with saturated aqueous sodium bicarbonate and brine, dried over magnesium sulfate. The solution was evaporated in vacuo to give benzhydryl 7-formamido-3-(2,2-dibromovinyl)-2-cephem-4-carboxylate (4.20 g).

IR (Nujol): 1780, 1725, 1655 cm$^{-1}$

NMR (DMSO-d$_6$) δ: 5.20 (1H, d, J=4 Hz), 5.70 (1H, dd, J=8 Hz, 4 Hz), 7.70 (1H, s), 6.90 (1H, s), 7.12 (1H, s), 7.23–7.73 (10H, m), 8.20 (1H, s), 9.17 (1H, d, J=8 Hz).

(4) To a solution of benzhydryl 7-formamido-3-(2,2-dibromovinyl)-2-cephem-4-carboxylate (4.2 g) in ethyl acetate (42 ml) was added a solution of m-chloroperbenzoic acid (1.72 g) in ethyl acetate at −20° to −10° C. and the resultant mixture was stirred at −10° C. for 45 minutes. The precipitates were collected by filtration to give benzhydryl 7-formamido-3-(2,2-dibromovinyl)-3-cephem-4-carboxylate-1-oxide (1.9 g).

IR (Nujol): 3270, 1790, 1710, 1655 cm$^{-1}$

NMR (DMSO-d$_6$) δ: 3.67–4.17 (2H, m), 5.05 (1H, d, J=5 Hz), 6.12 (1H, dd, J=8 Hz, 5 Hz), 6.98 (1H, s), 7.2–7.77 (10H, m), 8.20 (1H, s), 8.47 (1H, d, J=8 Hz).

(5) To a solution of benzhydryl 7-formamido-3-(2,2-dibromovinyl)-3-cephem-4-carboxylate-1-oxide (1.8 g) was added n-butyl lithium (7.27 ml of 1.65M solution in hexane) at −65° to −60° C. under a nitrogen atmosphere. After the resultant mixture was stirred at the same temperature for 30 minutes, ethyl acetate (50 ml) was added to the reaction mixture. The reaction mixture was warmed to −20° C., and hydrolysed with 10% hydrochloric acid. The organic layer was separated and washed with water and brine, dried over magnesium sulfate. The solution was evaporated in vacuo to give benzhydryl 7-formamido-3-ethynyl-3-cephem-4-carboxylate-1-oxide (1.30 g).

IR (Nujol): 1790, 1720, 1660 cm$^{-1}$

NMR (DMSO-d$_6$) δ: 3.67–4.08 (2H, m), 4.72 (1H, s), 5.02 (1H, d, J=5 Hz), 6.03 (1H, dd, J=8 Hz, 5 Hz), 6.97 (1H, s), 7.12–7.78 (10H, m), 8.15 (1H, s), 8.48 (1H, d, J=8 Hz).

(6) To a solution of benzhydryl 7-formamido-3-ethynyl-3-cephem-4-carboxylate-1-oxide (12 g) in N,N-dimethylformamide (96 ml) was added phosphorus trichloride (0.48 ml) at −20° C. and the resultant mixture was stirred at −20° C. to −10° C. for 10 minutes. After water and ethyl acetate were added to the reaction mixture, the separated organic layer was washed with water and brine, dried over magnesium sulfate. The solution was evaporated in vacuo to give benzhydryl 7-formamido-3-ethynyl-3-cephem-4-carboxylate (1.15 g).

IR (Nujol): 1780, 1720, 1670 cm$^{-1}$

NMR (DMSO-d$_6$) δ: 3.58–4.12 (2H, m), 4.73 (1H, s), 5.25 (1H, d, J=5 Hz), 5.92 (1H, dd, J=8 Hz, 5 Hz), 6.97 (1H, s), 7.08–7.75 (10H, m), 8.17 (1H, s), 9.13 (1H, d, J=8 Hz).

(7) To a solution of benzhydryl 7-formamido-3-ethynyl-3-cephem-4-carboxylate (3 g) in a mixture of methanol (30 ml) and tetrahydrofuran (15 ml) was added phosphorus oxychloride (2.75 g) under ice-cooling. After the resultant mixture was stirred at room temperature for 30 minutes, the reaction mixture was added to diisopropyl ether (300 ml), and the precipitates were collected by filtration. The precipitates were added to a mixture of water (50 ml) and ethyl acetate (50 ml) under stirring, and the mixture was adjusted to pH 7.0 with saturated aqueous sodium bicarbonate. To the separated aqueous layer was added ethyl acetate (50 ml), and the mixture was acidified to pH 3.0 with 10% hydrochloric acid and the resultant precipitates were collected by filtration to give benzhydryl 7-amino-3-ethynyl-3-cephem-4-carboxylate (2.03 g).

IR (Nujol): 1775, 1720 cm$^{-1}$

NMR (DMSO-d$_6$) δ: 3.5–3.9 (2H, m), 4.60 (1H, s), 4.88 (1H, d, J=5 Hz), 5.08 (1H, d, J=5 Hz), 6.92 (1H, s), 7.08–7.73 (10H, m).

(8) Benzhydryl 7-[2-ethoxyimino-2-(5-amino-1,2,4-thiadiazol-3-yl)acetamido]-3-ethynyl-3-cephem-4-carboxylate (syn isomer) (2.0 g) was obtained by reacting benzhydryl 7-amino-3-ethynyl-3-cephem-4-carboxylate (1.50 g) with 2-[2-ethoxyimino-2-(5-amino-1,2,4-thiadiazol-3-yl)]acetyl chloride hydrochloride (syn isomer) (1.25 g) in a conventional manner.

IR (Nujol): 1780, 1720, 1650 cm$^{-1}$

NMR (DMSO-d$_6$) δ: 1.25 (3H, t, J=7 Hz), 3.33–3.95 (2H, m), 4.18 (2H, q, J=7 Hz), 4.65 (1H, s), 5.23 (1H, d, J=5 Hz), 6.97 (1H, dd, J=8 Hz, 5 Hz), 6.93 (1H, s), 7.07–7.70 (10H, m), 9.60 (1H, d, J=8 Hz).

(9) 7-[2-Ethoxyimino-2-(5-amino-1,2,4-thiadiazol-3-yl)acetamido]-3-ethynyl-3-cephem-4-carboxylic acid (syn isomer) (0.35 g) was obtained by subjecting benzhydryl 7-[2-ethoxyimino-2-(5-amino-1,2,4-thiadiazol-3-yl)acetamido]-3-ethynyl-3-cephem-4-carboxylate (1.9 g) to elimination reaction of the carboxy protective group in a conventional manner.

IR (Nujol): 3260, 1775, 1670

NMR (DMSO-d$_6$) δ: 1.25 (3H, t, J=7 Hz), 3.38–3.88 (2H, m), 4.18 (2H, q, J=7 Hz), 4.45 (1H, s), 4.85 (1H, dd, J=8 Hz, 5 Hz), 5.18 (1H, d, J=5 Hz), 8.10 (2H, broad s), 9.55 (1H, d, J=8 Hz).

PREPARATION OF THE OBJECT COMPOUNDS OF THE PRESENT INVENTION

Example 1

To a solution of 7-[2-ethoxyimino-2-(5-amino-1,2,4-thiadiazol-3-yl)acetamido]-3-[2-(3-pyridyl)thiovinyl]-3-cephem-4-carboxylic acid (syn isomer) (trans isomer) (1.2 g) in a mixture of water (5 ml), tetrahydrofuran (70 ml) and dimethyl formamide (10 ml) was added methyl iodide (0.7 ml). After being stirred at ambient temperature for 15–20 hours, the mixture was concentrated and poured into ethylacetate (300 ml). The resulting precipitates were collected by filtration and washed with diisopropyl ether. This precipitates were chromatographed on macroporous non-ionic resin "Diaion-HP 20" and eluted with 20% aqueous solution of isopropyl alcohol. The fractions containing object compound were concentrated and lyophilized to give 7-[2-ethoxyimino-2-(5-amino-1,2,4-thiadiazol-3-yl)acetamido]-3-[2-(1-methyl-3-pyridinio)thiovinyl]-3-cephem-4-carboxylate (syn isomer) (trans isomer) (0.45 g).

IR (Nujol): 3300 (broad), 1760, 1660, 1600, 1520 cm$^{-1}$

NMR (DMSO-d$_6$) δ: 1.30 (2H, t, J=7 Hz), 3.1–3.8 (2H, m), 4.28 (3H, q, J=7 Hz), 4.40 (3H, s), 5.12 (1H, d, J=4 Hz), 5.71 (1H, dd, J=4, 8 Hz), 6.53 and 7.50 (2H, 2xd, J=16 Hz), 7.8–9.20 (5H, m), 9.50 (1H, d, J=8 Hz).

Example 2

(1) A mixture of 7-[2-ethoxyimino-2-(5-amino-1,2,4-thiadiazol-3-yl)acetamido]-3-[2-(2-pyridyl)thiovinyl]-3-cephem-4-carboxylic acid (syn isomer) (trans isomer) (1.5 g), dimetylformamide (15 ml) and methyliodide (1.5 ml) was shaken for six days at ambient temperature in a stainless-steel bomb. The reaction mixture was poured into ethyl acetate. The resultant, precipitate was collected by filtration and washed with ethyl acetate and dr d to give 7-[2-ethoxyimino-2-(5-amino-1,2,4-thiadiazol-3-yl)acetamido]-3-[2-(1-methyl-2-pyridinio)-thiovinyl]-3-cephem-4-carboxylate hydriodide (syn isomer) (trans isomer) (2.0 g).

IR (Nujol): 3400, 3250, 1780, 1650–1680, 1620 cm$^{-1}$

NMR (DMSO-d$_6$) δ: 1.38 (3H, t, J=7 Hz), 3.87 (2H, ABq, J=18 Hz), 4.23 (3H, s), 4.3 (2H, m), 5.3 (1H, d, J=5 Hz), 5.88 (1H, dd, J=8 Hz, 5 Hz), 7.07 (1H, J=16 Hz), 7.48 (1H, d, J=16 Hz), 7.8–8.7 (3H, m), 9.0 (1H, d, J=5 Hz), 9.67 (1H, d, J=8 Hz)

(2) 7-[2-Ethoxyimino-2-(5-amino-1,2,4-thiadiazol-3-yl)acetamido]-3-[2-(1-methyl-2-pyridinio)thiovinyl]-3-cephem-4-carboxylate hydriodide (syn isomer) (trans isomer) (2.0 g) was dissolved in a saturated aqueous solution of sodium bicarbonate. After being adjusted to pH 5.5 with 10% aqueous hydrochloric acid, the solution was filtered to remove undissolved compound. The filtrate was purified by column chromatography on macroporous non-ionic adsorption resin "Diaion HP-20" and eluted with 30% aqueous solution of isopropyl alcohol. The fractions, containing the desired compound, were combined, concentrated in vacuo and lyophilized to give 7-[2-ethoxyimino-2-(5-amino-1,2,4-thiadiazol-3-yl)acetamido]-3-[2-(1-methyl-2-pyridinio)-thiovinyl]-3-cephem-4-carboxylate (syn isomer) (trans isomer) (0.8 g).

IR (Nujol): 3300, 3200, 1760, 1650, 1600 cm$^{-1}$

NMR (DMSO-d$_6$) δ: 1.28 (3H, m), 3.55 (2H, ABq, J=18 Hz), 4.20 (3H, s), 4.15 (2H, m), 5.15 (1H, d, J=5 Hz), 5.70 (1H, dd, J=8 Hz, 5 Hz), 6.65 (1H, d, J=16 Hz), 7.80 (1H, d, J=16 Hz), 8.00–8.50 (5H, m), 8.90 (1H, b-s), 9.55 (1H, d, J=8 Hz).

Example 3

The following compounds were obtained according to a similar manner to that of Example 1 or Example 2.

(1) 7-[2-Methoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3400–3100 (broad), 1760, 1660, 1600, 1520 cm$^{-1}$

NMR (D$_2$O-DCl) δ: 3.90 (2H, d), 4.12 (3H, s), 4.50 (3H, s), 5.32 (1H, d, J=4 Hz), 5.80 (1H, d, J=4 Hz), 7.05 and 7.40 (2H, 2xd, J=16 Hz), 7.18 (1H, s), 7.8–9.0 (4H, m).

(2) Trifluoroacetic acid salt of 7-amino-3-[2-(1-methyl-2-pyridinio)thiovinyl]-3-cephem-4-carboxylate hydriodide (trans isomer) (3.9 g).

IR (Nujol): 2550–2450, 1760, 1660, 1640, 1600 cm$^{-1}$

NMR (DMSO-d$_6$) δ: 3.75–4.3 (2H, m), 4.21 (3H, s), 5.0–5.47 (2H, m), 7.13 (1H, d, J=16 Hz), 7.3–8.3 (6H, m), 9.0 (1H, d, J=5 Hz).

(3) Trifluoroacetic acid salt of 7-amino-3-[2-(1-methyl-3-pyridinio)thiovinyl]-3-cephem-4-carboxylate hydriodide (trans isomer).

IR (Nujol): 3350, 2500–2600, 1780, 1670, 1620 cm$^{-1}$

NMR (DMSO-d$_6$) δ: 3.95 (2H, ABq, J=18 Hz), 4.30 (3H, s), 5.1–5.3 (2H, m), 6.5–7.3 (2H, m), 8.0–8.9 (5H, m), 9.13 (1H, broad s).

(4) Trifluoroacetic acid salt of 7-amino-3-[2-(4-methyl-2-pyrazinio)thiovinyl]-3-cephem-4-carboxylate hydriodide (trans isomer).

IR (Nujol): 3300, 1800, 1670 cm$^{-1}$.

(5) 7-[2-Methoxyimino-2-(2-aminothiazol-4-yl)acetamido]-3-[2-(1-methyl-2-pyridinio)thiovinyl]-3-cephem-4-carboxylate (syn isomer)(trans isomer).

IR (Nujol): 3300, 1765, 1670, 1611, 1562, 1533 cm$^{-1}$.

(6) 7-[2-Methoxyimino-2-(2-aminothiazol-4-yl)acetamido]-3-[2-(4-methyl-2-pyrazinio)thiovinyl]-3-cephem-4-carboxylate (syn isomer)(trans isomer).

IR (Nujol): 3300, 1765 (br.), 1660, 1600 cm$^{-1}$.

(7) 7-[2-Methoxyimino-2-(2-tritylaminothiazol-4-yl)acetamido]-3-[2-(1-methyl-2-pyridinio)thiovinyl]-3-cephem-4-carboxylate. (syn isomer)(trans isomer).

IR (Nujol): 3250, 1780, 1672, 1595 cm$^{-1}$.

(8) 7-[2-Methoxyimino-2-(2-tert-pentyloxycarbonylaminothiazol-4-yl)acetamido]-3-[2-(4-methyl-2-pyrazinio)thiovinyl]-3-cephem-4-carboxylate (syn isomer)(trans isomer).

IR (Nujol): 3350, 1762, 1700, 1660, 1530 cm$^{-1}$.

(9) 7-[2-Ethoxyimino-2-(5-amino-1,2,4-thiadiazol-3-yl)acetamido]-3-[2-(1,3-dimethyl-2-pyrimidinio)thiovinyl]-3-cephem-4-carboxylate iodide (syn isomer)(trans isomer)

IR (Nujol): 3350, 1770, 1663, 1605 cm$^{-1}$

NMR (D$_2$O) δ: 1.40 (3H, t, J=7 Hz), 3.80 (2H, br. s), 3.91 (3H, s), 4.14 (3H, s), 4.50 (2H, q, J=7 Hz), 5.30 (1H, d, J=5 Hz), 5.80 (1H, d, J=5 Hz), 6.73, 7.27 (2H, ABq, J=16 Hz), 7.77 (1H, m), 9.03 (2H, m).

(10) 7-[2-Ethoxyimino-2-(5-amino-1,2,4-thiadiazol-3-yl)acetamido]-3-[2-(4-methyl-2-pyrazinio)thiovinyl]-3-cephem-4-carboxylate (syn isomer)(trans isomer).

IR (Nujol): 3350, 1760 (br.), 1665, 1607 cm$^{-1}$

NMR (DMSO-d$_6$) δ: 1.20 (3H, t, J=7 Hz), 3.90 (2H, br.s), 4.13 (2H, q, J=7 Hz), 4.26 (3H, s), 5.17 (1H, d, J=5 Hz), 5.77 (1H, dd, J=5 Hz, 8 Hz), 7.22 (2H, br.s), 8.03 (2H, br. s), 8.80 (1H, br.s), 9.20 (2H, br.s), 9.50 (1H, d, J=8 Hz).

(11) 7-[2-Methoxyimino-2-(5-amino-1,2,4-thiadiazol-3-yl)acetamido]-3-[2-(1-methyl-2-pyridinio)thiovinyl]-3-cephem-4-carboxylate (syn isomer) (trans isomer).

IR (Nujol): 3250–3350, 1770, 1660, 1620, 1560, 1530 cm$^{-1}$.

(12) Trifluoroacetic acid salt of 7-amino-3-[2-(1-methyl-3-pyridinio)thiovinyl]-3-cephem-4-carboxylate hydriodide (cis isomer).

IR (Nujol): 3400 (broad), 2350 (broad), 1800, 1670, 1620, 1540–1520 cm$^{-1}$.

(13) 7-[2-Ethoxyimino-2-(5-amino-1,2,4-thiadiazol-3-yl)acetamido]-3-[2-(1-ethyl-3-pyridinio)thiovinyl]-3-cephem-4-carboxylate (syn isomer) (trans isomer).

IR (Nujol): 3300 (broad), 1770, 1675, 1600, 1520 cm$^{-1}$

NMR (DMSO-d$_6$) δ: 1.05-1.80 (4H, m, J=7 Hz), 3.13-3.8 (2H, m), 4.23 (3H, q, J=7 Hz), 4.68 (3H, q, J=7 Hz), 5.12 (1H, d, J=5 Hz), 5.68 (1H, d-d, J=5, 8 Hz), 6.64 (1H, d, J=16 Hz), 7.49 (1H, d, J=16 Hz), 7.80-9.30 (6H, m), 9.50 (1H, d, J=8 Hz).

(14) 7-[2-Ethoxyimino-2-(5-amino-1,2,4-thiadiazol-3-yl)acetamido]-3-[2-(1-methyl-3-pyridinio)thiovinyl]-3-cephem-4-carboxylate (syn isomer) (cis isomer).

IR (Nujol): 3300 (broad), 1760, 1665, 1600, 1520 cm$^{-1}$.

(15) 7-[2-Carboxymethoxyimino-2-(5-amino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3300 (broad), 1765, 1670, 1615, 1560, 1525 cm$^{-1}$.

(16) 7-[2-Allyloxyimino-2-(5-amino-1,2,4-thiadiazol-3-yl)acetamido]-3-[2-(1-methyl-3-pyridinio)thiovinyl]-3-cephem-4-carboxylate (syn isomer) (trans isomer).

IR (Nujol): 3300, 1760, 1670, 1620, 1600, 1530 cm$^{-1}$.

(17) 7-[2-(Tert-butoxycarbonylmethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3200-3300, 2400-2600, 1770, 1715, 1680, 1630 cm$^{-1}$

NMR (DMSO-d$_6$) δ: 1.50 (9H, s), 3.20-4.10 (2H, m), 4.43 (3H, s), 4.70 (2H, s), 5.30 (1H, d, J=5 Hz), 5.83 (1H, dd, J=5 Hz, 8 Hz), 7.00 (1H, s), 7.30 (2H, broad s), 8-9.00 (6H, m), 9.27 (1H, broad s), 9.77 (1H, d, J=8 Hz).

(18) 7-[2-Carboxymethoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1765, 1670, 1620 cm$^{-1}$

NMR (DMSO-d$_6$) δ: 3.50-4.10 (2H, m), 4.30 (3H, s), 4.63 (2H, broad s), 5.23 (1H, d, J=5 Hz), 5.90 (1H, dd, J=5 Hz, 8 Hz), 6.87 (1H, s), 6.95 (1H, d, J=15 Hz), 7.15 (2H, broad s), 7.47 (1H, d, J=15 Hz), 7.90-8.90 (3H, m), 9.13 (1H, broad s), 9.80 (1H, d, J=8 Hz).

(19) 7-[2-(3-Carboxy-2-propenyloxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535 cm$^{-1}$

NMR (DMSO-d$_6$/D$_2$O) δ: 3.57-4.20 (2H, m), 4.37 (3H, s), 4.57-4.93 (2H, m), 5.10 (1H, d, J=5 Hz), 5.60 (1H, dd, J=5 Hz, 8 Hz), 5.98 (1H, d, J=16 Hz), 6.51 (1H, d, J=16 Hz), 7.48 (1H, d, J=16 Hz), 6.78 (1H, s), 7.76-9.17 (4H, m), 9.67 (1H, d, J=8 Hz).

(20) 7-[2-(1-Methyl-2-pyridiniomethoxyimino)-2-(2-aminothiazol-4-yl)acetamido]-3-[2-(1-methyl-3-pyridinio)thiovinyl]-3-cephem-4-carboxylate iodide (syn isomer) (trans isomer).

IR (Nujol): 3250, 1760, 1665, 1615 cm$^{-1}$

NMR (D$_2$O) δ: 7.9-9.00 (8H, m), 7.17 (1H, d, J=16 Hz), 7.10 (1H, s), 6.67 (1H, d, J=16 Hz), 5.90 (1H, d, J=5 Hz), 5.75 (2H, s), 5.34 (1H, d, J=5 Hz), 4.45 (6H, s), 3.5-4.25 (2H, m).

(21) 7-[2-(2-Pyridylmethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1620, 1590 cm$^{-1}$

NMR (DMSO-d$_6$) δ: 3.7-4.20 (2H, m), 4.47 (3H, s), 5.15 (1H, d, J=5 Hz), 5.25 (2H, s), 5.72 (1H, dd, J=5 Hz, 8 Hz), 6.48 (1H, d, J=14 Hz), 6.80 (1H, s), 7.1-9.0 (11H, m), 9.90 (1H, d, J=8 Hz).

(22) 7-[2-(3-Carboxypropoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535 cm$^{-1}$

NMR (DMSO-d$_6$/D$_2$O) δ: 1.5-2.73 (4H, m), 3.3-4.27 (4H, m), 4.37 (3H, s), 5.08 (1H, d, J=5 Hz), 5.63 (1H, dd, J=5 Hz, 8 Hz), 6.50 (1H, d, J=16 Hz), 7.48 (1H, d, J=16 Hz), 6.74 (1H, s), 7.76-9.13 (4H, m), 9.55 (1H, d, J=8 Hz).

(23) 7-[2-(1-Carboxypropoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1590 cm$^{-1}$

NMR (DMSO-d$_6$) δ: 1.08 (3H, t, J=7 Hz), 1.62-2.24 (2H, m), 3.2-3.9 (2H, m), 4.42 (3H, s), 4.47 (1H, t, J=6 Hz), 5.15 (1H, d, J=5 Hz), 5.77 (1H, dd, J=8 Hz, 5 Hz), 6.47 (1H, d, J=16 Hz), 6.87 (1H, s), 7.0 (1H, d, J=16 Hz), 7.02-9.3 (4H, m).

(24) 7-[2-Allyloxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1530 cm$^{-1}$

NMR (DMSO-d$_6$/D$_2$O) δ: 3.33-3.87 (4H, m), 4.37 (3H, s), 4.62 (2H, d, J=5 Hz), 6.50 (1H, d, J=16 Hz), 7.47 (1H, d, J=16 Hz), 6.73 (1H, s), 7.83-9.03 (4H, m), 9.57 (1H, d, J=8 Hz).

(25) 7-[2-(2-Hydroxyethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535, 1500 cm$^{-1}$

NMR (DMSO-d$_6$/D$_2$O) δ: 3.20-3.83 (2H, m), 4.35 (3H, s).

(26) 7-[2-Ethoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1665, 1600, 1535 cm$^{-1}$

NMR (DMSO-d$_6$/D$_2$O) δ: 1.25 (3H, t, J=7 Hz), 4.13 (2H, ABq, J=7 Hz), 4.37 (3H, s), 5.08 (1H, d, J=5 Hz), 5.65 (1H, dd, J=5 Hz, 8 Hz), 6.48 (1H, d, J=16 Hz), 7.48 (1H, d, J=16 Hz), 7.73-7.93 (4H, m), 9.52 (1H, d, J=8 Hz), 6.73 (1H, s).

(27) 7-[2-(2-Propynyloxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3250, 1760, 1660, 1600, 1530 cm$^{-1}$

NMR (DMSO-d$_6$/D$_2$O) δ: 3.3-3.8 (3H, m), 4.37 (3H, s), 4.7 (2H, s), 5.09 (1H, d, J=5 Hz), 5.63 (1H, dd, J=5 Hz, 8 Hz), 6.53 (1H, d, J=16 Hz), 6.78 (1H, s), 7.50 (1H, d, J=16 Hz), 7.73-7.93 (4H, m), 9.05 (1H, s), 9.52 (1H, d, J=8 Hz).

(28) 7-[2-(Tert-butoxycarbonylmethoxyimino)-2-(2-formamidothiazol-4-yl)acetamido]-3-[2-(1-methyl-3-pyridinio)thiovinyl]-3-cephem-4-carboxylate (syn isomer) (trans isomer).

IR (Nujol): 3200-3400, 1760, 1720-1730, 1690, 1670 cm$^{-1}$

NMR (DMSO-d$_6$) δ: 1.50 (9H, s), 3.50-4.20 (2H, m), 4.37 (3H, s), 4.63 (2H, s), 5.27 (1H, d, J=5 Hz), 5.87 (1H, dd, J=5 Hz, 8 Hz), 7.00 (1H, d, J×16 Hz), 7.40 (1H, d, J=16 Hz), 7.45 (1H, s), 7.95-9.10 (4H, m), 8.53 (1H, s), 9.67 (1H, d, J=8 Hz), 12.70 (1H, broad s).

(29) 7-{2-(1-Tert-butoxycarbonyl)propoxyimino]-2-(2-formamidothiazol-4-yl)acetamido]}-3-[2-(1-methyl-3-pyridinio)thiovinyl]-3-cephem-4-carboxylate (syn isomer) (trans isomer).

IR (Nujol): 3250, 1760, 1720, 1680 cm$^{-1}$

NMR (DMSO-d$_6$) δ: 0.98 (3H, t, J=7 Hz), 1.45 (9H, s), 1.52–2.06 (2H, m), 3.67–4.17 (2H, m), 4.37 (3H, s), 4.5 (1H, t, J=6 Hz), 5.28 (1H, d, J=5 Hz), 5.93 (1H, dd, J=8 Hz, 5 Hz), 6.43 (1H, d, J=16 Hz), 7.22 (1H, s), 7.63 (1H, d, J=16 Hz), 7.83–9.33 (4H, m), 8.52 (1H, s), 9.6 (1H, d, J=8 Hz).

(30) 7-[2-(2-Pyridylmethoxyimino)-2-(2-formamidothiazol-4-yl)acetamido]-3-[2-(1-methyl-3-pyridinio)thiovinyl]-3-cephem-4-carboxylate (syn isomer) (trans isomer).

NMR (DMSO-d$_6$) δ: 3.3–4.00 (2H, m), 4.33 (3H, s), 5.13 (1H, d, J=5 Hz), 5.30 (2H, broad s), 5.83 (1H, dd, J=5 Hz, 8 Hz), 6.50 (1H, d, J=15 Hz), 7.20–9.00 (9H, m), 7.43 (1H, s), 8.50 (1H, s), 9.95 (1H, d, J=8 Hz).

(31) 7-[2-(3-Benzhydryloxycarbonyl-2-propenyloxyimino)-2-(2-tritylaminothiazol-4-yl)acetamido]-3-[2-(1-methyl-3-pyridinio)thiovinyl]-3-cephem-4-carboxylate (syn isomer) (trans isomer).

IR (Nujol): 3300, 1780, 1720, 1680, 1600, 1530, 1500 cm$^{-1}$

NMR (DMSO-d$_6$/D$_2$O) δ: 3.7–4.35 (2H, m), 4.40 (3H, s), 4.67–5.00 (2H, m), 5.27 (1H, d, J=5 Hz), 5.83 (1H, m), 6.25 (1H, d, J=16 Hz), 6.67–7.00 (3H, m), 7.33 (26H, m), 8.00–9.20 (5H, m), 9.80 (1H, d, J=8 Hz).

(32) 7-[2-Ethoxyimino-2-(2-tritylaminothiazol-4-yl)acetamido]-3-[2-(1-methyl-3-pyridinio)thiovinyl]-3-cephem-4-carboxylate (syn isomer) (trans isomer).

NMR (DMSO-d$_6$/D$_2$O) δ: 1.20 (3H, t, J=7 Hz), 3.6–4.0 (2H, m), 4.06 (2H, ABq, J=7 Hz), 4.37 (3H, s), 5.15 (1H, d, J=5 Hz), 5.67 (1H, dd, J=5 Hz, 8 Hs), 6.72 (1H, s), 7.17–7.50 (15H, m), 8.43–9.17 (4H, m), 9.51 (1H, d, J=5 Hz).

(33) 7-[2-(2-Propynyloxyimino)-2-(2-tritylaminothiazol-4-yl)acetamido]-3-[2-(1-methyl-3-pyridinio)thiovinyl]-3-cephem-4-carboxylate (syn isomer) (trans isomer).

NMR (DMSO-d$_6$/D$_2$O) δ: 3.4–3.7 (3H, m), 4.37 (3H, s), 5.21 (1H, d, J=5 Hz), 5.73 (1H, dd, J=5 Hz, 8 Hz), 6.78 (1H, s), 7.13–7.50 (15H, m), 9.65 (1H, d, J=8 Hz).

(34) 7-[2-(3-Benzhydryloxycarbonylpropoxyimino)-2-(2-tritylaminothiazol-4-yl)acetamido]-3-[2-(1-methyl-3-pyridinio)thiovinyl]-3-cephem-4-carboxylate (syn isomer) (trans isomer).

IR (Nujol): 3350, 1770, 1720, 1665, 1590, 1520 cm$^{-1}$

NMR (DMSO-d$_6$/D$_2$O) δ: 1.53–2.10 (4H, m), 3.50–3.70 (2H, m), 3.83–4.27 (2H, m), 4.35 (3H, s), 5.17 (1H, d, J=8 Hz), 5.63 (1H, m), 6.78 (1H, s), 6.87 (1H, d, J=15 Hz), 6.90 (1H, s), 7.10–7.50 (26H, m), 7.80–9.17 (4H, m), 9.60 (1H, d, J=8 Hz).

(35) 7-[2-Carboxymethoxyimino-2-(thiazol-4-yl)acetamido]-3-[2-(1-methyl-3-pyridinio)thiovinyl]-3-cephem-4-carboxylate (syn isomer) (trans isomer).

IR (Nujol): 3350, 1760, 1660, 1600 cm$^{-1}$

NMR (D$_2$O-NaHCO$_3$)δ: 3.73 (2H, s), 4.35 (3H, s), 4.50–4.87 (2H, m), 5.32 (1H, d, J=5 Hz), 5.83 (1H, dd, J=5 Hz, 8 Hz), 6.63 (1H, d, J=16 Hz), 7.17 (1H, d, J=16 Hz), 7.80–8.80 (6H, m).

(36) 7-[2-Hydroxy-2-(2-aminothiazol-4-yl)acetamido]-3-[2-(1-methyl-3-pyridinio)thiovinyl]-3-cephem-4-carboxylate (trans isomer).

IR (Nujol): 3300, 1760, 1670, 1600 cm$^{-1}$

NMR (DMSO-d$_6$) δ: 3.42–4.04 (2H, m), 4.43 (3H, s), 5.00 (1H, s), 5.15 (1H, d, J=5 Hz), 5.70 (1H, dd, J=8 Hz, 5 Hz), 6.54 (1H, s), 6.6 (1H, d, J=16 Hz), 7.02 (2H, broad s), 7.53 (1H, d, J=16 Hz), 7.73–9.17 (4H, m).

(37) 7-[2-(1-Carboxy)ethoxyimino-2-(5-amino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3300, 1770, 1665, 1600, 1520 cm$^{-1}$

NMR (DMSO-d$_6$/D$_2$O) δ: 1.51 (3H, d, J=6 Hz), 3.80 (2H, broad s), 4.31 (3H, s), 4.75 (1H, d, J=6 Hz), 5.25 (1H, d, J=4 Hz), 5.85 (1H, d, J=4 Hz), 6.83 (1H, d, J=16 Hz), 7.50 (1H, d, J=16 Hz), 7.6–9.4 (4H, m).

(38) 7-[2-(1-Methyl-1-carboxyethoxyimino)-2-(5-amino-1,2,4-thiadiazol-3-yl)acetamido]-3-[2-(1-methyl-3-pyridinio)thiovinyl]-3-cephem-4-carboxylate (syn isomer) (trans isomer).

IR (Nujol): 3300, 1770, 1670, 1610, 1520 cm$^{-1}$

NMR (D$_2$O-NaHCO$_3$) δ: 1.60 (6H, s), 3.82 (2H, s), 4.42 (3H, s), 5.35 (1H, d, J=4 Hz), 5.90 (1H, d, J=4 Hz), 6.70 (1H, d, J=16 Hz), 7.20 (1H, d, J=16 Hz), 7.5–8.9 (3H, m).

(39) 7-[2-Ethoxyimino-2-(5-amino-1,2,4-thiadiazol-3-yl)acetamido]-3-[2-(1-carboxymethyl-3-pyridinio)thiovinyl]-3-cephem-4-carboxylate (syn isomer) (trans isomer).

IR (Nujol): 3300, 1760, 1640–1680, 1610, 1520 cm$^{-1}$

NMR (DMSO-d$_6$) δ: 1.30 (3H, t, J=5 Hz), 3.33–3.90 (2H, m), 4.25 (2H, q, J=7 Hz), 4.95–5.20 (3H, m), 5.75 (1H, m), 6.60 (1H, d, J=16 Hz), 7.50 (1H, d, J=16 Hz), 8.00–9.00 (4H, m), 9.55 (1H, d, J=8 Hz).

(40) 7-[2-Ethoxyimino-2-(5-amino-1,2,4-thiadiazol-3-yl)acetamido]-3-[2-(2-trimethylammonioethyl)thiovinyl]-3-cephem-4-carboxylate (syn isomer) (trans isomer).

IR (Nujol): 3300, 1760, 1670, 1600, 1520 cm$^{-1}$

NMR (DMSO-d$_6$) δ: 1.25 (3H, t, J=5 Hz), 3.10–4.00 (6H, m), 4.20 (2H, q, J=7 Hz), 5.05 (1H, d, J=5 Hz), 5.60 (1H, m), 6.60 (1H, d, J=16 Hz), 7.03 (1H, d, J=16 Hz), 8.06 (2H, broad s), 9.50 (1H, d, J=8 Hz).

(41) 7-[(4-Carboxy-3-hydroxyisothiazol-5-yl)thioacetamido]-3-[2-(1-methyl-3-pyridinio)thiovinyl]-3-cephem-4-carboxylate (trans isomer).

IR (Nujol): 3300, 1760, 1670 cm$^{-1}$

NMR (DMSO-d$_6$) δ: 3.93 (2H, s), 3.83–4.00 (2H, m), 4.47 (3H, s), 5.27 (1H, d, J=5 Hz), 5.70 (1H, dd, J=8 Hz, 5 Hz), 7.30 (6H, m), 9.50 (1H, d, J=8 Hz).

(42) 7-[2-Methoxyimino-2-(5,6-dihydro-1,4-oxathiin-2-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1500 cm$^{-1}$

NMR (D$_2$O) δ: 3.0–3.23 (2H, m), 3.73 (2H, s), 4.33 (3H, s), 5.22 (1H, d, J=5 Hz), 5.71 (1H, d, J=5 Hz), 5.97 (1H, s), 6.58 (1H, d, J=16 Hz), 7.12 (1H, d, J=16 Hz).

(43) 7-[2-Methoxyimino-2-(1,2,3-thiadiazol-4-yl)acetamido]-3-[2-(1-methyl-3-pyridinio)thiovinyl]-3-cephem-4-carboxylate (syn isomer) (trans isomer).

IR (Nujol): 3200–3350, 1760, 1660, 1600, 1555 cm$^{-1}$

NMR (DMSO-d$_6$/D$_2$O) δ: 3.67 (2H, s), 4.02 (3H, s), 4.37 (3H, s), 5.13 (1H, d, J=5 Hz), 5.80 (1H, dd, J=5 Hz, 8 Hz), 6.50 (1H, d, J=16 Hz), 7.50 (1H, d, J=16 Hz), 7.83–9.10 (4H, m), 9.40 (1H, s), 9.78 (1H, d, J=8 Hz).

(44) 7-[2-Methoxyimino-2-(3-hydroxyphenyl)acetamido]-3-[2-(1-methyl-3-pyridinio)thiovinyl]-3-cephem-4-carboxylate (syn isomer) (trans isomer).

IR (Nujol): 1770, 1650, 1600, 1570, 1500 cm$^{-1}$

NMR (DMSO-d$_6$/D$_2$O) δ: 3.50–4.17 (5H, m), 4.17–4.67 (3H, m), 5.17 (1H, d, J=5 Hz), 5.77 (1H, dd, J=5 Hz, 8 Hz), 6.60 (1H, d, J=16 Hz), 7.53 (1H, d, J=16 Hz), 6.83–7.40 (4H, m), 7.73–8.93 (4H, m).

(45) Trifluoroacetic acid salt of 7-amino-3-[2-(1-methyl-2-pyridinio)thiovinyl]-3-cephem-4-carboxylic acid iodide (cis isomer).

IR (Nujol): 2300–2500, 1780, 1670, 1610, 1560 cm$^{-1}$

NMR (DMSO-d$_6$) δ: 3.85 (2H, ABq, J=17 Hz), 4.20 (3H, s), 5.35 (2H, m), 6.67 (1H, d, J=10 Hz), 6.95–8.50 (4H, m), 9.10 (1H, broad s), 9.67 (2H, broad s).

(46) 7-[2-Methoxyimino-2-(2-aminothiazol-4-yl)acetamido]-3-[2-(1-methyl-2-pyridinio)thiovinyl]-3-cephem-4-carboxylate (syn isomer) (cis isomer).

IR (Nujol): 3400–3100, 1765, 1660, 1610, 1560, 1530 cm$^{-1}$

NMR (DMSO-d$_6$) δ: 3.67 (2H, ABq, J=16 Hz), 3.83 (3H, s), 4.17 (3H, s), 5.12 (1H, d, J=5 Hz), 5.63 (1H, dd, J=5 Hz, 8 Hz), 6.42 (1H, d, J=14 Hz), 6.73 (1H, s), 7.25 (2H, broad s), 7.63 (1H, d, J=14 Hz), 7.9–9.00 (4H, m), 9.57 (1H, d, J=8 Hz).

(47) 7-[(2-Methoxyimino-2-(2-aminothiazol-4-yl)acetamido]-3-[2-(1-methyl-3-pyridinio)thiovinyl-3-cephem-4-carboxylate (syn isomer) (cis isomer).

IR (Nujol): 3300, 1760, 1660, 1600, 1530 cm$^{-1}$

NMR (DMSO-d$_6$) δ: 3.72 (2H, ABq, J=16 Hz), 3.82 (3H, s), 4.33 (3H, s), 5.10 (1H, d, J=5 Hz), 5.65 (1H, dd, J=5 Hz, 8 Hz), 6.38 (1H, d, J=10 Hz), 6.73 (1H, s), 7.22 (1H, d, J=10 Hz), 7.18 (2H, broad s), 7.85–8.90 (3H, m), 9.17 (1H, broad s), 9.50 (1H, d, J=8 Hz).

(48) 7-[2-Methoxyimino-2-(2-tritylaminothiazol-4-yl)acetamido]-3-[2-(1-methyl-3-pyridinio)thiovinyl]-3-cephem-4-carboxylate (syn isomer) (trans isomer).

IR (Nujol): 3300–3400, 1770, 1675, 1620, 1600 cm$^{-1}$

NMR (DMSO-d$_6$) δ: 3.77 (3H, s), 3.80 (2H, m), 4.32 (3H, s), 5.17 (1H, d, J=5 Hz), 5.67 (1H, dd, J=5 Hz, 8 Hz), 6.70 (1H, s), 6.85–7.67 (17H, m), 8.00–9.03 (4H, m), 9.55 (1H, d, J=8 Hz).

(49) 7-[2-Methoxyimino-2-(2-tritylaminothiazol-4-yl)acetamido]-3-[2-(1-methyl-2-pyridinio)thiovinyl]-3-cephem-4-carboxylate (syn isomer) (cis isomer).

IR (Nujol): 3300–3200, 1775, 1680, 1660, 1615, 1600, 1570 cm$^{-1}$

NMR (DMSO-d$_6$) δ: 3.67–3.95 (2H, m), 3.78 (3H, s), 4.20 (3H, s), 5.17 (1H, d, J=5 Hz), 5.70 (1H, dd, J=5 Hz, 8 Hz), 6.70 (1H, s), 6.75 (1H, d, J=10 Hz), 7.00–7.50 (15H, m), 7.67–9.05 (4H, m), 9.52 (1H, d, J=8 Hz).

(50) 7-[2-Methoxyimino-2-(2-tritylaminothiazol-4-yl)acetamido]-3-[2-(1-methyl-3-pyridinio)thiovinyl]-3-cephem-4-carboxylate (syn isomer) (cis isomer).

IR (Nujol): 3350–3250, 1770, 1670, 1620, 1590 cm$^{-1}$

NMR (DMSO-d$_6$) δ: 3.70–4.00 (5H, m), 3.80 (3H, s), 4.30 (3H, s), 5.20 (1H, d, J=5 Hz), 5.70 (1H, dd, J=5 Hz, 8 Hz), 6.70 (1H, s), 6.73 (1H, d, J=11 Hz), 7.00 (1H, d, J=11 Hz), 7.15–7.50 (15H, m), 8.00–9.10 (5H, m), 9.50 (1H, d, J=8 Hz).

(51) 7-[2-(3-Carboxypropoxyimino)-2-(5-amino-1,2,4-thiodiazol-3-yl)acetamido]-3-[2-(1-methyl-3-pyridinio)-thiovinyl]-3-cephem-4-carboxylate (syn isomer) (trans isomer).

IR (Nujol): 3300, 1765, 1665, 1600, 1530 cm$^{-1}$

NMR (DMSO-d$_6$) δ: 1.6–2.7 (4H, m), 3.75 (2H, broad s), 4.0–4.4 (2H, m), 4.40 (3H, s), 5.10 (1H, d, J=4 Hz), 5.72 (1H, dd, J=4, 8 Hz), 6.75 (1H, d, J=16 Hz), 7.44 (1H, d, J=16 Hz), 7.7–9.1 (4H, m), 9.60 (1H, d, J=8 Hz).

(52) 7-[2-Ethoxyimino-2-(5-amino-1,2,4-thiadiazol-3-yl)acetamido]-3-[2-(1-methyl-2-pyridinio)thiovinyl]-3-cephem-4-carboxylate (syn isomer) (cis isomer).

IR (Nujol): 3300, 1765, 1670, 1610, 1560 cm$^{-1}$

NMR (DMSO-d$_6$) δ: 1.27 (3H, t, J=5 Hz), 3.65–4.35 (4H, m), 5.10 (1H, J=5 Hz), 5.68 (1H, dd, J=5 Hz, 8 Hz), 6.42 (1H, d, J=14 Hz), 7.67 (1H, d, J=14 Hz), 6.95–9.00 (6H, m), 9.50 (1H, d, J=8 Hz).

(53) 7-[2-Ethoxyimino-2-(5-phosphonoamino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3200–3400 (broad), 1760, 1672, 1520 cm$^{-1}$

NMR (NaHCO$_3$-D$_2$O) δ: 1.33 (3H, t, J=7 Hz), 3.77 (2H, broad s), 4.35 (3H, s), 4.33 (2H, q, J=7 Hz), 5.30 (1H, d, J=5 Hz), 5.82 (1H, d, J=5 Hz), 6.60 (1H, d, J=15 Hz), 7.17 (1H, d, J=15 Hz), 7.85–8.80 (4H, m).

(54) 7-[2-Ethoxyimino-2-(5-phosphonoamino-1,2,4-thiadiazol-3-yl)acetamido]-3-[2-(1-methyl-2-pyridinio)-thiovinyl]-3-cephem-4-carboxylate (syn isomer) (trans isomer).

IR (Nujol): 3200, 1768, 1673, 1610, 1560, 1508, 1269, 1230 cm$^{-1}$

NMR (NaHCO$_3$-D$_2$O) δ: 1.33 (3H, t, J=7 Hz), 3.83 (2H, broad s), 4.23 (3H, s), 4.38 (2H, q, J=7 Hz), 5.30 (1H, d, J=5 Hz), 5.80 (1H, d, J=5 Hz), 6.60 (1H, d, J=14 Hz), 7.38 (1H, d, J=14 Hz), 7.4–8.8 (4H, m).

EXAMPLE 4

To a ice-cooled solution of benzhydryl 7-tertbutoxycarbonylamino-3-[2-(1-methyl-2-pyridinio)thiovinyl]-3-cephem-4-carboxylate iodide (trans isomer) (5.0 g) in methylenechloride (15 ml) and anisole (20 ml) was dropwise added to trifluoroacetic acid (40 ml). The mixture was stirred under same condition for 2 hours. The reaction mixture was poured into diisopropylether and the resultant precipitate was collected by filtration to give trifluoroacetic acid salt of 7-amino-3-[2-(1-methyl-2-pyridinio)thiovinyl]-3-cephem-4-carboxylate hydriodide (trans isomer) (3.9 g).

IR (Nujol): 2550–2450, 1760, 1660, 1640, 1600 cm$^{-1}$

NMR (DMSO-d$_6$) δ: 3.75–4.3 (2H, m), 4.21 (3H, s), 5.0–5.47 (2H, m), 7.13 (1H, d, J=16 Hz), 7.3–8.3 (6H, m), 9.0 (1H, d, J=5 Hz).

EXAMPLE 5

The following compounds were obtained according to a similar manner to that of Example 4.

(1) 7-[2-Ethoxyimino-2-(5-amino-1,2,4-thiadiazol-3-yl)acetamido]-3-[2-(1-methyl-3-pyridinio)thiovinyl]-3-cephem-4-carboxylate (syn isomer) (trans isomer).

IR (Nujol): 3300 (broad), 1760, 1660, 1600, 1520 cm$^{-1}$.

(2) 7-[2-Methoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3400–3100 (broad), 1760, 1660, 1600, 1520 cm$^{-1}$.

(3) 7-[2-Ethoxyimino-2-(5-amino-1,2,4-thiadiazol-3-yl)acetamido]-3-[2-(1-methyl-2-pyridinio)thiovinyl]-3-cephem-4-carboxylate hydriodide (syn isomer) (trans isomer).

IR (Nujol): 3400, 3250, 1780, 1650–1680, 1620 cm$^{-1}$.

(4) 7-[2-Ethoxyimino-2-(5-amino-1,2,4-thiadiazol-3-yl)acetamido]-3-[2-(1-methyl-2-pyridinio)thiovinyl]-3-cephem-4-carboxylate (syn isomer) (trans isomer).

IR (Nujol): 3300, 3200, 1760, 1650, 1600 cm$^{-1}$.

(5) Trifluoroacetic acid salt of 7-amino-3-[2-(1-methyl-3-pyridinio)thiovinyl]-3-cephem-4-carboxylate hydroiodide (trans isomer).

IR (Nujol): 3350, 2500–2600, 1780, 1670, 1620 cm$^{-1}$

NMR (DMSO-d$_6$) δ: 3.95 (2H, ABq, J=18 Hz), 4.30 (3H, s), 5.1–5.3 (2H, m), 6.5–7.3 (2H, m), 8.0–8.9 (5H, m), 9.13 (1H, broad s).

(6) Trifluoroacetic acid salt of 7-amino-3-[2-(4-methyl-2-pyrazinio)thiovinyl]-3-cephem-4-carboxylate hydriodide (trans isomer).

IR (Nujol): 3300, 1800, 1670 cm$^{-1}$

NMR (D₂O) δ: 3.93 ;1 (2H, br. s), 4.43 (3H, s), 5.18 (1H, d, J=5 Hz), 5.40 (1H, d, J=5 Hz), 7.42 (2H, s), 8.59 (1H, d, J=4 Hz), 9.0 (1H, br. s), 9.13 (1H, br.s).

(7) 7-[2-Methoxyimino-2-(2-aminothiazol-4-yl)acetamido]-3-[2-(1-methyl-2-pyridinio)thiovinyl]-3-cephem-4-carboxylate (syn isomer) (trans isomer).

IR (Nujol): 3300, 1765, 1670, 1611, 1562, 1533 cm⁻¹.

(8) 7-[2-Methoxyimino-2-(2-aminothiazol-4-yl)acetamido]-3-[2-(4-methyl-2-pyrazinio)thiovinyl]-3-cephem-4-carboxylate (syn isomer) (trans isomer).

IR (Nujol): 3300, 1765 (br.), 1660, 1600 cm⁻¹.

(9) 7-[2-Methoxyimino-2-(2-tritylaminothiazol-4-yl)acetamido]-3-[2-(1-methyl-2-pyridinio)thiovinyl]-3-cephem-4-carboxylate (syn isomer) (trans isomer).

IR (Nujol): 3250, 1780, 1672, 1595 cm⁻¹.

(10) 7-[2-Methoxyimino-2-(2-tert-pentyloxycarbonylaminothiazol-4-yl)acetamido]-3-[2-(4-methyl-2-pyrazinio)thiovinyl]-3-cephem-4-carboxylate (syn isomer) (trans isomer).

IR (Nujol): 3350, 1762, 1700, 1660, 1530 cm⁻¹.

(11) 7-[2-Ethoxyimino-2-(5-amino-1,2,4-thiadiazol-3-yl)acetamido]-3-[2-(1,3-dimethyl-2-pyrimidinio)thiovinyl]-3-cephem-4-carboxylate iodide (syn isomer) (trans isomer).

IR (Nujol): 3350, 1770, 1663, 1605 cm⁻¹.

(12) 7-[2-Ethoxyimino-2-(5-amino-1,2,4-thiadiazol-3-yl)acetamido]-3-[2-(4-methyl-2-pyrazinio)thiovinyl]-3-cephem-4-carboxylate (syn isomer) (trans isomer).

IR (Nujol): 3350, 1760 (br.), 1665, 1607 cm⁻¹.

(13) 7-[2-Methoxyimino-2-(5-amino-1,2,4-thiadiazol-3-yl)acetamido]-3-[2-(1-methyl-2-pyridinio)thiovinyl]-3-cephem-4-carboxylate (syn isomer) (trans isomer).

IR (Nujol): 3250–3350, 1770, 1660, 1620, 1560, 1530 cm⁻¹.

(14) Trifluoroacetic acid salt of 7-amino-3-[2-(1-methyl-3-pyridinio)thiovinyl]-3-cephem-4-carboxylate hydriodide (cis isomer).

IR (Nujol): 3400 (broad), 2350 (broad), 1800, 1670, 1620, 1540–1520 l cm⁻¹

NMR (DMSO-d₆) δ: 3.94 (2H, bs), 4.38 (3H, s), 5.15–5.48 (2H, m), 6.97 (2H, d, J=5 Hz), 7.90–9.23 (4H, m).

(15) 7-[2-Ethoxyimino-2-(5-amino-1,2,4-thiadiazol-3-yl)acetamido]-3-[2-(1-ethyl-3-pyridinio)thiovinyl]-3-cephem-4-carboxylate (syn isomer) (trans isomer).

IR (Nujol): 3300 (broad), 1770, 1675, 1600, 1520 cm⁻¹.

(16) 7-[2-Ethoxyimino-2-(5-amino-1,2,4-thiadiazol-3-yl)acetamido]-3-[2-(1-methyl-3-pyridinio)thiovinyl]-3-cephem-4-carboxylate (cis isomer).

IR (Nujol): 3300 (broad), 1760, 1665, 1600, 1520 cm⁻¹.

(17) 7-[2-Carboxymethoxyimino-2-[5-amino-1,2,4-thiadiazol-3-yl)acetamido]-3-[2-(1-methyl-3-pyridinio)thiovinyl]-3-cephem-4-carboxylate (syn isomer) (trans isomer).

IR (Nujol): 3300 (broad), 1765, 1670, 1615, 1560, 1525 cm⁻¹.

(18) 7-[2-Allyloxyimino-2-(5-amino-1,2,4-thiadiazol-3-yl)acetamido]-3-[2-(1-methyl-3-pyridinio)thiovinyl]-3-cephem-4-carboxylate (syn isomer) (trans isomer).

IR (Nujol): 3300, 1760, 1670, 1620, 1600, 1530 cm⁻¹.

(19) 7-[2-(Tert-butoxycarbonylmethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3200–3300, 2400–2600, 1770, 1715, 1680, 1630 cm⁻¹

NMR (DMSO-d₆) δ: 1.50 (9H, s), 3.20–4.10 (2H, m), 4.43 (3H, s), 4.70 (2H, s), 5.30 (1H, d, J=5 Hz), 5.83 (1H, dd, J=5 Hz, 8 Hz), 7.00 (1H, s), 7.30 (2H, broad s), 8–9.00 (6H, m), 9.27 (1H, broad s), 9.77 (1H, d, J=8 Hz).

(20) 7-[2-Carboxymethoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1765, 1670, 1620 cm⁻¹

NMR (DMSO-d₆) δ: 3.50–4.10 (2H, m), 4.30 (3H, s), 4.63 (2H, broad s), 5.23 (1H, d, J=5 Hz), 5.90 (1H, dd, J=5 Hz, 8 Hz), 6.87 (1H, s), 6.95 (1H, d, J=15 Hz), 7.15 (2H, broad s), 7.47 (1H, d, J=15 Hz), 7.90–8.90 (3H, m), 9.13 (1H, broad s), 9.80 (1H, d, J=8 Hz).

(21) 7-[2-(3-Carboxy-2-propenyloxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535 cm⁻¹

NMR (DMSO-d₆/D₂O) δ: 3.57–4.20 (2H, m), 4.37 (3H, s), 4.57–4.93 (2H, m), 5.10 (1H, d, J=5 Hz), 5.60 (1H, dd, J=5 Hz, 8 Hz), 5.98 (1H, d, J=16 Hz), 6.51 (1H, d, J=16 Hz), 7.48 (1H, d, J=16 Hz), 6.78 (1H, s), 7.76–9.17 (4H, m), 9.67 (1H, d, J=8 Hz).

(22) 7-[2-(1-Methyl-2-pyridiniomethoxyimino)-2-(2-aminothiazol-4-yl)acetamido]-3-[2-(1-methyl-3-pyridinio)thiovinyl]-3-cephem-4-carboxylate iodide (syn isomer) (trans isomer).

IR (Nujol): 3250, 1760, 1665, 1615 cm⁻¹

NMR (D₂O) δ: 7.9–9.00 (8H, m), 7.17 (1H, d, J=16 Hz), 7.10 (1H, s), 6.67 (1H, d, J=16 Hz), 5.90 (1H, d, J=5 Hz), 5.75 (2H, s), 5.34 (1H, d, J=5 Hz), 4.45 (6H, s), 3.5–4.25 (2H, m).

(23) 7-[2-(2-Pyridylmethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1620, 1590 cm⁻¹

NMR (DMSO-d₆) δ: 3.7–4.20 (2H, m), 4.47 (3H, s), 5.15 (1H, d, J=5 Hz), 5.25 (2H, s), 5.72 (1H, dd, J=5 Hz, 8 Hz), 6.48 (1H, d, J=14 Hz), 6.80 (1H, s), 7.1–9.0 (11H, m), 9.90 (1H, d, J=8 Hz).

(24) 7-[2-(3-Carboxypropoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535 cm⁻¹

NMR (DMSO-d₆/D₂O) δ: 1.5–2.73 (4H, m), 3.3–4.27 (4H, m), 4.37 (3H, s), 5.08 (1H, d, J=5 Hz), 5.63 (1H, dd, J=5 Hz, 8 Hz), 6.50 (1H, d, J=16 Hz), 7.48 (1H, d, J=16 Hz), 6.74 (1H, s), 7.76–9.13 (4H, m), 9.55 (1H, d, J=8 Hz).

(25) 7-[2-(1-Carboxypropoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1590 cm⁻¹

NMR (DMSO-d₆) δ: 1.08 (3H, t, J=7 Hz), 1.62–2.24 (2H, m), 3.2–3.9 (2H, m), 4.42 (3H, s), 4.47 (1H, t, J=6 Hz), 5.15 (1H, d, J=5 Hz), 5.77 (1H, dd, J=8 Hz, 5 Hz), 6.47 (1H, d, J=16 Hz), 6.87 (1H, s), 7.0 (1H, d, J=16 Hz), 7.02–9.3 (4H, m).

(26) 7-[2-Allyloxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1530 cm⁻¹

NMR (DMSO-d₆/D₂O) δ: 3.33–3.87 (4H, m), 4.37 (3H, s), 4.62 (2H, d, J=5 Hz), 6.50 (1H, d, J=16 Hz), 7.47 (1H, d, J=16 Hz), 6.73 (1H, s), 7.83–9.03 (4H, m), 9.57 (1H, d, J=8 Hz).

(27) 7-[2-(2-Hydroxyethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535, 1500 cm$^{-1}$

NMR (DMSO-d$_6$/D$_2$O) δ: 3.20–3.83 (2H, m), 4.35 (3H, s).

(28) 7-[2-Ethoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1665, 1600, 1535 cm$^{-1}$

NMR (DMSO-d$_6$/D$_2$O) δ: 1.25 (3H, t, J=7 Hz), 4.13 (2H, ABq, J=7 Hz), 4.37 (3H, s), 5.08 (1H, d, J=5 Hz), 5.65 (1H, dd, J=5 Hz, 8 Hz), 6.48 (1H, d, J=16 Hz), 7.48 (1H, d, J=16 Hz), 7.73–7.93 (4H, m), 9.52 (1H, d, J=8 Hz), 6.73 (1H, s).

(29) 7-[2-(2-Propynyloxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3250, 1760, 1660, 1600, 1530 cm$^{-1}$

NMR (DMSO-d$_6$/D$_2$O) δ: 3.3–3.8 (3H, m), 4.37 (3H, s), 4.7 (2H, s), 5.09 (1H, d, J=5 Hz), 5.63 (1H, dd, J=5 Hz, 8 Hz), 6.53 (1H, d, J=16 Hz), 6.78 (1H, s), 7.50 (1H, d, J=16 Hz), 7.73–7.93 (4H, m), 9.05 (1H, s), 9.52 (1H, d, J=8 Hz).

(30) 7-[2-(Tert-butoxycarbonylmethoxyimino)-2-(2-formamidothiazol-4-yl)acetamido]-3-[2-(1-methyl-3-pyridinio)thiovinyl]-3-cephem-4-carboxylate (syn isomer) (trans isomer).

IR (Nujol): 3200–3400, 1760, 1720–1730, 1690, 1670 cm$^{-1}$

NMR (DMSO-d$_6$) δ: 1.50 (9H, s), 3.50–4.20 (2H, m), 4.37 (3H, s), 4.63 (2H, s), 5.27 (1H, d, J=5 Hz), 5.87 (1H, dd, J=5 Hz, 8 Hz), 7.00 (1H, d, J=16 Hz), 7.40 (1H, d, J=16 Hz), 7.45 (1H, s), 7.95–9.10 (4H, m), 8.53 (1H, s), 9.67 (1H, d, J=8 Hz), 12.70 (1H, broad s).

(31) 7-{2-(1-Tert-butoxycarbonyl)propoxyimino]-2-(2-formamidothiazol-4-yl)acetamido]}-3-[2-(1-methyl-3-pyridinio)thiovinyl]-3-cephem-4-carboxylate (syn isomer) (trans isomer).

IR (Nujol): 3250, 1760, 1720, 1680 cm$^{-1}$

NMR (DMSO-d$_6$) δ: 0.98 (3H, t, J=7 Hz), 1.45 (9H, s), 1.52–2.06 (2H, m), 3.67–4.17 (2H, m), 4.37 (3H, s), 4.5 (1H, t, J=6 Hz), 5.28 (1H, d, J=5 Hz), 5.93 (1H, dd, J=8 Hz, 5 Hz), 6.43 (1H, d, J=16 Hz), 7.22 (1H, s), 7.63 (1H, d, J=16 Hz), 7.83–9.33 (4H, m), 8.52 (1H, s), 9.6 (1H, d, J=8 Hz).

(32) 7-[2-(2-Pyridylmethoxyimino)-2-(2-formamidothiazol-4-yl)acetamido]-3-[2-(1-methyl-3-pyridinio)thiovinyl]-3-cephem-4-carboxylate (syn isomer) (trans isomer).

NMR (DMSO-d$_6$) δ: 3.3–4.00 (2H, m), 4.33 (3H, s), 5.13 (1H, d, J=5 Hz), 5.30 (2H, broad s), 5.83 (1H, dd, J=5 Hz, 8 Hz), 6.50 (1H, d, J=15 Hz), 7.20–9.00 (9H, m), 7.43 (1H, s), 8.50 (1H, s), 9.95 (1H, d, J=8 Hz).

(33) 7-[2-(3-Benzhydryloxycarbonyl-2-propenyloxyimino)-2-(2-tritylaminothiazol-4-yl)acetamido]-3-[2-(1-methyl-3-pyridinio)thiovinyl]-3-cephem-4-carboxylate (syn isomer) (trans isomer).

IR (Nujol): 3300, 1780, 1720, 1680, 1600, 1530, 1500 cm$^{-1}$

NMR (DMSO-d$_6$/D$_2$O) δ: 3.7–4.35 (2H, m), 4.40 (3H, s), 4.67–5.00 (2H, m), 5.27 (1H, d, J=5 Hz), 5.83 (1H, m), 6.25 (1H, d, J=16 Hz), 6.67–7.00 (3H, m), 7.33 (26H, m), 8.00–9.20 (5H, m), 9.80 (1H, d, J=8 Hz).

(34) 7-[2-Ethoxyimino-2-(2-tritylaminothiazol-4-yl)acetamido]-3-[2-(1-methyl-3-pyridinio)thiovinyl]-3-cephem-4-carboxylate (syn isomer) (trans isomer).

NMR (DMSO-d$_6$/D$_2$O) δ: 1.20 (3H, t, J=7 Hz), 3.6–4.0 (2H, m), 4.06 (2H, ABq, J=7 Hz), 4.37 (3H, s), 5.15 (1H, d, J=5 Hz), 5.67 (1H, dd, J=5 Hz, 8 Hs), 6.72 (1H, s), 7.17–7.50 (15H, m), 8.43–9.17 (4H, m), 9.51 (1H, d, J=5 Hz).

(35) 7-[2-(2-Propynyloxyimino)-2-(2-tritylaminothiazol-4-yl)acetamido]-3-[2-(1-methyl-3-pyridinio)thiovinyl]-3-cephem-4-carboxylate (syn isomer) (trans isomer).

NMR (DMSO-d$_6$/D$_2$O) δ: 3.4–3.7 (3H, m), 4.37 (3H, s), 5.21 (1H, d, J=5 Hz), 5.73 (1H, dd, J=5 Hz, 8 Hz), 6.78 (1H, s), 7.13–7.50 (15H, m), 9.65 (1H, d, J=8 Hz).

(36) 7-[2-(3-Benzhydryloxycarbonylpropoxyimino)-2-(2-tritylaminothiazol-4-yl)acetamido]-3-[2-(1-methyl-3-pyridinio)thiovinyl]-3-cephem-4-carboxylate (syn isomer) (trans isomer).

IR (Nujol): 3350, 1770, 1720, 1665, 1590, 1520 cm$^{-1}$

NMR (DMSO-d$_6$/D$_2$O) δ: 1.53–2.10 (4H, m), 3.50–3.70 (2H, m), 3.83–4.27 (2H, m), 4.35 (3H, s), 5.17 (1H, d, J=8 Hz), 5.63 (1H, m), 6.78 (1H, s), 6.87 (1H, d, J=15 Hz), 6.90 (1H, s), 7.10–7.50 (26H, m), 7.80–9.17 (4H, m), 9.60 (1H, d, J=8 Hz).

(37) 7-[2-Carboxymethoxyimino-2-(thiazol-4-yl)acetamido]-3-[2-(1-methyl-3-pyridinio)thiovinyl]-3-cephem-4-carboxylate (syn isomer) (trans isomer).

IR (Nujol): 3350, 1760, 1660, 1600 cm$^{-1}$

NMR (D$_2$O-NaHCO$_3$) δ: 3.73 (2H, s), 4.35 (3H, s), 4.50–4.87 (2H, m), 5.32 (1H, d, J=5 Hz), 5.83 (1H, dd, J=5 Hz, 8 Hz), 6.63 (1H, d, J=16 Hz), 7.17 (1H, d, J=16 Hz), 7.80–8.80 (6H, m).

(38) 7-[2-Hydroxy-2-(2-aminothiazol-4-yl)acetamido]-3-[2-(1-methyl-3-pyridinio)thiovinyl]-3-cephem-4-carboxylate (trans isomer).

IR (Nujol): 3300, 1760, 1670, 1600 cm$^{-1}$

NMR (DMSO-d$_6$) δ: 3.42–4.04 (2H, m), 4.43 (3H, s), 5.00 (1H, s), 5.15 (1H, d, J=5 Hz), 5.70 (1H, dd, J=8 Hz, 5 Hz), 6.54 (1H, s), 6.6 (1H, d, J=16 Hz), 7.02 (2H, broad s), 7.53 (1H, d, J=16 Hz), 7.73–9.17 (4H, m).

(39) 7-[2-(1-Carboxy)ethoxyimino-2-(5-amino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3300, 1770, 1665, 1600, 1520 cm$^{-1}$

NMR (DMSO-d$_6$/D$_2$O) δ: 1.51 (3H, d, J=6 Hz), 3.80 (2H, broad s), 4.31 (3H, s), 4.75 (1H, d, J=6 Hz), 5.25 (1H, d, J=4 Hz), 5.85 (1H, d, J=4 Hz), 6.83 (1H, d, J=16 Hz), 7.50 (1H, d, J=16 Hz), 7.6–9.4 (4H, m).

(40) 7-[2-(1-Methyl-1-carboxyethoxyimino)-2-(5-amino-1,2,4-thiadiazol-3-yl)acetamido]-3-[2-(1-methyl-3-pyridinio)thiovinyl]-3-cephem-4-carboxylate (syn isomer) (trans isomer).

IR (Nujol): 3300, 1770, 1670, 1610, 1520 cm$^{-1}$

NMR (D$_2$O-NaHCO$_3$) δ: 1.60 (6H, s), 3.82 (2H, s), 4.42 (3H, s), 5.35 (1H, d, J=4 Hz), 5.90 (1H, d, J=4 Hz), 6.70 (1H, d, J=16 Hz), 7.20 (1H, d, J=16 Hz), 7.5–8.9 (3H, m).

(41) 7-[2-Ethoxyimino-2-(5-amino-1,2,4-thiadiazol-3-yl)acetamido]-3-[2-(1-carboxymethyl-3-pyridinio)thiovinyl]-3-cephem-4-carboxylate (syn isomer) (trans isomer).

IR (Nujol): 3300, 1760, 1640–1680, 1610, 1520 cm$^{-1}$

NMR (DMSO-d$_6$) δ: 1.30 (3H, t, J=5 Hz), 3.33–3.90 (2H, m), 4.25 (2H, q, J=7 Hz), 4.95–5.20 (3H, m), 5.75 (1H, m), 6.60 (1H, d, J=16 Hz), 7.50 (1H, d, J=16 Hz), 8.00–9.00 (4H, m), 9.55 (1H, d, J=8 Hz).

(42) 7-[2-Ethoxyimino-2-(5-amino-1,2,4-thiadiazol-3-yl)acetamido]-3-[2-(2-trimethylammonioethyl)thiovinyl]-3-cephem-4-carboxylate (syn isomer) (trans isomer).

IR (Nujol): 3300, 1760, 1670, 1600, 1520 cm$^{-1}$

NMR (DMSO-d$_6$) δ: 1.25 (3H, t, J=5 Hz), 3.10–4.00 (6H, m), 4.20 (2H, q, J=7 Hz), 5.05 (1H, d, J=5 Hz), 5.60 (1H, m), 6.60 (1H, d, J=16 Hz), 7.03 (1H, d, J=16 Hz), 8.06 (2H, broad s), 9.50 (1H, d, J=8 Hz).

(43) 7-[(4-Carboxy-3-hydroxyisothiazol-5-yl)thioacetamido]-3-[2-(1-methyl-3-pyridinio)thiovinyl]-3-cephem-4-carboxylate (trans isomer).

IR (Nujol): 3300, 1760, 1670 cm$^{-1}$

NMR (DMSO-d$_6$) δ: 3.93 (2H, s), 3.83–4.00 (2H, m), 4.47 (3H, s), 5.27 (1H, d, J=5 Hz), 5.70 (1H, dd, J=8 Hz, 5 Hz), 7.30 (6H, m), 9.50 (1H, d, J=8 Hz).

(44) 7-[2-Methoxyimino-2-(5,6-dihydro-1,4-oxathiin-2-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1500 cm$^{-1}$

NMR (D$_2$O) δ: 3.0–3.23 (2H, m), 3.73 (2H, s), 4.33 (3H, s), 5.22 (1H, d, J=5 Hz), 5.71 (1H, d, J=5 Hz), 5.97 (1H, s), 6.58 (1H, d, J=16 Hz), 7.12 (1H, d, J=16 Hz).

(45) 7-[2-Methoxyimino-2-(1,2,3-thiadiazol-4-yl)acetamido]-3-[2-(1-methyl-3-pyridinio)thiovinyl]-3-cephem-4-carboxylate (syn isomer) (trans isomer).

IR (Nujol): 3200–3350, 1760, 1660, 1600, 1555 cm$^{-1}$

NMR (DMSO-d$_6$/D$_2$O) δ: 3.67 (2H, s), 4.02 (3H, s), 4.37 (3H, s), 5.13 (1H, d, J=5 Hz), 5.80 (1H, dd, J=5 Hz, 8 Hz), 6.50 (1H, d, J=16 Hz), 7.50 (1H, d, J=16 Hz), 7.83–9.10 (4H, m), 9.40 (1H, s), 9.78 (1H, d, J=8 Hz).

(46) 7-[2-Methoxyimino-2-(3-hydroxyphenyl)acetamido]-3-[2-(1-methyl-3-pyridinio)thiovinyl]-3-cephem-4-carboxylate (syn isomer) (trans isomer).

IR (Nujol): 1770, 1650, 1600, 1570, 1500 cm$^{-1}$

NMR (DMSO-d$_6$/D$_2$O) δ: 3.50–4.17 (5H, m), 4.17–4.67 (3H, m), 5.17 (1H, d, J=5 Hz), 5.77 (1H, dd, J=5 Hz, 8 Hz), 6.60 (1H, d, J=16 Hz), 7.53 (1H, d, J=16 Hz), 6.83–7.40 (4H, m), 7.73–8.93 (4H, m).

(47) Trifluoroacetic acid salt of 7-amino-3-[2-(1-methyl-2-pyridinio)thiovinyl]-3-cephem-4-carboxylic acid iodide (cis isomer).

IR (Nujol): 2300–2500, 1780, 1670, 1610, 1560 cm$^{-1}$

NMR (DMSO-d$_6$) δ: 3.85 (2H, ABq, J=17 Hz), 4.20 (3H, s), 5.35 (2H, m), 6.67 (1H, d, J=10 Hz), 6.95–8.50 (4H, m), 9.10 (1H, broad s), 9.67 (2H, broad s).

(48) 7-[2-Methoxyimino-2-(2-aminothiazol-4-yl)acetamido]-3-[2-(1-methyl-2-pyridinio)thiovinyl)-3-cephem-4-carboxylate (syn isomer) (cis isomer).

IR (Nujol): 3400–3100, 1765, 1660, 1610, 1560, 1530 cm$^{-1}$

NMR (DMSO-d$_6$) δ: 3.67 (2H, ABq, J=16 Hz), 3.83 (3H, s), 4.17 (3H, s), 5.12 (1H, d, J=5 Hz), 5.63 (1H, dd, J=5 Hz, 8 Hz), 6.42 (1H, d, J=14 Hz), 6.73 (1H, s), 7.25 (2H, broad s), 7.63 (1H, d, J=14 Hz), 7.9–9.00 (4H, m), 9.57 (1H, d, J=8 Hz).

(49) 7-[(2-Methoxyimino-2-(2-aminothiazol-4-yl)acetamido]-3-[2-(1-methyl-3-pyridinio)thiovinyl-3-cephem-4-carboxylate (syn isomer) (cis isomer).

IR (Nujol): 3300, 1760, 1660, 1600, 1530 cm$^{-1}$

NMR (DMSO-d$_6$) δ: 3.72 (2H, ABq, J=16 Hz), 3.82 (3H, s), 4.33 (3H, s), 5.10 (1H, d, J=5 Hz), 5.65 (1H, dd, J=5 Hz, 8 Hz), 6.38 (1H, d, J=10 Hz), 6.73 (1H, s), 7.22 (1H, d, J=10 Hz), 7.18 (2H, broad s), 7.85–8.90 (3H, m), 9.17 (1H, broad s), 9.50 (1H, d, J=8 Hz).

(50) 7-[2-Methoxyimino-2-(2-tritylaminothiazol-4-yl)acetamido]-3-[2-(1-methyl-3-pyridinio)thiovinyl]-3-cephem-4-carboxylate (syn isomer) (trans isomer).

IR (Nujol): 3300–3400, 1770, 1675, 1620, 1600 cm$^{-1}$

NMR (DMSO-d$_6$) δ: 3.77 (3H, s), 3.80 (2H, m), 4.32 (3H, s), 5.17 (1H, d, J=5 Hz), 5.67 (1H, dd, J=5 Hz, 8 Hz), 6.70 (1H, s), 6.85–7.67 (17H, m), 8.00–9.03 (4H, m), 9.55 (1H, d, J=8 Hz).

(51) 7-[2-Methoxyimino-2-(2-tritylaminothiazol-4-yl)acetamido]-3-[2-(1-methyl-2-pyridinio)thiovinyl]-3-cephem-4-carboxylate (syn isomer) (cis isomer).

IR (Nujol): 3300–3200, 1775, 1680, 1660, 1615, 1600, 1570 cm$^{-1}$

NMR (DMSO-d$_6$) δ: 3.67–3.95 (2H, m), 3.78 (3H, s), 4.20 (3H, s), 5.17 (1H, d, J=5 Hz), 5.70 (1H, dd, J=5 Hz, 8 Hz), 6.70 (1H, s), 6.75 (1H, d, J=10 Hz), 7.00–7.50 (15H, m), 7.67–9.05 (4H, m), 9.52 (1H, d, J=8 Hz).

(52) 7-[2-Methoxyimino-2-(2-tritylaminothiazol-4-yl)acetamido]-3-[2-(1-methyl-3-pyridinio)thiovinyl]-3-cephem-4-carboxylate (syn isomer) (cis isomer).

IR (Nujol): 3350–3250, 1770, 1670, 1620, 1590 cm$^{-1}$

NMR (DMSO-d$_6$) δ: 3.70–4.00 (5H, m), 3.80 (3H, s), 4.30 (3H, s), 5.20 (1H, d, J=5 Hz), 5.70 (1H, dd, J=5 Hz, 8 Hz), 6.70 (1H, s), 6.73 (1H, d, J=11 Hz), 7.00 (1H, d, J=11 Hz), 7.15–7.50 (15H, m), 8.00–9.10 (5H, m), 9.50 (1H, d, J=8 Hz).

(53) 7-[2-(3-Carboxypropoxyimino)-2-(5-amino-1,2,4-thiodiazol-3-yl)acetamido]-3-[2-(1-methyl-3-pyridinio)thiovinyl]-3-cephem-4-carboxylate (syn isomer) (trans isomer).

IR (Nujol): 3300, 1765, 1665, 1600, 1530 cm$^{-1}$

NMR (DMSO-d$_6$) δ: 1.6–2.7 (4H, m), 3.75 (2H, broad s), 4.0–4.4 (2H, m), 4.40 (3H, s), 5.10 (1H, d, J=4 Hz), 5.72 (1H, dd, J=4, 8 Hz), 6.75 (1H, d, J=16 Hz), 7.44 (1H, d, J=16 Hz), 7.7–9.1 (4H, m), 9.60 (1H, d, J=8 Hz).

(54) 7-[2-Ethoxyimino-2-(5-amino-1,2,4-thiadiazol-3-yl)acetamido]-3-[2-(1-methyl-2-pyridinio)thiovinyl]-3-cephem-4-carboxylate (syn isomer) (cis isomer).

IR (Nujol): 3300, 1765, 1670, 1610, 1560 cm$^{-1}$

NMR (DMSO-d$_6$) δ: 1.27 (3H, t, J=5 Hz), 3.65–4.35 (4H, m), 5.10 (1H, J=5 Hz), 5.68 (1H, dd, J=5 Hz, 8 Hz), 6.42 (1H, d, J=14 Hz), 7.67 (1H, d, J=14 Hz), 6.95–9.00 (6H, m), 9.50 (1H, d, J=8 Hz).

(55) 7-[2-Ethoxyimino-2-(5-phosphonoamino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3200–3400 (broad), 1760, 1672, 1520 cm$^{-1}$

NMR (NaHCO$_3$-D$_2$O) δ: 1.33 (3H, t, J=7 Hz), 3.77 (2H, broad s), 4.35 (3H, s), 4.33 (2H, q, J=7 Hz), 5.30 (1H, d, J=5 Hz), 5.82 (1H, d, J=5 Hz), 6.60 (1H, d, J=15 Hz), 7.17 (1H, d, J=15 Hz), 7.85–8.80 (4H, m).

(56) 7-[2-Ethoxyimino-2-(5-phosphonoamino-1,2,4-thiadiazol-3-yl)acetamido]-3-[2-(1-methyl-2-pyridinio)-thiovinyl]-3-cephem-4-carboxylate (syn isomer) (trans isomer).

IR (Nujol): 3200, 1768, 1673, 1610, 1560, 1508, 1269, 1230 cm$^{-1}$

NMR (NaHCO$_3$-D$_2$O) δ: 1.33 (3H, t, J=7 Hz), 3.83 (2H, broad s), 4.23 (3H, s), 4.38 (2H, q, J=7 Hz), 5.30 (1H, d, J=5 Hz), 5.80 (1H, d, J=5 Hz), 6.60 (1H, d, J=14 Hz), 7.38 (1H, d, J=14 Hz), 7.4–8.8 (4H, m).

EXAMPLE 6

To a solution of trifluoroacetic acid salt of 7-amino-3-[2-(1-methyl-3-pyridinio)thiovinyl]-3-cephem-4-carboxylate hydroiodide (trans isomer) (17.5 g) in tetrahydrofuran (300 ml) containing morotrimethylsilylacetamide (27 g) was added 2-ethoxyimino-2-(5-amino-1,2,4-thiadiazol-3-yl)acetylchloride hydrochloride (syn isomer) (10.5 g) under stirring at −10°–−5° C. The mixture was stirred for 1.5 hours under the same conditions. After removal of the solvent, to the residue were added ethyl acetate (1 l) and 5% aqueous sodium bicarbonate (300 ml). The separated aqueous layer was concentrated in vacuo at 30° C. The resulting aqueous solution was adjusted to pH 4.5 with 10% hydrochloric acid under ice-cooling, and subjected to a column chromatography on macroporous non-ionic adsorption resin "Diaion HP-20" and eluted with 5% aqueous solution of isopropyl alcohol. The fractions, containing the desired compound, were combined, concentrated in vacuo and lyophilized to give 7-[2-ethoxyimino-2-(5-amino-1,2,4-thiadiazol-3-yl)acetamido]-3-[2-(1-methyl-3-pyridinio)-thiovinyl]-3-cephem-4-carboxylate (syn isomer) (trans isomer) (6.0 g).

IR (Nujol): 3300 (broad), 1760, 1660, 1600, 1520 $cm^{-1}$

NMR (DMSO-$d_6$) δ: 1.30 (2H, t, J=7 Hz), 3.1–3.8 (2H, m), 4.28 (3H, q, J=7 Hz), 4.40 (3H, s), 5.12 (1H, d, J=4 Hz), 5.71 (1H, dd, J=4.8 Hz), 6.53 and 7.50 (2H, 2xd, J=16 Hz), 7.8–9.20 (5H, m), 9.50 (1H, d, J=8 Hz).

EXAMPLE 7

The following compound was obtained according to a similar manner to that of Example 6.

(1) 7-[2-ethoxyimino-2-(5-amino-1,2,4-thiadiazol-3-yl)acetamido]-3-[2-(1-methyl-2-pyridinio)thiovinyl]-3-cephem-4-carboxylate (syn isomer) (trans isomer).

IR (Nujol): 3300, 3200, 1760, 1650, 1600 $cm^{-1}$

NMR (DMSO-$d_6$) δ: 1.28 (3H, m), 3.55 (2H, ABq, J=18 Hz), 4.20 (3H, s), 4.15 (2H, m), 5.15 (1H, d, J=5 Hz), 5.70 (1H, dd, J=8 Hz, 5 Hz), 6.65 (1H, d, J=16 Hz), 7.80 (1H, d, J=16 Hz), 8.00–8.50 (5H, m), 8.90 (1H, broad s), 9.55 (1H, d, J=8 Hz).

(2) 7-[2-Ethoxyimino-2-(5-amino-1,2,4-thiadiazol-3-yl)acetamido]-3-[2-(1-methyl-2-pyridinio)thiovinyl]-3-cephem-4-carboxylate hydriodide (syn isomer) (trans isomer).

IR (Nujol): 3400, 3250, 1780, 1650–1680, 1620 $cm^{-1}$.

(3) 7-[2-Methoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3400–3100 (broad), 1760, 1660, 1600, 1520 $cm^{-1}$.

(4) 7-[2-Methoxyimino-2-(2-aminothiazol-4-yl)acetamido]-3-[2-(1-methyl-2-pyridinio)thiovinyl]-3-cephem-4-carboxylate (syn isomer) (trans isomer).

IR (Nujol): 3300, 1765, 1670, 1611, 1562, 1533 $cm^{-1}$.

(5) 7-[2-Methoxyimino-2-(2-aminothiazol-4-yl)acetamido]-3-[2-(4-methyl-2-pyrazinio)thiovinyl]-3-cephem-4-carboxylate (syn isomer) (trans isomer).

IR (Nujol): 3300, 1765 (br.), 1660, 1600 $cm^{-1}$.

(6) 7-[2-Methoxyimino-2-(2-tritylaminothiazol-4-yl)acetamido]-3-[2-(1-methyl-2-pyridinio)thiovinyl]-3-cephem-4-carboxylate (syn isomer) (trans isomer).

IR (Nujol): 3250, 1780, 1672, 1595 $cm^{-1}$

NMR (DMSO-$d_6$) δ: 3.77 (3H, s), 3.80 (2H, m), 4.16 (3H, s), 5.20 (1H, d, J=5 Hz), 5.77 (1H, dd, J=5 Hz and 8 Hz), 6.70 (1H, s), 6.8–7.7 (18H, m), 7.7–9.05 (4H, m), 9.57 (1H, d, J=8 Hz).

(7) 7-[2-Methoxyimino-2-(2-tert-pentyloxycarbonylaminothiazol-4-yl)acetamido]-3-[2-(4-methyl-2-pyrazinio)thiovinyl]-3-cephem-4-carboxylate (syn isomer) (trans isomer).

IR (Nujol): 3350, 1762, 1700, 1660, 1530 $cm^{-1}$

NMR (DMSO-$d_6$) δ: 0.86 (3H, t, J=7 Hz), 1.43 (6H, s), 1.73 (2H, q, J=7 Hz), 3.85 (2H, m), 3.88 (3H, s), 4.4 (3H, s), 5.25 (1H, d, J=5 Hz), 5.83 (1H, dd, J=5 Hz and 8 Hz), 7.26 (1H, s), 7.30 (2H, br.s), 8.87 (1H, m), 9.30 (2H, m), 9.73 (1H, d, J=8 Hz).

(8) 7-[2-Ethoxyimino-2-(5-amino-1,2,4-thiadiazol-3-yl)acetamido]-3-[2-(1,3-dimethyl-2-pyrimidinio)thiovinyl]-3-cephem-4-carboxylate iodide (syn isomer) (trans isomer).

IR (Nujol): 3350, 1770, 1663, 1605 $cm^{-1}$.

(9) 7-[2-Ethoxyimino-2-(5-amino-1,2,4-thiadiazol-3-yl)acetamido]-3-[2-(4-methyl-2-pyrazinio)thiovinyl]-3-cephem-4-carboxylate (syn isomer) (trans isomer).

IR (Nujol): 3350, 1760 (br.), 1665, 1607 $cm^{-1}$

NMR (DMSO-$d_6$) δ: 1.20 (3H, t, J=7 Hz), 3.90 (2H, br.s), 4.13 (2H, q, J=7 Hz), 4.26 (3H, s), 5.17 (1H, d, J=5 Hz), 5.77 (1H, dd, J=5 Hz, 8 Hz), 7.22 (2H,br.s), 8.03 (2H, br.s), 8.80 (1H, br.s), 9.20 (2H, br.s), 9.50 (1H, d, J=8 Hz).

(10) 7-[2-Methoxyimino-2-(5-amino-1,2,4-thiadiazol-3-yl)acetamido]-3-[2-(1-methyl-2-pyridinio)thiovinyl]-3-cephem-4-carboxylate (syn isomer) (trans isomer).

IR (Nujol): 3250–3350, 1770, 1660, 1620, 1560, 1530 $cm^{-1}$

NMR (DMSO-$d_6$) δ: 3.5–4.1 (2H, m), 3.90 (3H, s), 4.17 (3H, s), 5.10 (1H, d, J=5 Hz), 5.87 (1H, d-d, J=5 Hz, and 8 Hz), 6.50 (1H, d, J=16 Hz), 7.67 (1H, d, J=16 Hz), 8.00–8.3 (5H, m), 8.97 (1H, d, J=5 Hz), 9.55 (1H, d, J=8 Hz).

(11) 7-[2-Ethoxyimino-2-(5-amino-1,2,4-thiadiazol-3-yl)acetamido]-3-[2-(1-ethyl-3-pyridinio)thiovinyl]-3-cephem-4-carboxylate (syn isomer) (trans isomer).

IR (Nujol): 3300 (broad), 1770, 1675, 1600, 1520 $cm^{-1}$.

(12) 7-[2-Ethoxyimino-2-(5-amino-1,2,4-thiadiazol-3-yl)acetamido]-3-[2-(1-methyl-3-pyridinio)thiovinyl]-3-cephem-4-carboxylate (syn isomer) (cis isomer).

IR (Nujol): 3300 (broad), 1760, 1665, 1600, 1520 $cm^{-1}$

NMR (DMSO-$d_6$) δ: 1.23 (3H, t, J=7 Hz), 4.06 (2H, ABq, J=7 Hz), 4.35 (3H, s), 5.04 (1H, d, J=5 Hz), 5.65 (1H, d-d, J=5 Hz, 8 Hz), 6.38 (1H, d, J=10 Hz), 7.25 (1H, d, J=10 Hz), 7.87–9.30 (6H, m), 9.43 (1H, d, J=8 Hz).

(13) 7-[2-Carboxymethoxyimino-2-(5-amino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3300 (broad), 1765, 1670, 1615, 1560, 1525 $cm^{-1}$

NMR (DMSO-$d_6$) δ: 4.27 (2H, ABq, J=18 Hz), 4.33 (3H, s), 4.63 (2H, s), 5.02 (1H, d, J=5 Hz), 5.76 (1H, d-d, J=5, 8 Hz), 6.68 (1H, d, J=14 Hz), 7.35 (1H, d, J=14 Hz), 7.67–9.10 (6H, m), 10.03 (1H, d, J=8 Hz).

(14) 7-[2-Allyloxyimino-2-(5-amino-1,2,4-thiadiazol-3-yl)acetamido]-3-[2-(1-methyl-3-pyridinio)thiovinyl]-3-cephem-4-carboxylate (syn isomer) (trans isomer).

IR (Nujol): 3300, 1760, 1670, 1620, 1600, 1530 $cm^{-1}$

NMR (DMSO-$d_6$) δ: 3.70 (2H, b.s), 4.40 (3H, s), 5.10 (2H, d, J=5 Hz), 5.15–5.95 (4H, m), 6.53 (1H, d, J=16 Hz), 7.45 (1H, d, J=16 Hz), 8.00–9.10 (6H, m), 9.57 (1H, d, J=8 Hz).

(15) 7-[2-(Tert-butoxycarbonylmethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3200–3300, 2400–2600, 1770, 1715, 1680, 1630 $cm^{-1}$

NMR (DMSO-$d_6$) δ: 1.50 (9H, s), 3.20–4.10 (2H, m), 4.43 (3H, s), 4.70 (2H, s), 5.30 (1H, d, J=5 Hz), 5.83 (1H, dd, J=5 Hz, 8 Hz), 7.00 (1H, s), 7.30 (2H, broad s), 8–9.00 (6H, m), 9.27 (1H, broad s), 9.77 (1H, d, J=8 Hz).

(16) 7-[2-Carboxymethoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1765, 1670, 1620 cm$^{-1}$

NMR (DMSO-$d_6$) δ: 3.50–4.10 (2H, m), 4.30 (3H, s), 4.63 (2H, broad s), 5.23 (1H, d, J=5 Hz), 5.90 (1H, dd, J=5 Hz, 8 Hz), 6.87 (1H, s), 6.95 (1H, d, J=15 Hz), 7.15 (2H, broad s), 7.47 (1H, d, J=15 Hz), 7.90–8.90 (3H, m), 9.13 (1H, broad s), 9.80 (1H, d, J=8 Hz).

(17) 7-[2-(3-Carboxy-2-propenyloxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535 cm$^{-1}$

NMR (DMSO-$d_6$/$D_2O$) δ: 3.57–4.20 (2H, m), 4.37 (3H, s), 4.57–4.93 (2H, m), 5.10 (1H, d, J=5 Hz), 5.60 (1H, dd, J=5 Hz, 8 Hz), 5.98 (1H, d, J=16 Hz), 6.51 (1H, d, J=16 Hz), 7.48 (1H, d, J=16 Hz), 6.78 (1H, s), 7.76–9.17 (4H, m), 9.67 (1H, d, J=8 Hz).

(18) 7-[2-(1-Methyl-2-pyridiniomethoxyimino)-2-(2-aminothiazol-4-yl)acetamido]-3-[2-(1-methyl-3-pyridinio)thiovinyl]-3-cephem-4-carboxylate iodide (syn isomer) (trans isomer).

IR (Nujol): 3250, 1760, 1665, 1615 cm$^{-1}$

NMR ($D_2O$) δ: 7.9–9.00 (8H, m), 7.17 (1H, d, J=16 Hz), 7.10 (1H, s), 6.67 (1H, d, J=16 Hz), 5.90 (1H, d, J=5 Hz), 5.75 (2H, s), 5.34 (1H, d, J=5 Hz), 4.45 (6H, s), 3.5–4.25 (2H, m).

(19) 7-[2-(2-Pyridylmethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1620, 1590 cm$^{-1}$

NMR (DMSO-$d_6$) δ: 3.7–4.20 (2H, m), 4.47 (3H, s), 5.15 (1H, d, J=5 Hz), 5.25 (2H, s), 5.72 (1H, dd, J=5 Hz, 8 Hz), 6.48 (1H, d, J=14 Hz), 6.80 (1H, s), 7.1–9.0 (11H, m), 9.90 (1H, d, J=8 Hz).

(20) 7-[2-(3-Carboxypropoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535 cm$^{-1}$

NMR (DMSO-$d_6$/$D_2O$) δ: 1.5–2.73 (4H, m), 3.3–4.27 (4H, m), 4.37 (3H, s), 5.08 (1H, d, J=5 Hz), 5.63 (1H, dd, J=5 Hz, 8 Hz), 6.50 (1H, d, J=16 Hz), 7.48 (1H, d, J=16 Hz), 6.74 (1H, s), 7.76–9.13 (4H, m), 9.55 (1H, d, J=8 Hz).

(21) 7-[2-(1-Carboxypropoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1590 cm$^{-1}$

NMR (DMSO-$d_6$) δ: 1.08 (3H, t, J=7 Hz), 1.62–2.24 (2H, m), 3.2–3.9 (2H, m), 4.42 (3H, s), 4.47 (1H, t, J=6 Hz), 5.15 (1H, d, J=5 Hz), 5.77 (1H, dd, J=8 Hz, 5 Hz), 6.47 (1H, d, J=16 Hz), 6.87 (1H, s), 7.0 (1H, d, J=16 Hz), 7.02–9.3 (4H, m).

(22) 7-[2-Allyloxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1530 cm$^{-1}$

NMR (DMSO-$d_6$/$D_2O$) δ: 3.33–3.87 (4H, m), 4.37 (3H, s), 4.62 (2H, d, J=5 Hz), 6.50 (1H, d, J=16 Hz), 7.47 (1H, d, J=16 Hz), 6.73 (1H, s), 7.83–9.03 (4H, m), 9.57 (1H, d, J=8 Hz).

(23) 7-[2-(2-Hydroxyethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535, 1500 cm$^{-1}$

NMR (DMSO-$d_6$/$D_2O$) δ: 3.20–3.83 (2H, m), 4.35 (3H, s).

(24) 7-[2-Ethoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1665, 1600, 1535 cm$^{-1}$

NMR (DMSO-$d_6$/$D_2O$) δ: 1.25 (3H, t, J=7 Hz), 4.13 (2H, ABq, J=7 Hz), 4.37 (3H, s), 5.08 (1H, d, J=5 Hz), 5.65 (1H, dd, J=5 Hz, 8 Hz), 6.48 (1H, d, J=16 Hz), 7.48 (1H, d, J=16 Hz), 7.73–7.93 (4H, m), 9.52 (1H, d, J=8 Hz), 6.73 (1H, s).

(25) 7-[2-(2-Propynyloxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3250, 1760, 1660, 1600, 1530 cm$^{-1}$

NMR (DMSO-$d_6$/$D_2O$) δ: 3.3–3.8 (3H, m), 4.37 (3H, s), 4.7 (2H, s), 5.09 (1H, d, J=5 Hz), 5.63 (1H, dd, J=5 Hz, 8 Hz), 6.53 (1H, d, J=16 Hz), 6.78 (1H, s), 7.50 (1H, d, J=16 Hz), 7.73–7.93 (4H, m), 9.05 (1H, s), 9.52 (1H, d, J=8 Hz).

(26) 7-[2-(Tert-butoxycarbonylmethoxyimino)-2-(2-formamidothiazol-4-yl)acetamido]-3-[2-(1-methyl-3-pyridinio)thiovinyl]-3-cephem-4-carboxylate (syn isomer) (trans isomer).

IR (Nujol): 3200–3400, 1760, 1720–1730, 1690, 1670 cm$^{-1}$

NMR (DMSO-$d_6$) δ: 1.50 (9H, s), 3.50–4.20 (2H, m), 4.37 (3H, s), 4.63 (2H, s), 5.27 (1H, d, J=5 Hz), 5.87 (1H, dd, J=5 Hz, 8 Hz), 7.00 (1H, d, J=16 Hz), 7.40 (1H, d, J=16 Hz), 7.45 (1H, s), 7.95–9.10 (4H, m), 8.53 (1H, s), 9.67 (1H, d, J=8 Hz), 12.70 (1H, broad s).

(27) 7-{2-(1-Tert-butoxycarbonyl)propoxyimino]-2-(2-formamidothiazol-4-yl)acetamido]}-3-[2-(1-methyl-3-pyridinio)thiovinyl]-3-cephem-4-carboxylate (syn isomer) (trans isomer).

IR (Nujol): 3250, 1760, 1720, 1680 cm$^{-1}$

NMR (DMSO-$d_6$) δ: 0.98 (3H, t, J=7 Hz), 1.45 (9H, s), 1.52–2.06 (2H, m), 3.67–4.17 (2H, m), 4.37 (3H, s), 4.5 (1H, t, J=6 Hz), 5.28 (1H, d, J=5 Hz), 5.93 (1H, dd, J=8 Hz, 5 Hz), 6.43 (1H, d, J=16 Hz), 7.22 (1H, s), 7.63 (1H, d, J=16 Hz), 7.83–9.33 (4H, m), 8.52 (1H, s), 9.6 (1H, d, J=8 Hz).

(28) 7-[2-(2-Pyridylmethoxyimino)-2-(2-formamidothiazol-4-yl)acetamido]-3-[2-(1-methyl-3-pyridinio)-thiovinyl]-3-cephem-4-carboxylate (syn isomer) (trans isomer).

NMR (DMSO-$d_6$) δ: 3.3–4.00 (2H, m), 4.33 (3H, s), 5.13 (1H, d, J=5 Hz), 5.30 (2H, broad s), 5.83 (1H, dd, J=5 Hz, 8 Hz), 6.50 (1H, d, J=15 Hz), 7.20–9.00 (9H, m), 7.43 (1H, s), 8.50 (1H, s), 9.95 (1H, d, J=8 Hz).

(29) 7-[2-(3-Benzhydryloxycarbonyl-2-propenyloxyimino)-2-(2-tritylaminothiazol-4-yl)acetamido]-3-[2-(1-methyl-3-pyridinio)thiovinyl]-3-cephem-4-carboxylate (syn isomer) (trans isomer).

IR (Nujol): 3300, 1780, 1720, 1680, 1600, 1530, 1500 cm$^{-1}$

NMR (DMSO-$d_6$/$D_2O$) δ: 3.7–4.35 (2H, m), 4.40 (3H, s), 4.67–5.00 (2H, m), 5.27 (1H, d, J=5 Hz), 5.83 (1H, m), 6.25 (1H, d, J=16 Hz), 6.67–7.00 (3H, m), 7.33 (26H, m), 8.00–9.20 (5H, m), 9.80 (1H, d, J=8 Hz).

(30) 7-[2-Ethoxyimino-2-(2-tritylaminothiazol-4-yl)acetamido]-3-[2-(1-methyl-3-pyridinio)thiovinyl]-3-cephem-4-carboxylate (syn isomer) (trans isomer).

NMR (DMSO-$d_6$/$D_2O$) δ: 1.20 (3H, t, J=7 Hz), 3.6–4.0 (2H, m), 4.06 (2H, ABq, J=7 Hz), 4.37 (3H, s), 5.15 (1H, d, J=5 Hz), 5.67 (1H, dd, J=5 Hz, 8 Hs), 6.72 (1H, s), 7.17–7.50 (15H, m), 8.43–9.17 (4H, m), 9.51 (1H, d, J=5 Hz).

(31) 7-[2-(2-Propynyloxyimino)-2-(2-tritylaminothiazol-4-yl)acetamido]-3-[2-(1-methyl-3-pyridinio)thiovinyl]-3-cephem-4-carboxylate (syn isomer) (trans isomer).

NMR (DMSO-d$_6$/D$_2$O) δ: 3.4–3.7 (3H, m), 4.37 (3H, s), 5.21 (1H, d, J=5 Hz), 5.73 (1H, dd, J=5 Hz, 8 Hz), 6.78 (1H, s), 7.13–7.50 (15H, m), 9.65 (1H, d, J=8 Hz).

(32) 7-[2-(3-Benzhydryloxycarbonylpropoxyimino)-2-(2-tritylaminothiazol-4-yl)acetamido]-3-[2-(1-methyl-3-pyridinio)thiovinyl]-3-cephem-4-carboxylate (syn isomer) (trans isomer).

IR (Nujol): 3350, 1770, 1720, 1665, 1590, 1520 cm$^{-1}$

NMR (DMSO-d$_6$/D$_2$O) δ: 1.53–2.10 (4H, m), 3.50–3.70 (2H, m), 3.83–4.27 (2H, m), 4.35 (3H, s), 5.17 (1H, d, J=8 Hz), 5.63 (1H, m), 6.78 (1H, s), 6.87 (1H, d, J=15 Hz), 6.90 (1H, s), 7.10–7.50 (26H, m), 7.80–9.17 (4H, m), 9.60 (1H, d, J=8 Hz).

(33) 7-[2-Carboxymethoxyimino-2-(thiazol-4-yl)acetamido]-3-[2-(1-methyl-3-pyridinio)thiovinyl]-3-cephem-4-carboxylate (syn isomer) (trans isomer).

IR (Nujol): 3350, 1760, 1660, 1600 cm$^{-1}$

NMR (D$_2$O-NaHCO$_3$) δ: 3.73 (2H, s), 4.35 (3H, s), 4.50–4.87 (2H, m), 5.32 (1H, d, J=5 Hz), 5.83 (1H, dd, J=5 Hz, 8 Hz), 6.63 (1H, d, J=16 Hz), 7.17 (1H, d, J=16 Hz), 7.80–8.80 (6H, m).

(34) 7-[2-Hydroxy-2-(2-aminothiazol-4-yl)acetamido]-3-[2-(1-methyl-3-pyridinio)thiovinyl]-3-cephem-4-carboxylate (trans isomer).

IR (Nujol): 3300, 1760, 1670, 1600 cm$^{-1}$

NMR (DMSO-d$_6$) δ: 3.42–4.04 (2H, m), 4.43 (3H, s), 5.00 (1H, s), 5.15 (1H, d, J=5 Hz), 5.70 (1H, dd, J=8 Hz, 5 Hz), 6.54 (1H, s), 6.6 (1H, d, J=16 Hz), 7.02 (2H, broad s), 7.53 (1H, d, J=16 Hz), 7.73–9.17 (4H, m).

(35) 7-[2-(1-Carboxy)ethoxyimino-2-(5-amino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3300, 1770, 1665, 1600, 1520 cm$^{-1}$

NMR (DMSO-d$_6$/D$_2$O) δ: 1.51 (3H, d, J=6 Hz), 3.80 (2H, broad s), 4.31 (3H, s), 4.75 (1H, d, J=6 Hz), 5.25 (1H, d, J=4 Hz), 5.85 (1H, d, J=4 Hz), 6.83 (1H, d, J=16 Hz), 7.50 (1H, d, J=16 Hz), 7.6–9.4 (4H, m).

(36) 7-[2-(1-Methyl-1-carboxyethoxyimino)-2-(5-amino-1,2,4-thiadiazol-3-yl)acetamido]-3-[2-(1-methyl-3-pyridinio)thiovinyl]-3-cephem-4-carboxylate (syn isomer) (trans isomer).

IR (Nujol): 3300, 1770, 1670, 1610, 1520 cm$^{-1}$

NMR (D$_2$O-NaHCO$_3$) δ: 1.60 (6H, s), 3.82 (2H, s), 4.42 (3H, s), 5.35 (1H, d, J=4 Hz), 5.90 (1H, d, J=4 Hz), 6.70 (1H, d, J=16 Hz), 7.20 (1H, d, J=16 Hz), 7.5–8.9 (3H, m).

(37) 7-[2-Ethoxyimino-2-(5-amino-1,2,4-thiadiazol-3-yl)acetamido]-3-[2-(1-carboxymethyl-3-pyridinio)thiovinyl]-3-cephem-4-carboxylate (syn isomer) (trans isomer).

IR (Nujol): 3300, 1760, 1640–1680, 1610, 1520 cm$^{-1}$

NMR (DMSO-d$_6$) δ: 1.30 (3H, t, J=5 Hz), 3.33–3.90 (2H, m), 4.25 (2H, q, J=7 Hz), 4.95–5.20 (3H, m), 5.75 (1H, m), 6.60 (1H, d, J=16 Hz), 7.50 (1H, d, J=16 Hz), 8.00–9.00 (4H, m), 9.55 (1H, d, J=8 Hz).

(38) 7-[2-Ethoxyimino-2-(5-amino-1,2,4-thiadiazol-3-yl)acetamido]-3-[2-(2-trimethylammonioethyl)thiovinyl]-3-cephem-4-carboxylate (syn isomer) (trans isomer).

IR (Nujol): 3300, 1760, 1670, 1600, 1520 cm$^{-1}$

NMR (DMSO-d$_6$) δ: 1.25 (3H, t, J=5 Hz), 3.10–4.00 (6H, m), 4.20 (2H, q, J=7 Hz), 5.05 (1H, d, J=5 Hz), 5.60 (1H, m), 6.60 (1H, d, J=16 Hz), 7.03 (1H, d, J=16 Hz), 8.06 (2H, broad s), 9.50 (1H, d, J=8 Hz).

(39) 7-[(4-Carboxy-3-hydroxyisothiazol-5-yl)thioacetamido]-3-[2-(1-methyl-3-pyridinio)thiovinyl]-3-cephem-4-carboxylate (trans isomer).

IR (Nujol): 3300, 1760, 1670 cm$^{-1}$

NMR (DMSO-d$_6$) δ: 3.93 (2H, s), 3.83–4.00 (2H, m), 4.47 (3H, s), 5.27 (1H, d, J=5 Hz), 5.70 (1H, dd, J=8 Hz, 5 Hz), 7.30 (6H, m), 9.50 (1H, d, J=8 Hz).

(40) 7-[2-Methoxyimino-2-(5,6-dihydro-1,4-oxathiin-2-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1500 cm$^{-1}$

NMR (D$_2$O) δ: 3.0–3.23 (2H, m), 3.73 (2H, s), 4.33 (3H, s), 5.22 (1H, d, J=5 Hz), 5.71 (1H, d, J=5 Hz), 5.97 (1H, s), 6.58 (1H, d, J=16 Hz), 7.12 (1H, d, J=16 Hz).

(41) 7-[2-Methoxyimino-2-(1,2,3-thiadiazol-4-yl)acetamido]-3-[2-(1-methyl-3-pyridinio)thiovinyl]-3-cephem-4-carboxylate (syn isomer) (trans isomer).

IR (Nujol): 3200–3350, 1760, 1660, 1600, 1555 cm$^{-1}$

NMR (DMSO-d$_6$/D$_2$O) δ: 3.67 (2H, s), 4.02 (3H, s), 4.37 (3H, s), 5.13 (1H, d, J=5 Hz), 5.80 (1H, dd, J=5 Hz, 8 Hz), 6.50 (1H, d, J=16 Hz), 7.50 (1H, d, J=16 Hz), 7.83–9.10 (4H, m), 9.40 (1H, s), 9.78 (1H, d, J=8 Hz).

(42) 7-[2-Methoxyimino-2-(3-hydroxyphenyl)acetamido]-3-[2-(1-methyl-3-pyridinio)thiovinyl]-3-cephem-4-carboxylate (syn isomer) (trans isomer).

IR (Nujol): 1770, 1650, 1600, 1570, 1500 cm$^{-1}$

NMR (DMSO-d$_6$/D$_2$O) δ: 3.50–4.17 (5H, m), 4.17–4.67 (3H, m), 5.17 (1H, d, J=5 Hz), 5.77 (1H, dd, J=5 Hz, 8 Hz), 6.60 (1H, d, J=16 Hz), 7.53 (1H, d, J=16 Hz), 6.83–7.40 (4H, m), 7.73–8.93 (4H, m).

(43) 7-[2-Methoxyimino-2-(2-aminothiazol-4-yl)acetamido]-3-[2-(1-methyl-2-pyridinio)thiovinyl]-3-cephem-4-carboxylate (syn isomer) (cis isomer).

IR (Nujol): 3400–3100, 1765, 1660, 1610, 1560, 1530 cm$^{-1}$

NMR (DMSO-d$_6$) δ: 3.67 (2H, ABq, J=16 Hz), 3.83 (3H, s), 4.17 (3H, s), 5.12 (1H, d, J=5 Hz), 5.63 (1H, dd, J=5 Hz, 8 Hz), 6.42 (1H, d, J=14 Hz), 6.73 (1H, s), 7.25 (2H, broad s), 7.63 (1H, d, J=14 Hz), 7.9–9.00 (4H, m), 9.57 (1H, d, J=8 Hz).

(44) 7-[(2-Methoxyimino-2-(2-aminothiazol-4-yl)acetamido]-3-[2-(1-methyl-3-pyridinio)thiovinyl]-3-cehem-4-carboxylate (syn isomer) (cis isomer).

IR (Nujol): 3300, 1760, 1660, 1600, 1530 cm$^{-1}$

NMR (DMSO-d$_6$) δ: 3.72 (2H, ABq, J=16 Hz), 3.82 (3H, s), 4.33 (3H, s), 5.10 (1H, d, J=5 Hz), 5.65 (1H, dd, J=5 Hz, 8 Hz), 6.38 (1H, d, J=10 Hz), 6.73 (1H, s), 7.22 (1H, d, J=10 Hz), 7.18 (2H, broad s), 7.85–8.90 (3H, m), 9.17 (1H, broad s), 9.50 (1H, d, J=8 Hz).

(45) 7-[2-Methoxyimino-2-(2-tritylaminothiazol-4-yl)acetamido]-3-[2-(1-methyl-3-pyridinio)thiovinyl]-3-cephem-4-carboxylate (syn isomer) (trans isomer).

IR (Nujol): 3300–3400, 1770, 1675, 1620, 1600 cm$^{-1}$

NMR (DMSO-d$_6$) δ: 3.77 (3H, s), 3.80 (2H, m), 4.32 (3H, s), 5.17 (1H, d, J=5 Hz), 5.67 (1H, dd, J=5 Hz, 8 Hz), 6.70 (1H, s), 6.85–7.67 (17H, m), 8.00–9.03 (4H, m), 9.55 (1H, d, J=8 Hz).

(46) 7-[2-Methoxyimino-2-(2-tritylaminothiazol-4-yl)acetamido]-3-[2-(1-methyl-2-pyridinio)thiovinyl]-3-cephem-4-carboxylate (syn isomer) (cis isomer).

IR (Nujol): 3300–3200, 1775, 1680, 1660, 1615, 1600, 1570 cm$^{-1}$

NMR (DMSO-d$_6$) δ: 3.67–3.95 (2H, m), 3.78 (3H, s), 4.20 (3H, s), 5.17 (1H, d, J=5 Hz), 5.70 (1H, dd, J=5 Hz, 8 Hz), 6.70 (1H, s), 6.75 (1H, d, J=10 Hz), 7.00–7.50 (15H, m), 7.67–9.05 (4H, m), 9.52 (1H, d, J=8 Hz).

(47) 7-[2-Methoxyimino-2-(2-tritylaminothiazol-4-yl)acetamido]-3-[2-(1-methyl-3-pyridinio)thiovinyl]-3-cephem-4-carboxylate (syn isomer) (cis isomer).

IR (Nujol): 3350–3250, 1770, 1670, 1620, 1590 cm$^{-1}$

NMR(DMSO-d$_6$) δ: 3.70–4.00 (5H, m), 3.80 (3H, s), 4.30 (3H, s), 5.20 (1H, d, J=5 Hz), 5.70 (1H, dd, J=5 Hz, 8 Hz), 6.70 (1H, s), 6.73 (1H, d, J=11 Hz), 7.00 (1H, d, J=11 Hz), 7.15–7.50 (15H, m), 8.00–9.10 (5H, m), 9.50 (1H, d, J=8 Hz).

(48) 7-[2-(3-Carboxypropoxyimino)-2-(5-amino-1,2,4-thiodiazol-3-yl)acetamido]-3-[2-(1-methyl-3-pyridinio)-thiovinyl]-3-cephem-4-carboxylate (syn isomer) (trans isomer).

IR (Nujol): 3300, 1765, 1665, 1600, 1530 cm$^{-1}$

NMR (DMSO-d$_6$) δ: 1.6–2.7 (4H, m), 3.75 (2H, broad s), 4.0–4.4 (2H, m), 4.40 (3H, s), 5.10 (1H, d, J=4 Hz), 5.72 (1H, dd, J=4, 8 Hz), 6.75 (1H, d, J=16 Hz), 7.44 (1H, d, J=16 Hz), 7.7–9.1 (4H, m), 9.60 (1H, d, J=8 Hz).

(49) 7-[2-Ethoxyimino-2-(5-amino-1,2,4-thiadiazol-3-yl)acetamido]-3-[2-(1-methyl-2-pyridinio)thiovinyl]-3-cephem-4-carboxylate (syn isomer) (cis isomer).

IR (Nujol): 3300, 1765, 1670, 1610, 1560 cm$^{-1}$

NMR (DMSO-d$_6$) δ: 1.27 (3H, t, J=5 Hz), 3.65–4.35 (4H, m), 5.10 (1H, J=5 Hz), 5.68 (1H, dd, J=5 Hz, 8 Hz), 6.42 (1H, d, J=14 Hz), 7.67 (1H, d, J=14 Hz), 6.95–9.00 (6H, m), 9.50 (1H, d, J=8 Hz).

(50) 7-[2-Ethoxyimino-2-(5-phosphonoamino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3200–3400 (broad), 1760, 1672, 1520 cm$^{-1}$

NMR (NaHCO$_3$-D$_2$O) δ: 1.33 (3H, t, J=7 Hz), 3.77 (2H, broad s), 4.35 (3H, s), 4.33 (2H, q, J=7 Hz), 5.30 (1H, d, J=5 Hz), 5.82 (1H, d, J=5 Hz), 6.60 (1H, d, J=15 Hz), 7.17 (1H, d, J=15 Hz), 7.85–8.80 (4H, m).

(51) 7-[2-Ethoxyimino-2-(5-phosphonoamino-1,2,4-thiadiazol-3-yl)acetamido]-3-[2-(1-methyl-2-pyridinio)-thiovinyl]-3-cephem-4-carboxylate (syn isomer) (trans isomer).

IR (Nujol): 3200, 1768, 1673, 1610, 1560, 1508, 1269, 1230 cm$^{-1}$

NMR (NaHCO$_3$-D$_2$O) δ: 1.33 (3H, t, J=7 Hz), 3.83 (2H, broad s), 4.23 (3H, s), 4.28 (2H, q, J=7 Hz), 5.30 (1H, d, J=5 Hz), 5.80 (1H, d, J=5 Hz), 6.60 (1H, d, J=14 Hz), 7.38 (1H, d, J=14 Hz), 7.4–8.8 (4H, m).

EXAMPLE 8

To a suspension of 7-[2-methoxyimino-2-(2-tert-pentyloxycarbonylaminothiazol-4-yl)acetamido]-3-[2-(4-methyl-2-pyrazinio)thiovinyl]-3-cephem-4-carboxylate (syn isomer)(trans isomer) (1.0 g) in anisole (2 ml) was added trifluoroacetic acid (6 ml) under ice-cooling with stirring. The mixture was stirred at ambient temperature for 2 hours. The resulting solution was poured into diisopropyl ether (200 ml). The precipitates were collected by filtration and dissolved water (100 ml) at pH 4.5. The aqueous solution was subjected to column chromatography on macroporous non-ionic resin "Diaion HP-20" and eluted with 20% aqueous solution of isopropyl alcohol. The fractions containing object compound were concentrated and lyophilized to give 7-[2-methoxyimino-2-(2-aminothiazol-4-yl)acetamido]-3-[2-(4-methyl-2-pyrazinio)thiovinyl]-3-cephem-4-carboxylate (syn isomer) (trans isomer) (0.12 g).

IR (Nujol): 3300, 1765 (br.), 1660, 1600 cm$^{-1}$

NMR (D$_2$O) δ: 3.80 (2H, br.s), 4.00 (3H, s), 4.40 (3H, s), 5.30 (1H, d, J=5 Hz), 5.83 (1H, d, J=5 Hz), 7.0 (2H, br.s), 7.13 (1H, s), 8.53 (1H, d, J=4 Hz), 8.90 (1H, br.s), 9.10 (1H, m).

EXAMPLE 9

The following compounds were obtained according to a similar manner to that of Example 8.

(1) 7-[2-Methoxyimino-2-(2-aminothiazol-4-yl)acetamido]-3-[2-(1-methyl-3-pyridinio)thiovinyl]-3-cephem-4-carboxylate (syn isomer)(trans isomer).

IR (Nujol): 3400–3100 (broad), 1760, 1660, 1600, 1520 cm$^{-1}$.

(2) 7-[2-Methoxyimino-2-(2-aminothiazol-4-yl)acetamido-3-[2-(1-methyl-2-pyridinio)thiovinyl)-3-cephem-4-carboxylate (syn isomer)(trans isomer).

IR (Nujol): 3300, 1765, 1670, 1611, 1562, 1533 cm$^{-1}$

NMR (D$_2$O-DCl) δ: 4.00 (2H, br.s), 4.13 (3H, s), 4.30 (3H, s), 5.37 (1H, d, J=5 Hz), 5.83i (1H, d, J=5 Hz), 7.00 (1H, d, J=16 Hz), 7.17 (1H, s), 7.63 (1H, d, J=16 Hz), 7.6–8.2 (2H, m), 8.33 (1H, dd, J=8 Hz), 8.73 (1H, d, J=8 Hz).

(3) 7-[2-Ethoxyimino-2-(5-amino-1,2,4-thiadiazol-3-yl)acetamido]-3-[2-(1-methyl-3-pyridinio)thiovinyl]-3-cephem-4-carboxylate (syn isomer)(trans isomer).

IR (Nujol): 3300 (broad), 1760, 1660, 1600, 1520 cm$^{-1}$.

(4) 7-[2-Ethoxyimino-2-(5-amino-1,2,4-thiadiazol-3-yl)acetamido]-3-[2-(1-methyl-2-pyridinio)thiovinyl]-3-cephem-4-carboxylate (syn isomer)(trans isomer).

IR (Nujol): 3300, 3200, 1760, 1650, 1600 cm$^{-1}$.

(5) 7-[2-Ethoxyimino-2-(5-amino-1,2,4-thiadiazol-3-yl)acetamido]-3-[2-(1,3-dimethyl-2-pyrimidinio)thiovinyl]-3-cephem-4-carboxylate iodide (syn isomer)(trans isomer).

IR (Nujol): 3350, 1770, 1663, 1605 cm$^{-1}$.

(6) 7-[2-Ethoxyimino-2-(5-amino-1,2,4-thiadiazol-3-yl)acetamido]-3-[2-(4-methyl-2-pyrazinio)thiovinyl]-3-cephem-4-carboxylate (syn isomer)(trans isomer).

IR (Nujol): 3350, 1760 (br.), 1665, 1607 cm$^{-1}$.

(7) 7-[2-Ethoxyimino-2-(5-amino-1,2,4-thiadiazol-3-yl)-acetamido]-3-[2-(1-methyl-2-pyridinio)thiovinyl]-3-cephem-4-carboxylate hydriodide (syn isomer)(trans isomer).

IR (Nujol): 3400, 3250, 1780, 1650–1680, 1620 cm$^{-1}$.

(8) 7-[2-Methoxyimino-2-(5-amino-1,2,4-thiadiazol-3-yl)acetamido]-3-[2-(1-methyl-2-pyridinio)thiovinyl]-3-cephem-4-carboxylate (syn isomer)(trans isomer).

IR (Nujol): 3250–3350, 1770, 1660, 1620, 1560, 1530 cm$^{-1}$.

(9) 7-[2-Ethoxyimino-2-(5-amino-1,2,4-thiadiazol-3-yl)acetamido]-3-[2-(1-ethyl-3-pyridinio)thiovinyl]-3-cephem-4-carboxylate (syn isomer)(trans isomer).

IR (Nujol): 3300 (broad), 1770, 1675, 1600. 1520 cm$^{-1}$.

(10) 7-[2-Ethoxyimino-2-(5-amino-1,2,4-thiadiazol-3-yl)acetamido]-3-[2-(1-methyl-3-pyridinio)thiovinyl]-3-cephem-4-carboxylate (syn isomer)(cis isomer).

IR (Nujol): 3300 (broad), 1760, 1665, 1600, 1520 cm$^{-1}$.

(11) 7-[2-Carboxymethoxyimino-2-(5-amino-1,2,4-thiadiazol-3-yl)acetamido]-3-[2-(1-methyl-3-pyridinio)-thiovinyl]-3-cephem-4-carboxylate (syn isomer)(trans isomer).

IR (Nujol): 3300 (broad), 1765, 1670, 1615, 1560, 1525 cm$^{-1}$.

(12) 7-[2-Allyloxyimino-2-(5-amino-1,2,4-thiadiazol-3-yl)acetamido]-3-[2-(1-methyl-3-pyridinio)thiovinyl]-3-cephem-4-carboxylate (syn isomer)(trans isomer).

IR (Nujol): 3300, 1760, 1670, 1620, 1600, 1530 cm$^{-1}$.

(13) 7-[2-(Tert-butoxycarbonylmethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3200–3300, 2400–2600, 1770, 1715, 1680, 1630 cm$^{-1}$

NMR (DMSO-d$_6$) δ: 1.50 (9H, s), 3.20–4.10 (2H, m), 4.43 (3H, s), 4.70 (2H, s), 5.30 (1H, d, J=5 Hz), 5.83 (1H, dd, J=5 Hz, 8 Hz), 7.00 (1H, s), 7.30 (2H, broad s), 8–9.00 (6H, m), 9.27 (1H, broad s), 9.77 (1H, d, J=8 Hz).

(14) 7-[2-Carboxymethoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1765, 1670, 1620 cm$^{-1}$

NMR (DMSO-d$_6$) δ: 3.50–4.10 (2H, m), 4.30 (3H, s), 4.63 (2H, broad s), 5.23 (1H, d, J=5 Hz), 5.90 (1H, dd, J=5 Hz, 8 Hz), 6.87 (1H, s), 6.95 (1H, d, J=15 Hz), 7.15 (2H, broad s), 7.47 (1H, d, J=15 Hz), 7.90–8.90 (3H, m), 9.13 (1H, broad s), 9.80 (1H, d, J=8 Hz).

(15) 7-[2-(3-Carboxy-2-propenyloxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535 cm$^{-1}$

NMR (DMSO-6/D$_2$O) δ: 3.57–4.20 (2H, m), 4.37 (3H, s), 4.57–4.93 (2H, m), 5.10 (1H, d, J=5 Hz), 5.60 (1H, dd, J=5 Hz, 8 Hz), 5.98 (1H, d, J=16 Hz), 6.51 (1H, d, J=16 Hz), 7.48 (1H, d, J=16 Hz), 6.78 (1H, s), 7.76–9.17 (4H, m), 9.67 (1H, d, J=8 Hz).

(16) 7-[2-(1-Methyl-2-pyridiniomethoxyimino)-2-(2-aminothiazol-4-yl)acetamido]-3-[2-(1-methyl-3-pyridinio)thiovinyl]-3-cephem-4-carboxylate iodide (syn isomer) (trans isomer).

IR (Nujol): 3250, 1760, 1665, 1615 cm$^{-1}$

NMR (D$_2$O) δ: 7.9–9.00 (8H, m), 7.17 (1H, d, J=16 Hz), 7.10 (1H, s), 6.67 (1H, d, J=16 Hz), 5.90 (1H, d, J=5 Hz), 5.75 (2H, s), 5.34 (1H, d, J=5 Hz), 4.45 (6H, s), 3.5–4.25 (2H, m).

(17) 7-[2-(2-Pyridylmethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1620, 1590 cm$^{-1}$

NMR (DMSO-d$_6$) δ: 3.7–4.20 (2H, m), 4.47 (3H, s), 5.15 (1H, d, J=5 Hz), 5.25 (2H, s), 5.72 (1H, dd, J=5 Hz, 8 Hz), 6.48 (1H, d, J=14 Hz), 6.80 (1H, s), 7.1–9.0 (11H, m), 9.90 (1H, d, J=8 Hz).

(18) 7-[2-(3-Carboxypropoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535 cm$^{-1}$

NMR (DMSO-d$_6$/D$_2$O) δ: 1.5–2.73 (4H, m), 3.3–4.27 (4H, m), 4.37 (3H, s), 5.08 (1H, d, J=5 Hz), 5.63 (1H, dd, J=5 Hz, 8 Hz), 6.50 (1H, d, J=16 Hz), 7.48 (1H, d, J=16 Hz), 6.74 (1H, s), 7.76–9.13 (4H, m), 9.55 (1H, d, J=8 Hz).

(19) 7-[2-(1-Carboxypropoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1590 cm$^{-1}$

NMR (DMSO-d$_6$) δ: 1.08 (3H, t, J=7 Hz), 1.62–2.24 (2H, m), 3.2–3.9 (2H, m), 4.42 (3H, s), 4.47 (1H, t, J=6 Hz), 5.15 (1H, d, J=5 Hz), 5.77 (1H, dd, J=8 Hz, 5 Hz), 6.47 (1H, d, J=16 Hz), 6.87 (1H, s), 7.0 (1H, d, J=16 Hz), 7.02–9.3 (4H, m).

(20) 7-[2-Allyloxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1530 cm$^{-1}$

NMR (DMSO-d$_6$/D$_2$O) δ: 3.33–3.87 (4H, m), 4.37 (3H, s), 4.62 (2H, d, J=5 Hz), 6.50 (1H, d, J=16 Hz), 7.47 (1H, d, J=16 Hz), 6.73 (1H, s), 7.83–9.03 (4H, m), 9.57 (1H, d, J=8 Hz).

(21) 7-[2-(2-Hydroxyethoxyimino)-2-(2-aminothiazol-4-yl)acetamido]-3-[2-(1-methyl-3-pyridinio)thiiovinyl]-3-cepthm-4-carboxylate (syn isomer) (trans isomer).

IR (Nujol): 3300, 1760, 1660, 1600, 1535, 1500 cm$^{-1}$

NMR (DMSO-d$_6$/D$_2$O) δ: 3.20–3.83 (2H, m), 4.35 (3H, s).

(22) 7-[2-Ethoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1665, 1600, 1535 cm$^{-1}$

NMR (DMSO-d$_6$/D$_2$O) δ: 1.25 (3H, t, J=7 Hz), 4.13 (2H, ABq, J=7 Hz), 4.37 (3H, s), 5.08 (1H, d, J=5 Hz), 5.65 (1H, dd, J=5 Hz, 8 Hz), 6.48 (1H, d, J=16 Hz), 7.48 (1H, d, J=16 Hz), 7.73–7.93 (4H, m), 9.52 (1H, d, J=8 Hz), 6.73 (1H, s).

(23) 7-[2-(2-Propynyloxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3250, 1760, 1660, 1600, 1530 cm$^{-1}$

NMR (DMSO-d$_6$/D$_2$O) δ: 3.3–3.8 (3H, m), 4.37 (3H, s), 4.7 (2H, s), 5.09 (1H, d, J=5 Hz), 5.63 (1H, dd, J=5 Hz, 8 Hz), 6.53 (1H, d, J=16 Hz), 6.78 (1H, s), 7.50 (1H, d, J=16 Hz), 7.73–7.93 (4H, m), 9.05 (1H, s), 9.52 (1H, d, J=8 Hz).

(24) 7-[2-Hydroxy-2-(2-aminothiazol-4-yl)acetamido]-3-[2-(1-methyl-3-pyridinio)thiovinyl]-3-cephem-4-carboxylate (trans isomer).

IR (Nujol): 3300, 1760, 1670, 1600 cm$^{-1}$

NMR (DMSO-d$_6$) δ: 3.42–4.04 (2H, m), 4.43 (3H, s), 5.00 (1H, s), 5.15 (1H, d, J=5 Hz), 5.70 (1H, dd, J=8 Hz, 5 Hz), 6.54 (1H, s), 6.6 (1H, d, J=16 Hz), 7.02 (2H, broad s), 7.53 (1H, d, J=16 Hz), 7.73–9.17 (4H, m).

(25) 7-[2-(1-Carboxy)ethoxyimino-2-(5-amino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3300, 1770, 1665, 1600, 1520 cm$^{-1}$

NMR (DMSO-d$_6$/D$_2$O) δ: 1.51 (3H, d, J=6 Hz), 3.80 (2H, broad s), 4.31 (3H, s), 4.75 (1H, d, J=6 Hz), 5.25 (1H, d, J=4 Hz), 5.85 (1H, d, J=4 Hz), 6.83 (1H, d, J=16 Hz), 7.50 (1H, d, J=16 Hz), 7.6–9.4 (4H, m).

(26) 7-[2-(1-Methyl-1-carboxyethoxyimino)-2-(5-amino-1,2,4-thiadiazol-3-yl)acetamido]-3-[2-(1-methyl-3-pyridinio)thiovinyl]-3-cephem-4-carboxylate (syn isomer) (trans isomer).

IR (Nujol): 3300, 1770, 1670, 1610, 1520 cm$^{-1}$

NMR (D$_2$O-NaHCO$_3$) δ: 1.60 (6H, s), 3.82 (2H, s), 4.42 (3H, s), 5.35 (1H, d, J=4 Hz), 5.90 (1H, d, J=4 Hz), 6.70 (1H, d, J=16 Hz), 7.20 (1H, d, J=16 Hz), 7.5–8.9 (3H, m).

(27) 7-[2-Ethoxyimino-2-(5-amino-1,2,4-thiadiazol-3-yl)acetamido]-3-[2-(1-carboxymethyl-3-pyridinio)thiovinyl]-3-cephem-4-carboxylate (syn isomer) (trans isomer).

IR (Nujol): 3300, 1760, 1640–1680, 1610, 1520 cm$^{-1}$

NMR (DMSO-d$_6$) δ: 1.30 (3H, t, J=5 Hz), 3.33–3.90 (2H, m), 4.25 (2H, q, J=7 Hz), 4.95–5.20 (3H, m), 5.75 (1H, m), 6.60 (1H, d, J=16 Hz), 7.50 (1H, d, J=16 Hz), 8.00–9.00 (4H, m), 9.55 (1H, d, J=8 Hz).

(28) 7-[2-Ethoxyimino-2-(5-amino-1,2,4-thiadiazol-3-yl)acetamido]-3-[2-(2-trimethylammonioethyl)thiovinyl]-3-cephem-4-carboxylate (syn isomer) (trans isomer).

IR (Nujol): 3300, 1760, 1670, 1600, 1520 cm$^{-1}$

NMR (DMSO-d$_6$) δ: 1.25 (3H, t, J=5 Hz), 3.10–4.00 (6H, m), 4.20 (2H, q, J=7 Hz), 5.05 (1H, d, J=5 Hz), 5.60 (1H, m), 6.60 (1H, d, J=16 Hz), 7.03 (1H, d, J=16 Hz), 8.06 (2H, broad s), 9.50 (1H, d, J=8 Hz).

(29) 7-[2-Methoxyimino-2-(2-aminothiazol-4-yl)acetamido]-3-[2-(1-methyl-2-pyridinio)thiovinyl]-3-cephem-4-carboxylate (syn isomer) (cis isomer).

IR (Nujol): 3400–3100, 1765, 1660, 1610, 1560, 1530 cm$^{-1}$

NMR (DMSO-d$_6$) δ: 3.67 (2H, ABq, J=16 Hz), 3.83 (3H, s), 4.17 (3H, s), 5.12 (1H, d, J=5 Hz), 5.63 (1H, dd, J=5 Hz, 8 Hz), 6.42 (1H, d, J=14 Hz), 6.73 (1H, s), 7.25 (2H, broad s), 7.63 (1H, d, J=14 Hz), 7.9–9.00 (4H, m), 9.57 (1H, d, J=8 Hz).

(30) 7-[(2-Methoxyimino-2-(2-aminothiazol-4-yl)acetamido]-3-[2-(1-methyl-3-pyridinio)thiovinyl-3-cephem-4-carboxylate (syn isomer) (cis isomer).

IR (Nujol): 3300, 1760, 1660, 1600, 1530 cm$^{-1}$

NMR (DMSO-d$_6$) δ: 3.72 (2H, ABq, J=16 Hz), 3.82 (3H, s), 4.33 (3H, s), 5.10 (1H, d, J=5 Hz), 5.63 (1H, dd, J=5 Hz, 8 Hz), 6.38 (1H, d, J=10 Hz), 6.73 (1H, s), 7.22 (1H, d, J=10 Hz), 7.18 (2H, broad s), 7.85–8.90 (3H, m), 9.17 (1H, broad s), 9.50 (1H, d, J=8 Hz).

(31) 7-[2-(3-Carboxypropoxyimino)-2-(5-amino-1,2,4-thiodiazol-3-yl)acetamido]-3-[2-(1-methyl-3-pyridinio)-thiovinyl]-3-cephem-4-carboxylate (syn isomer) (trans isomer).

IR (Nujol): 3300, 1765, 1665, 1600, 1530 cm$^{-1}$

NMR (DMSO-d$_6$) δ: 1.6–2.7 (4H, m), 3.75 (2H, broad s), 4.0–4.4 (2H, m), 4.40 (3H, s), 5.10 (1H, d, J=4 Hz), 5.72 (1H, dd, J=4, 8 Hz), 6.75 (1H, d, J=16 Hz), 7.44 (1H, d, J=16 Hz), 7.7–9.1 (4H, m), 9.60 (1H, d, J=8 Hz).

(32) 7-[2-Ethoxyimino-2-(5-amino-1,2,4-thiadiazol-3-yl)acetamido]-3-[2-(1-methyl-2-pyridinio)thiovinyl]-3-cephem-4-carboxylate (syn isomer) (cis isomer).

IR (Nujol): 3300, 1765, 1670, 1610, 1560 cm$^{-1}$

NMR (DMSO-d$_6$) δ: 1.27 (3H, t, J=5 Hz), 3.65–4.35 (4H, m), 5.10 (1H, J=5 Hz), 5.68 (1H, dd, J=5 Hz, 8 Hz), 6.42 (1H, d, J=14 Hz), 7.67 (1H, d, J=14 Hz), 6.95–9.00 (6H, m), 9.50 (1H, d, J=8 Hz).

EXAMPLE 10

To a mixture of anisole (10 ml) and trifluoroacetic acid (8 ml) was portionwise added 7-[2-(tert-butoxycarbonylmethoxyimino)-2-(2-aminothiazol-4-yl)acetamido]-3-[2-(1-methyl-3-pyridinio)thiovinyl]-3-cephem-4-carboxylate hydrochloride (syn isomer) (trans isomer) (1.2 g). The mixture was stirred at 25° C. for an hour and added to diisopropyl ether to afford precipitate. The precipitate was collected by filtration and dissolved in water at pH 5.0. The aqueous solution was subjected to column chromatography on macroporous non-ionic resin "Diaion HP-20", and eluted with 7% aqueous solution of isopropyl alcohol. The fractions containing the object compound were concentrated in vacuo and lyophilized to give 7-[2-carboxymethoxyimino-2-(2-aminothiazol-4-yl)acetamido]-3-[2-(1-methyl-3-pyridinio)thiovinyl]-3-cephem-4-carboxylate (syn isomer) (trans isomer) (0.55 g).

IR (Nujol): 3300, 1765, 1670, 1620 cm$^{-1}$

NMR (DMSO-d$_6$) δ: 3.50–4.10 (2H, m), 4.30 (3H, s), 4.63 (2H, broad s), 5.23 (1H, d, J=5 Hz), 5.90 (1H, dd, J=5 Hz, 8 Hz), 6.87 (1H, s), 6.95 (1H, d, J=15 Hz), 7.15 (2H, broad s), 7.47 (1H, d, J=15 Hz), 7.90–8.90 (3H, m), 9.13 (1H, broad s), 9.80 (1H, d, J=8 Hz).

EXAMPLE 11

The following compounds were obtained according to a similar manner to that of Example 10.

(1) 7-[2-(3-Carboxy-2-propenyloxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535 cm$^{-1}$.

(2) 7-[2-(3-Carboxypropoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535 cm$^{-1}$.

(3) 7-[2-(1-Carboxypropoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1590 cm$^{-1}$.

(4) 7-[2-Carboxymethoxyimino-2-(thiazol-4-yl)acetamido]-3-[2-(1-methyl-3-pyridinio)thiovinyl]-3-cephem-4-carboxylate (syn isomer) (trans isomer).

IR (Nujol): 3350, 1760, 1660, 1600 cm$^{-1}$.

(5) 7-[2-(1-Carboxy)ethoxyimino-2-(5-amino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3300, 1770, 1665, 1600, 1520 cm$^{-1}$.

(6) 7-[2-(1-Methyl-1-carboxyethoxyimino)-2-(5-amino-1,2,4-thiadiazol-3-yl)acetamido]-3-[2-(1-methyl-3-pyridinio)thiovinyl]-3-cephem-4-carboxylate (syn isomer) (trans isomer).

IR (Nujol): 3300, 1770, 1670, 1610, 1520 cm$^{-1}$.

(7) 7-[2-(3-Carboxypropoxyimino)-2-(5-amino-1,2,4-thiodiazol-3-yl)acetamido]-3-[2-(1-methyl-3-pyridinio)-thiovinyl]-3-cephem-4-carboxylate (syn isomer) (trans isomer).

IR (Nujol): 3300, 1765, 1665, 1600, 1530 cm$^{-1}$.

(8) 7-[2-Carboxymethoxyimino-2-(5-amino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3300 (broad), 1765, 1670, 1615, 1560, 1525 cm$^{-1}$.

EXAMPLE 12

A mixture of 7-[2-(2-pyridylmethoxyimino)-2-(2-formamidothiazol-4-yl)acetamido]-3-[2-(1-methyl-3-pyridinio)thiovinyl]-3-cephem-4-carboxylate (syn isomer) (trans isomer) (1.5 g) and methyl iodide (2 ml) in a mixture of N-N-dimethylformamide (25 ml) and water (10 ml) was stirred at room temperature for 3 days. After the reaction mixture containing 7-[2-(1-methyl-2-pyridiniomethoxyimino)-2-(2-formamidothiazol-4-yl)acetamido]-3-[2-(1-methyl-3-pyridinio)thiovinyl]-3-cephem-4-carboxylate iodide (syn isomer) (trans isomer) was evaporated to dryness in vacuo, methanol (50 ml) and concentrated hydrochloric acid (2 ml) were added to the residue. The mixture was stirred for four hours at room temperature and evaporated to dryness in vacuo. The residue was dissolved in water and subjected to column chromatography on macroporous non-ionic adsorption resin "Diaion HP-20" in a usual manner to give 7-[2-(1-methyl-2-pyridiniomethoxyimino)-2-(2-aminothiazol-4-yl)acetamido]-3-[2-(1-methyl-3-pyridinio)thiovinyl]-3-cephem-4-carboxylate (syn isomer) (trans isomer) (0.5 g).

IR (Nujol): 3250, 1760, 1665, 1615 cm$^{-1}$

NMR (D$_2$O) δ: 7.9–9.00 (8H, m), 7.17 (1H, d, J=16 Hz), 7.10 (1H, s), 6.67 (1H, d, J=16 Hz), 5.90 (1H, d,

J=5 Hz), 5.75 (2H, s), 5.34 (1H, d, J=5 Hz), 4.45 (6H, s), 3.5-4.25 (2H, m).

EXAMPLE 13

To a mixture of benzhydryl 7-[2-ethoxyimino-2-(5-amino-1,2,4-thiadiazol-3-yl)acetamido]-3-[2-(1-benzhydryloxycarbonylmethyl-3-pyridinio)thiovinyl]-3-cephem-4-carboxylate bromide (syn isomer) (trans isomer) (1 g) in a mixture of $CH_2Cl_2$ (3 ml) and anisole (5 ml) was dropwise added trifluoroacetic acid at 5° C. with stirring. The reaction mixture was stirred for 2 hours at room temperature and poured into diisopropyl ether to give precipitate. The purification by column chromatography on macroporous non-ionic adsorption resin "Diaion HP-20" in a usual manner afforded 7-[2-ethoxyimino-2-(5-amino-1,2,4-thiadiazol-3-yl)acetamido]-3-[2-(1-carboxymethyl-3-pyridinio)thiovinyl]-3-cephem-4-carboxylate (syn isomer) (trans isomer) (0.35 g).

IR (Nujol): 3300, 1760, 1640-1680, 1610, 1520 cm$^{-1}$

NMR (DMSO-d$_6$) δ: 1.30 (3H, t, J=5 Hz), 3.33-3.90 (2H, m), 4.25 (2H, q, J=7 Hz), 4.95-5.20 (3H, m), 5.75 (1H, m), 6.60 (1H, d, J=16 Hz), 7.50 (1H, d, J=16 Hz), 8.00-9.00 (4H, m), 9.55 (1H, d, J=8 Hz).

EXAMPLE 14

To a solution of 7-[2-ethoxyimino-2-(5-amino-1,2,4-thiadiazol-3-yl)acetamido-3-ethynyl-3-cephem-4-carboxylic acid (syn isomer) (200 mg) in a mixture of acetonitrile (2 ml) and water (1 ml) was added 3-mercapto-1-methylpyridinium chloride (97 mg) at room temperature adjusting to pH 3.0 with a saturated aqueous solution of sodium bicarbonate. The reaction mixture was stirred for two and a half hours and then added ethyl acetate (10 ml) and water (10 ml). The separated aqueous layer was evaporated to remove organic solvents and subjected to columnn chromatography on a non ionic resin "HP-20" (50 ml). After washing water the column was eluted with 30% aqueous methanol and the elute was evaporated to remove methanol and the remaining aqueous solution was lyophilized to give 7-[2-ethoxyimino-2-(5-amino-1,2,4-thiadiazol-3-yl)acetamido]-3-[2-(1-methyl-3-pyridinio)thiovinyl]-3-cephem-4-carboxylate (syn isomer) (cis-trans mixture) (110 mg).

mp: 150°-155° C. (dec.)

IR (Nujol): 3300, 1760, 1670,, 1600, 1520 cm$^{-1}$

NMR (DMSO-d$_6$) δ: 1.32 (3H, t, J=7 Hz), 3.75 (2H, broad s), 4.23 (2H, q, J=7 Hz), 4.38 (3H, s), 5.08 (1H, d, J=5 Hz), 5.67 (1H, 2d, J=5 Hz, 8 Hz),

| 6.35 (d, J = 10Hz) | } 1H, | 7.30 (d, J = 10Hz) | } 1H, |
|---|---|---|---|
| 6.53 (d, J = 15Hz) | | 7.50 (d, J = 15Hz) | |
| 8.20 (2H, broad s), 8.00 (1H, m), 8.50 (1H, d), | | | |
| 8.80 (1H, d), | 9.00 (s) } 1H, 9.13 (s) | 9.40 (d, J = 8Hz) 9.50 (d, J = 8Hz) | } 1H |

EXAMPLE 15

To a mixture of 1-(3-N,N-dimethylaminopropyl)-3-mercaptopyridinium chloride hydrochloride (1.08 g) and diisopropyl ethylamine (0.5 ml) in N,N-dimethylformamide (11 ml) was added 7-{2-ethoxyimino-2-(5-amino-1,2,4-thiadiazol-3-yl)acetamido}-3-(2-tosyloxyvinyl)-3-cephem-4-carboxylic acid (syn isomer) (cis isomer) (1.18 g) at room temperature. After being stirred for 2 hours and 45 minutes, the reaction mixture was poured into ethyl acetate (150 ml). The resulting precipitates were collected by filtration and washed with ethyl acetate. The wet residue was dissolved in water and evaporated to remove ethyl acetate. The aqueous solution was adjusted to pH 3.5 with aqueous sodium bicarbonate, subjected to column chromatography on non-ionic resin "Diaion-HP-20", and eluted with 25% aqueous methanol. The fractions containing the object compound were combined and 1N hydrochloric acid (1.2 ml) was added thereto. The acidic solution was concentrated and lyophilized to give 7-[2-ethoxyimino-2-(5-amino-1,2,4-thiadiazol-3-yl)acetamido]-3-{2-[1-(3-N,N-dimethylaminopropyl)-3-pyridinio]thiovinyl}-3-cephem-4-carboxylate hydrochloride (syn isomer) (cis isomer) (0.75 g).

IR (Nujol): 1770, 1665, 1620, 1520 cm$^{-1}$

NMR (D$_2$O) δ: 1.35 (3H, t, J=7 Hz), 2.57 (2H, m), 2.95 (6H, s), 3.30 (2H, m), 3.80 (2H, br. s), 4.37 (2H, q, J=7 Hz), 5.30 (1H, d, J=5 Hz), 5.88 (1H, d, J=5 Hz), 6.60 (1H, d, J=10 Hz), 6.97 (1H, d, J=10 Hz), 8.00 (1H, dd, J=5 Hz, 8 Hz), 8.47 (1H, d, J=8 Hz), 8.93 (1H, d, J=5 Hz), 8.86 (1H, br. s).

EXAMPLE 16

The following compounds were obtained according to a similar manner to that of Example 15.

(1) 7-[2-Allyloxyimino-2-(2-aminothiazol-4-yl)acetamido]-3-{2-[1-(3-aminopropyl)-3-pyridinio]thiovinyl}-3-cephem-4-carboxylate hydrochloride (syn isomer) (cis isomer).

IR (Nujol): 3300, 1768, 1663,, 1619 cm$^{-1}$

NMR (D$_2$O) δ: 2.50 (2H, m), 3.20 (2H, m), 3.72 (2H, broad s), 4.80 (2H, m), 5.23 (1H, d, J=5 Hz), 5.43 (2H, m), 5.78 (1H, d, J=5 Hz), 5.8 (1H, m), 6.46, 6.86 (2H, ABq, J=10 Hz), 7.03 (1H, s), 7.95 (1H, dd, J=6 Hz, 8 Hz), 8.46 (1H, d, J=8 Hz), 8.68 (1H, d, J=6 Hz), 8.80 (1H, br. s).

(2) 7-[2-Methoxyimino-2-(2-aminothiazol-4-yl)acetamido]-3-{2-[1-(3-aminopropyl)-3-pyridinio]thiovinyl}-3-cephem-4-carboxylate hydrochloride (syn isomer) (cis isomer).

NMR (D$_2$O) δ: 2.58 (2H, m), 3.23 (2H, m), 3.80 (2H, broad s), 4.08 (3H, s), 4.83 (2H, m), 5.27 (1H, d, J=5 Hz), 5.80 (1H, d, J=5 Hz), 6.80 (2H, ABq, J=10 Hz), 7.15 (1H, s), 8.0 (1H, dd, J=6 Hz, 8 Hz), 8.47 (1H, d, J=8 Hz), 8.77 (1H, d, J=6 Hz), 8.87 (1H, broad s).

(3) 7-[2-Ethoxyimino-2-(5-amino-1,2,4-thiadiazol-3-yl)acetamido]-3-{2-[1-(2-aminoethyl)-3-pyridinio]thiovinyl}-3-cephem-4-carboxylate hydrochloride (syn isomer) (cis isomer).

mp: 115°-124° C. (dec.)

IR (Nujol): 1770, 1670, 1620, 1520 cm$^{-1}$

NMR (D$_2$O) δ: 1.34 (3H, t, J=7 Hz), 3.60-3.90 (4H, m), 4.38 (2H, q, J=7 Hz), 4.98 (2H, t, J=7 Hz), 5.30 (1H, d, J=5 Hz), 5.87 (1H, d, J=5 Hz), 6.63 (1H, d, J=10 Hz), 6.93 (1H, d, J=10 Hz), 8.03 (1H, dd, J=9 Hz, 6 Hz), 8.53 (1H, d, J=9 Hz), 8.78 (1H, d, J=6 Hz), 8.90 (1H, br.s).

(4) 7-[2-Ethoxyimino-2-(5-amino-1,2,4-thiadiazol-3-yl)acetamido]-3-{2-[1-(2-aminoethyl)-3-pyridinio]thiovinyl}-3-cephem-4-carboxylate hydrochloride (syn isomer) (trans isomer).

mp: 113°-122° C. (dec.)

IR (Nujol): 3320, 1765, 1660, 1620, 1520 cm$^{-1}$

NMR (D$_2$O) δ: 1.33 (3H, t, J=7 Hz), 3.60-3.96 (4H, m), 4.35 (2H, q, J=7 Hz), 5.00 (2H, t, J=7 Hz), 5.28 (1H, d, J=5 Hz), 5.82 (1H, d, J=5 Hz), 6.87 (1H, d, J=15 Hz), 7.30 (1H, d, J=15 Hz), 8.03 (1H, dd, J=9

Hz, 6 Hz), 8.55 (1H, d, J=9 Hz), 8.79 (1H, d, J=6 Hz), 8.94 (1H, br.s).

(5) 7-[2-Ethoxyimino-2-(5-amino-1,2,4-thiadiazol-3-yl)acetamido]-3-{2-[1-(2-N,N-dimethylaminoethyl)-3-pyridinio]thiovinyl}-3-cephem-4-carboxylate hydrochloride (syn isomer) (cis isomer).

IR (Nujol): 3300, 1760, 1670, 1610, 1520 cm$^{-1}$

NMR (D$_2$O) δ: 1.35 (3H, t, J=7 Hz), 3.04 (6H, s), 3.67–4.07 (4H, m), 4.38 (2H, q, J=7 Hz), 4.97 (2H, t, J=7 Hz), 5.28 (1H, d, J=5 Hz), 5.85 (1H, d, J=5 Hz), 6.53 (1H, d, J=10 Hz), 6.92 (1H, d, J=10 Hz), 8.00 (1H, m), 8.38–8.96 (m, 3H).

(6) 7-[2-Methoxyimino-2-(2-aminothiazol-4-yl)acetamido]-3-{2-[1-(3-N,N-dimethylaminopropyl)-3-pyridinio]thiovinyl}-3-cephem-4-carboxylate hydrochloride (syn isomer) (trans isomer).

NMR (D$_2$O) δ: 2.55 (2H, m), 2.92 (6H, s), 3.30 (2H, m), 3.77 (2H, broad s), 4.07 (3H, s), 3.85 (2H, m), 5.27 (1H, d, J=5 Hz), 5.77 (1H, d, J=5 Hz), 6.95 (2H, ABq, J=15 Hz), 7.12 (1H, s), 8.0 (1H, dd, J=6 Hz, 8 Hz), 8.50 (1H, d, J=8 Hz), 8.73 (1H, d, J=6 Hz), 8.85 (1H, broad s).

(7) 7-[2-Methoxyimino-2-(2-aminothiazol-4-yl)acetamido]-3-{2-[1-(2-aminoethyl)-3-pyridinio]thiovinyl}-3-cephem-4-carboxylate hydrochloride (syn isomer) (trans isomer).

NMR (D$_2$O) δ: 3.72 (2H, t, J=7 Hz), 3.75 (2H, broad s), 4.03 (3H, s), 4.97 (2H, t, J=7 Hz), 5.27 (1H, d, J=5 Hz), 5.77 (1H, d, J=5 Hz), 6.87 (2H, ABq, J=15 Hz), 7.05 (1H, s), 8.0 (1H, dd, J=6 Hz, 8 Hz), 8.52 (1H, d, J=8 Hz), 8.72 (1H, d, J=6 Hz), 8.85 (1H, broad s).

(8) 7-[2-Methoxyimino-2-(2-aminothiazol-4-yl)acetamido]-3-{2-[1-(3-N,N-dimethylaminopropyl)-3-pyridinio]thiovinyl}-3-cephem-4-carboxylate hydrochloride (syn isomer) (cis isomer).

NMR (D$_2$O) δ: 2.50 (2H, m), 3.33 (2H, m), 3.73 (2H, broad s), 4.0 (3H, s), 4.50–4.77 (2H, m), 5.25 (1H, d, J=5 Hz), 5.78 (1H, dd, J=5 Hz), 6.67 (2H, ABq, J=10 Hz), 6.95 (1H, s), 7.92 (1H, dd, J=6 Hz, 8 Hz), 8.43 (1H, d, J=8 Hz), 8.68 (1H, d, J=6 Hz), 8.82 (1H, broad s).

(9) 7-[2-Methoxyimino-2-(2-aminothiazol-4-yl)acetamido]-3-{2-[1-(3-aminopropyl)-3-pyridinio]thiovinyl}-3-cephem-4-carboxylate hydrochloride (syn isomer) (trans isomer).

IR (Nujol): 1770, 1670, 1620, 1560 cm$^{-1}$

NMR (D$_2$O) δ: 2.53 (2H, m), 3.18 (2H, m), 3.80 (2H, broad s), 4.07 (3H, s), 4.82 (2H, m), 5.27 (1H, d, J=5 Hz), 5.77 (1H, d, J=5 Hz), 7.05 (1H, dd, J=15 Hz), 8.0 (1H, dd, J=6 Hz, 8 Hz), 8.50 (1H, d, J=8 Hz), 8.73 (1H, d, J=6 Hz), 8.87 (1H, broad s).

(10) 7-[2-Allyloxyimino-2-(2-aminothiazol-4-yl)acetamido]-3-{2-[1-(2-aminoethyl)-3-pyridinio]thiovinyl}-3-cephem-4-carboxylate hydrochloride (syn isomer) (cis isomer).

IR (Nujol): 3350, 1770, 1660, 1620 cm$^{-1}$

NMR (D$_2$O) δ: 3.70 (2H, br. s), 3.72 (2H, t, J=7 Hz), 4.80 (2H, m), 4.97 (2H, t, J=7 Hz), 5.23 (1H, d, J=5 Hz), 5.45 (2H, m), 5.80 (1H, d, J=5 Hz), 5.90 (1H, m), 6.46 and 6.88 (2H, ABq, J=10 Hz), 7.02 (1H, s), 7.98 (1H, dd, J=6 Hz, 8 Hz), 8.50 (1H, d, J=8 Hz), 8.74 (1H, d, J=6 Hz), 8.83 (1H, br. s).

(11) 7-[2-Allyloxyimino-2-(2-aminothiazol-4-yl)acetamido]-3-{2-[1-(3-N,N-dimethylaminopropyl)-3-pyridinio]thiovinyl}-3-cephem-4-carboxylate hydrochloride (syn isomer) (trans isomer).

IR (Nujol): 3350, 1770, 1660, 1613 cm$^{-1}$

NMR (D$_2$O) δ: 3.50 (2H, m), 2.93 (6H, s), 3.30 (2H, m), 3.77 (2H, br. s), 4.83 (2H, m), 5.27 (1H, d, J=5 Hz), 5.4 (2H, m), 5.80 (1H, d, J=5 Hz), 5.9 (1H, m), 6.63, 7.10 (2H, ABq, J=15 Hz), 7.10 (1H, s), 7.98 (1H, dd, J=6 Hz, 8 Hz), 8.50 (1H, d, J=8 Hz), 8.70 (1H, d, J=6 Hz), 8.84 (1H, br. s).

(12) 7-[2-Allyloxyimino-2-(2-aminothiazol-4-yl)acetamido]-3-{2-[1-(2-aminoethyl)-3-pyridino]thiovinyl}-3-cephem-4-carboxylate hydrochloride (syn isomer) (trans isomer).

IR (Nujol): 3350, 1768, 1660, 1627 cm$^{-1}$

NMR (D$_2$O) δ: 3.75 (2H, t, J=7 Hz), 3.80 (2H, br. s), 4.8 (2H, m), 5.00 (2H, t, J=7 Hz), 5.30 (1H, d, J=5 Hz), 5.45 (2H, m), 5.82 (1H, d, J=5 Hz), 5.9 (1H, m), 6.72 and 7.18 (2H, ABq, J=16 Hz), 7.15 (1H, s), 8.05 (1H, dd, J=6 Hz, 8 Hz), 8.60 (1H, d, J=8 Hz), 8.80 (1H, d, J=6 Hz), 8.93 (1H, br. s).

(13) 7-[2-Methoxyimino-2-(5-amino-1,2,4-thiadiazol-3-yl)acetamido]-3-{2-[1-(3-aminopropyl)-3-pyridinio]thiovinyl}-3-cephem-4-carboxylate hydrochloride (syn isomer) (trans isomer).

mp: 185°–190° C. (dec.)

IR (Nujol): 3350, 3150, 1765, 1670, 1615, 1595, 1560, 1525, 1490 cm$^{-1}$

NMR (D$_2$O) δ: 2.40–2.70 (2H, m), 3.0–3.40 (2H, m), 3.72 (2H, br. s), 4.05 (3H, s), 4.40–4.90 (2H, m), 5.23 (1H, d, J=5 Hz), 5.82 (1H, d, J=5 Hz), 6.68 (1H, d, J=16 Hz), 7.15 (1H, d, J=16 Hz), 7.77–8.10 (1H, m), 8.23–8.50 (1H, m), 8.57–8.87 (2H, m).

(14) 7-[2-Carboxymethoxyimino-2-(2-aminothiazol-4-yl)acetamido]-3-{2-[1-(3-aminopropyl)-3-pyridinio]thiovinyl}-3-cephem-4-carboxylate hydrochloride (syn isomer) (cis isomer).

IR (Nujol): 3350, 1780, 1710, 1673, 1627 cm$^{-1}$

NMR (D$_2$O) δ: 2.30 (2H, m), 3.14 (2H, m), 3.80 (2H, m), 4.7 (2H, br. s), 4.86 (2H, m), 5.10 (1H, d, J=5 Hz), 6.05 (1H, d, J=5 Hz), 6.57, 6.85 (2H, ABq, J=10 Hz), 7.20 (1H, s), 7.91 (1H, dd, J=6 Hz, 8 Hz), 8.45 (1H, d, J=8 Hz), 8.65 (1H, d, J=6 Hz), 8.80 (1H, br. s).

EXAMPLE 17

A mixture of benzhydryl 7-[2-allyloxyimino-2-(5-amino-1,2,4-thiadiazol-3-yl)acetamido]-3-(2-tosyloxyl-vinyl)-3-cephem-4-carboxylate (syn isomer) (trans isomer) (5.0 g), 1-(3-aminopropyl)-3-mercaptopyridinium chloride hydrochloride (4.0 g) and diisopropylethylamine (0.6 ml) in N,N-dimethylformamido (40 ml) was stirred for 5 hours at room temperature. The reaction mixture was diluted with ethyl acetate (250 ml) and decanted. The residual oil was washed with methylene chloride (100 ml) and dried in vacuo. To the residue was added anisole (15 ml) and trifluoroacetic acid (20 ml) was added thereto under cooling in an ice-bath. After being stirred for 40 minutes, the reaction mixture was poured into ethyl acetate (200 ml). The resulting precipitates were collected by filtration, washed with ethyl acetate, dissolved in water and evaporated to remove ethyl acetate under reduced pressure. The aqueous solution was adjusted to pH 1 with aqueous sodium bicarbonate, subjected to column chromatography on non-ionic resin "Diaion-HP-20" and eluted with 30% aqueous methanol. The fractions containing the object compound were combined and 1N hydrochloric acid (3 ml) was added thereto. The acidic solution was concentrated and lyophilized to give 7-[2-allyloxyimino-2-(5-amino-1,2,4-thiadiazol-3-yl)acetamido]-3-{2-[1-(3-aminopropyl)-3-pyridinio]thiovinyl}-3-cephem-4-carboxylate dihydrochloride (syn isomer) (trans isomer) (1.48 g).

mp: 164°–168° C. (dec.)

IR (Nujol): 3400–3100, 1770, 1710, 1670, 1620, 1530 cm$^{-1}$

NMR (D$_2$O) δ: 2.53 (2H, m), 3.21 (2H, m), 3.80 (2H, m), 5.29 (1H, d, J=5 Hz), 5.3–5.7 (2H, m), 5.87 (1H, d, J=5 Hz), 5.7–6.3 (1H, m), 6.90 (1H, d, J=15 Hz), 7.31 (1H, d, J=15 Hz), 8.1 (1H, d, J=6 Hz), 8.50 (1H, m), 8.80 (1H, d, J=6 Hz), 8.93 (1H, s).

EXAMPLE 18

The following compounds were obtained according to a similar manner to that of Example 17.

(1) 7-[2-Allyloxyimino-2-(5-amino-1,2,4-thiadiazol-3-yl)acetamido]-3-{2-[1-(3-N,N-dimethylaminopropyl)-3-pyridinio]thiovinyl}-3-cephem-4-carboxylate hydrochloride (syn isomer) (trans isomer).

mp: 70°–75° C. (dec.)

IR (Nujol): 3300, 2700, 1760, 1660, 1610, 1520 cm$^{-1}$

NMR (DMSO-d$_6$) δ: 2.20–2.60 (2H, m), 2.73 (3H, s), 2.80 (3H, s), 2.90–3.30 (2H, m), 3.70–3.90 (2H, m) 4.0–5.0 (4H, m), 5.0–5.53 (3H, m), 5.87 (1H, dd, J=5 Hz, 8 Hz), 5.70–6.20 (1H, m), 7.23 (2H, s), 7.87–8.27 (3H, m), 8.50–8.80 (1H, m), 8.97–9.20 (1H, m), 9.30–9.43 (1H, br. s), 9.63 (1H, d, J=8 Hz).

(2) 7-[2-Allyloxyimino-2-(5-amino-1,2,4-thiadiazol-3-yl)acetamido]-3-{2-[1-(2-aminoethyl)-3-pyridinio]thiovinyl}-3-cephem-4-carboxylate dihydrochloride (syn isomer) (cis isomer).

mp: 125°–130° C. (dec.)

IR (Nujol): 1765, 1670, 1605, 1510 cm$^{-1}$

NMR (D$_2$O) δ: 3.77 (4H, m), 4.97 (2H, t, J=7 Hz), 5.28 (1H, d, J=5 Hz), 5.2–5.7 (2H, m), 5.83 (1H, d, J=5 Hz), 5.8–6.3 (1H, m), 6.60 (1H, d, J=10 Hz), 6.93 (1H, d, J=10 Hz), 8.05 (1H, m), 8.50 (1H, m), 8.78 (1H, d, J=6 Hz), 8.87 (1H, br. s).

(3) 7-[2-Allyloxyimino-2-(5-amino-1,2,4-thiadiazol-3-yl)acetamido]-3-{2-[1-(3-N,N-dimethylaminopropyl)-3-pyridinio]thiovinyl}-3-cephem-4-carboxylate hydrochloride (syn isomer) (cis isomer).

mp: 65°–70° C. (dec.)

IR (Nujol): 3350, 2700, 1765, 1670, 1600, 1525 cm$^{-1}$

NMR (D$_2$O) ppm δ: 2.30–2.80 (2H, m), 2.97 (6H, s), 3.13–3.53 (2H, m), 3.77 (2H, br. s), 4.60–5.0 (4H), 5.10–5.60 (3H, m), 5.80–6.40 (2H, m), 6.53 (1H, d, J=10 Hz), 6.93 (1H, d, J=10 Hz), 7.83–8.15 (1H, m), 8.30–8.60 (1H, m), 8.60–8.98 (2H, m).

(4) 7-[2-Allyloxyimino-2-(5-amino-1,2,4-thiadiazol-3-yl)acetamido]-3-{2-[1-(3-aminopropyl)-3-pyridinio]thiovinyl}-3-cephem-4-carboxylate hydrochloride (syn isomer) (cis isomer).

mp: 65°–70° C. (dec.)

IR (Nujol): 3350, 3150, 1770, 1710, 1670, 1620, 1525 cm$^{-1}$

NMR (D$_2$O) δ: 2.20–2.70 (2H, m), 2.90–3.40 (2H, m), 3.77 (2H, br. s), 4.40–5.0 (4H), 5.10–5.60 (3H, m), 5.60–6.30 (2H, m), 6.60 (1H, d, J=10 Hz), 6.92 (1H, d, J=10 Hz), 7.77–8.17 (1H, m), 8.20–8.53 (1H, m), 8.63–8.92 (2H, m).

(5) 7-[2-Allyloxyimino-2-(5-amino-1,2,4-thiadiazol-3-yl)acetamido]-3-{2-[1-(2-aminoethyl)-3-pyridinio]thiovinyl}-3-cephem-4-carboxylate dihydrochloride (syn isomer) (trans isomer).

mp: 170°–175° C. (dec.)

IR (Nujol): 1760, 1670, 1620 cm$^{-1}$

NMR (D$_2$O) δ: 3.71 (4H, m), 4.95 (2H, t, J=7 Hz), 5.36 (1H, d, J=5 Hz), 5.3–5.6 (2H, m), 5.82 (1H, d, J=5 Hz), 5.7–6.2 (1H, m), 6.84 (1H, d, J=15 Hz), 7.29 (1H, d, J=15 Hz), 8.01 (1H, m), 8.50 (1H, m), 8.77 (1H, d, J=6 Hz), 8.91 (1H, s).

(6) 7-[2-Ethoxyimino-2-(5-amino-1,2,4-thiadiazol-3-yl)acetamido]-3-{2-[1-(3-aminopropyl)-3-pyridinio]thiovinyl}-3-cephem-4-carboxylate hydrochloride (syn isomer) (cis isomer).

mp: 116°–126° C. (dec.)

IR (Nujol): 1770, 1670, 1610, 1510 cm$^{-1}$

NMR (D$_2$O) δ: 1.31 (3H, t, J=7 Hz), 2.00–2.80 (2H, m), 2.98–3.33 (2H, m), 3.73 (2H, br. s), 4.33 (2H, q, J=7 Hz), 5.25 (1H, d, J=5 Hz), 5.83 (1H, d, J=5 Hz), 6.53 (1H, d, J=10 Hz), 6.87 (1H, d, J=10 Hz), 7.77–8.15 (1H, m), 8.33–8.90 (3H, m).

(7) 7-[2-Ethoxyimino-2-(5-amino-1,2,4-thiadiazol-3-yl)acetamido]-3-{2-[1-(3-aminopropyl)-3-pyridinio]thiovinyl}-3-cephem-4-carboxylate hydrochloride (syn isomer) (trans isomer).

mp: 148°–157° C. (dec.)

IR (Nujol): 1770, 1670, 1620, 1530 cm$^{-1}$

NMR (D$_2$O) δ: 1.33 (3H, t, J=7 Hz), 2.17–2.80 (2H, m), 3.03–3.40 (2H, m), 3.83 (2H, br. s), 4.35 (2H, q, J=7 Hz), 5.28 (1H, d, J=5 Hz), 5.83 (1H, d, J=5 Hz), 6.92 (1H, d, J=16 Hz), 7.28 (1H, d, J=16 Hz), 8.01 (1H, dd, J=9 Hz, 6 Hz), 8.53 (1H, d, J=9 Hz), 8.86 (1H, d, J=6 Hz), 8.92 (1H, br. s).

(8) 7-[2-Ethoxyimino-2-(5-amino-1,2,4-thiadiazol-3-yl)acetamido]-3-{2-[1-(3-N,N-dimethylaminopropyl)-3-pyridinio]thiovinyl}-3-cephem-4-carboxylate hydrochloride (syn isomer) (trans isomer)

mp: 121°–130° C. (dec.)

IR (Nujol): 3350, 2700, 1770, 1670, 1620, 1530 cm$^{-1}$

NMR (D$_2$O) δ: 1.31 (3H, t, J=7 Hz), 2.26–2.83 (2H, m), 2.90 (6H, s), 3.13–3.50 (2H, m), 3.78 (2H, br. s), 4.33 (2H, q, J=7 Hz), 5.26 (1H, d, J=5 Hz), 5.78 (1H, d, J=5 Hz), 6.80 (1H, d, J=16 Hz), 7.17 (1H, d, J=16 Hz), 7.98 (1H, dd, J=8 Hz, 6 Hz), 8.50 (1H, d, J=8 Hz), 8.72 (1H, d, J=6 Hz), 8.86 (1H, br. s).

EXAMPLE 19

The following compound was obtained according to a similar manner to that of Example 10.

7-[2-(1-Carboxy-1-cyclopentyloxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1650, 1590 cm$^{-1}$

NMR (DMSO-d$_6$) δ: 1.73–2.3 (8H, m), 3.8 (2H, br.) 4.3 (3H, s), 5.3 (2H, d, J=5 Hz), 5.7 (1H, d, J=5 Hz), 6.6 (1H, d, J=16 Hz), 6.95 (1H, s), 7.2 (1H, d, J=16 Hz), 7.6–8.7 (4H, m).

EXAMPLE 20

A solution of 7-[2-allyloxyimino-2-(5-amino-1,2,4-thiadiazol-3-yl)acetamido]-3-{2-[1-(3-aminopropyl)-3-pyridinio]thiovinyl}-3-cephem-4-carboxylate hydrochloride (syn isomer) (trans isomer) in pH 7.0 phosphate buffer (6.5 ml) was treated with 1N-NaOH to adjust pH 8.0 under ice-cooling. Ethyl formimidate hydrochloride (1.01 g) was added portionwise to the mixture and the pH of the mixture was maintained to be 7.7±0.5 by adding 1N-NaOH. After being stirred 40 minutes, the insoluble material was filtered off and the pH of the filtrate was adjusted to 4.6. The solution was subjected to column chromatography on Diaion Hp-20 using water and 20% (V/V) aqueous methanol as eluent. The fractions eluted with 20% aqueous methanol are lyophilized to give 7-[2-allyloxyimino-2-(5-amino-1,2,4-thiadiazol-3-yl)acetamido]-3-{2-[1-(3-formimidoylaminopropyl)-3-pyridinio]thiovinyl}-3-cephem-4-carboxylate (syn isomer) (trans isomer).

IR (Nujol): 3250, 1760, 1710, 1660, 1590, 1530 cm$^{-1}$

NMR (D₂O) δ: 2.13–2.68 (2H, m), 3.48 (2H, t, J=7 Hz), 3.73 (2H, m), 5.26 (1H, d, J=5 Hz), 5.79 (1H, d, J=5 Hz), 5.15–6.08 (3H, m), 6.62 (1H, d, J=14 Hz), 7.08 (1H, d, J=14 Hz), 7.83 (1H, s), 7.95 (1H, m), 8.43 (1H, d, J=8 Hz), 8.69 (1H, d, J=6 Hz), 8.79 (1H, s).

EXAMPLE 21

The following compounds were obtained according to similar manner to those of Example 1, Example 4, Example 6 and Example 8.

(1) 7-[2-Allyloxyimino-2-(5-amino-1,2,4-thiadiazol-3-yl)acetamido]-3-{2-[1-(2-hydroxyethyl)-3-pyridinio]thiovinyl}-3-cephem-4-carboxylate (syn isomer) (trans isomer).

mp: 160°–165° C. (dec.)

IR (Nujol): 1770, 1660, 1610, 1600, 1560, 1520 cm⁻¹

NMR (D₂O+DMSO-d₆) δ: 4.67 (4H, m), 5.08 (1H, d, J=5 Hz), 5.1–5.5 (2H, m), 5.70 (1H, d, J=5 Hz), 5.6–6.2 (1H, m), 5.6–6.2 (1H, d, J=15 Hz), 7.36 (1H, d, J=15 Hz), 7.99 (1H, m), 8.50 (1H, d, J=9 Hz), 8.75 (1H, d, J=7 Hz), 8.92 (1H, s).

(2) 7-[2-Allyloxyimino-2-(5-amino-1,2,4-thiadiazol-3-yl)acetamido]-3-{2-[1-(2-morpholinoethyl)-3-pyridinio]thiovinyl}-3-cephem-4-carboxylate dihydrochloride (syn isomer) (trans isomer).

mp: 75°–80° C. (dec.)

IR (Nujol): 3300, 3200, 2650, 2550, 2450, 2350, 1770, 1710, 1670, 1630, 1560, 1550, 1525, 1490 cm⁻¹

NMR (D₂O) δ: 3.30–3.67 (4H, m), 3.67–4.20 (8H, m), 4.50–4.90 (4H, m), 5.0–5.53 (3H, m), 5.83 (1H, d, J=5 Hz), 5.90–6.40 (1H, m), 6.90 (1H, d, J=16 Hz), 7.20 (1H, d, J=16 Hz), 7.90–8.20 (1H, m), 8.40–9.0 (3H, m).

(3) 7-[2-Allyloxyimino-2-(5-amino-1,2,4-thiadiazol-3-yl)acetamido]-3-{2-[1-(2,3-dihydroxypropyl)-3-pyridinio]thiovinyl}-3-cephem-4-carboxylate (syn isomer) (trans isomer).

mp: 195°–200° C. (dec.)

IR (Nujol): 1760, 1665, 1600, 1560, 1520 cm⁻¹

NMR (DMSO-d₆) δ: 3.2–4.3 (7H, m), 4.69 (4H, m), 5.10 (1H, d, J=5 Hz), 5.1–5.6 (2H, m), 5.78 (1H, dd, J=5 Hz, 8 Hz), 5.7–6.2 (1H, m), 6.56 (1H, d, J=15 Hz), 7.35 (1H, d, J=15 Hz), 8.16 (3H, m), 8.57 (1H, m), 8.84 (1H, m), 9.07 (1H, br. s), 9.55 (1H, d, J=8 Hz).

(4) 7-[2-Allyloxyimino-2-(5-amino-1,2,4-thiadiazol-3-yl)acetamido]-3-{2-[1-(4-methylpiperazin-1-ylcarbonylmethyl)-3-pyridinio]thiovinyl}-3-cephem-4-carboxylate (syn isomer) (trans isomer).

IR (Nujol): 3250–3400 (broad), 1760, 1660, 1600, 1510 cm⁻¹

NMR (DMSO-d₆) δ: 2.28–2.84 (8H, m), 3.56 (2H, m), 4.16–4.56 (3H, m), 4.68 (2H, s), 5.08–5.48 (3H, m), 5.52–6.0 (4H, m), 6.84 (1H, d, J=16 Hz), 7.36 (1H, d, J=16 Hz), 7.88–8.16 (4H, m), 8.56 (1H, d, J=8 Hz).

(5) 7-[2-Ethoxyimino-2-(5-amino-1,2,4-thiadiazol-3-yl)acetamido]-3-[2-(1-methyl-3-pyridinio)thiovinyl]-3-cephem-4-carboxylate (syn isomer) (cis isomer).

mp: 152°–157° C. (dec.)

IR (Nujol): 3300, 1760, 1670, 1600, 1520 cm⁻¹

NMR (DMSO-d₆) δ: 1.26 (3H, t, J=7 Hz), 3.78 (2H, br. s), 4.17 (2H, q, J=7 Hz), 4.32 (3H, s), 5.20 (1H, d, J=5 Hz), 5.83 (1H, 2d, J=8 Hz, J=5 Hz), 6.67 (1H, d, J=10 Hz), 6.95 (1H, d, J=10 Hz), 8.08 (2H, br. s, NH₂), 8.0 (1H, m), 8.50 (1H, d), 8.77 (1H, d), 9.00 (1H, s), 9.50 (1H, d, J=8 Hz).

(6) 7-[2-Allyloxyimino-2-(2-aminothiazol-4-yl)acetamido]-3-{2-[1-(3-aminopropyl)-3-pyridinio]thiovinyl}-3-cephem-4-carboxylate hydrochloride (syn isomer) (trans isomer).

IR (Nujol): 3350, 1770, 1665, 1618 cm⁻¹

NMR (D₂O) δ: 2.50 (2H, m), 3.15 (2H, m), 3.78 (2H, br. s), 4.8 (2H, m), 5.17 (1H, d, J=5 Hz), 5.45 (2H, m), 5.83 (1H, d, J=5 Hz), 6.0 (1H, m), 6.70 and 7.06 (2H, ABq, J=16 Hz), 7.14 (1H, s), 8.0 (1H, dd, J=6 Hz, 8 Hz), 8.53 (1H, d, J=8 Hz), 8.75 (1H, d, J=6 Hz), 8.90 (1H, br. s).

(7) 7-[2-Allyloxyimino-2-(5-amino-1,2,4-thiadiazol-3-yl)acetamido]-3-[2-{1-[3-(4-methylpiperazin-1-yl)propyl]-3-pyridinio}thiovinyl]-3-cephem-4-carboxylate.

mp: 168°–170° C.

IR (Nujol): 3300, 1760, 1660, 1610 cm⁻¹

NMR (DMSO-d₆) δ: 2–3 (2H, m), 3.1 (3H, s), 3.3–4.2 (12H, m), 4.5–4.7 (4H, m), 5.1–6.2 (5H, m), 6.73 (1H, d, J=16 Hz), 7.37 (1H, d, J=16 Hz), 8.0–8.3 (2H, m), 8.4–8.8 (1H, m), 8.8–9.3 (2H, m).

(8) 7-[3-Hydroxy-2-(2-aminothiazol-4-yl)propionamido]-3-[2-(1-methyl-3-pyridinio)thiovinyl]-3-cephem-4-carboxylate (trans isomer).

IR(Nujol): 3300, 3200, 1780, 1660, 1600, 1520 cm⁻¹

NMR (DMSO-d₆) δ: 3.20–4.05 (5H, m), 4.30 (3H, s), 5.03 (1H, d, J=5 Hz), 5.60 (1H, dd, J=5 Hz, 8 Hz), 6.33 (1H, br. s), 6.53 (1H, d, J=16 Hz), 6.93 (2H, br. s), 7.50 (1H, d, J=16 Hz), 7.90–8.90 (3H, m), 9.06 (1H, br. s).

(9) 7-[2-Allyloxyimino-2-(2-aminothiazol-4-yl)acetamido]-3-{2-[1-(3-N,N-dimethylaminopropyl)-3-pyridinio]thiovinyl}-3-cephem-4-carboxylate hydrochloride (syn isomer) (cis isomer).

IR (Nujol): 3300, 1775, 1660, 1610 cm⁻¹

NMR (D₂O) δ: 2.50 (2H, m), 2.90 (6H, s), 3.30 (2H, m), 3.73 (2H, br. s), 4.80 (2H, m), 4.82 (2H, m), 5.22 (1H, d, J=5 Hz), 5.43 (2H, m), 5.76 (1H, d, J=5 Hz), 5.90 (1H, m), 6.55 and 5.92 (2H, ABq, J=10 Hz), 7.07 (1H, s), 7.93 (1H, dd, J=6 Hz, 8 Hz), 8.40 (1H, d, J=8 Hz), 8.70 (1H, d, J=6 Hz), 8.82 (1H, br. s).

(10) 7-[2-Methoxyimino-2-(6-amino-2-pyridyl)acetamido]-3-[2-(1-methyl-3-pyridinio)thiovinyl]-3-cephem-4-carboxylate (syn isomer) (trans isomer).

mp: 165°–170° C. (dec.)

IR (Nujol): 3300, 3170, 1760, 1660, 1600, 1560, 1540, 1490 cm⁻¹

NMR (D₂O+DCl) δ: 3.88 (2H, br. s), 4.22 (3H, s), 4.46 (3H, s), 5.22 (1H, d, J=5 Hz), 5.82 (1H, d, J=5 Hz), 6.90 (1H, d, J=8 Hz), 7.12 (1H, d, J=16 Hz), 7.16 (1H, d, J=8 Hz), 7.32 (1H, d, J=16 Hz), 7.96 (1H, tri, J=8 Hz), 7.80–8.16 (1H, m), 8.40–8.64 (1H, m), 8.64–8.84 (1H, m), 8.92 (1H, s).

(11) 7-[2-(1-Carboxy-1-methylpropoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1595 cm⁻¹

NMR (DMSO-d₆/D₂O) δ: 0.67–1.17 (3H, m), 1.33–1.63 (2H, m), 3.47–4.23 (5H, m), 4.37 (3H, s), 5.13 (1H, d, J=5 Hz), 5.75 (1H, dd, J=8 Hz, 5 Hz), 6.53 (1H, d, J=16 Hz), 6.77 (1H, s), 7.30 (1H, d, J=16 Hz), 7.70–9.23 (4H, m).

(12) 7-[2-Allyloxyimino-2-(4-amino-2-pyrimidinyl)acetamido]-3-[2-(1-methyl-3-pyridinio)thiovinyl]-3-cephem-4-carboxylate (syn isomer) (trans isomer).

mp: 160°–165° C. (dec.)

NMR (DMSO-d₆) δ: 3.72 and 3.88 (2H, ABq, J=18 Hz), 4.38 (3H, s), 4.50–4.86 (2H, m), 5.10 (1H, d, 5 Hz), 5.20–5.52 (2H, m), 5.74 (1H, dd, J=5 Hz, 8 Hz), 5.72–6.16 (1H, m), 6.50 (1H, d, J=6 Hz), 6.60 (1H, d, J=16 Hz), 7.12 (2H, br. s), 7.50 (1H, d, J=16 Hz), 7.84–8.20 (1H, m), 8.14 (1H, d, J=6 Hz), 8.32–8.60 (1H, m).

(13) 7-[2-Methoxyimino-2-(6-formamido-2-pyridyl)acetamido]-3-[2-(1-methyl-3-pyridinio)thiovinyl]-3-cephem-4-carboxylate (syn isomer) (trans isomer).

mp: 145°–150° C. (dec.)

IR (Nujol): 3500, 3350, 3230, 3030, 1770, 1690, 1670, 1662, 1622, 1602, 1575, 1560, 1490 cm$^{-1}$ NMR (DMSO-$d_6$) δ: 3.50–3.83 (2H), 3.98 (3H, s), 4.35 (3H, s), 5.10 (1H, d, J=5 Hz), 5.72 (1H, dd, J=5 Hz, 8 Hz), 6.52 (1H, d, J=16 Hz), 6.97 (1H, d, J=8 Hz), 7.43 (1H, d, J=16 Hz), 7.50 (1H, d, J=8 Hz), 7.83 (1H, d, J=8 Hz), 7.93–8.17 (1H, m), 8.33–8.63 (1H, m), 8.70–8.90 (1H, m), 9.10 (1H, br. s), 9.50 (1H, d, J=8 Hz), 10.57–10.90 (1H).

(14) 7-[2-(1-tert-Butoxycarbonyl-1-cyclopentyloxyimino)-2-(2-tritylaminothiazol-4-yl)acetamido]-3-[2-(1-methyl-3-pyridinio)thiovinyl]-3-cephem-4-carboxylate (syn isomer) (trans isomer)

IR (Nujol): 1780, 1720, 1680, 1600 cm$^{-1}$.

(15) 7-[2-Allyloxyimino-2-(5-amino-1,2,4-oxadiazol-3-yl)acetamido]-3-[2-(1-methyl-3-pyridinio)thiovinyl]-3-cephem-4-carboxylate (syn isomer) (trans isomer).

IR (Nujol): 3200–3300, 1760, 1660, 1600 cm$^{-1}$

NMR (DMSO-$d_6$) δ: 3.97 (2H, s), 4.37 (3H, s), 4.72 (2H, d, J=5 Hz), 5.0–5.93 (5H, m), 6.57 (1H, d, J=16 Hz), 7.47 (1H, d, J=16 Hz), 7.77–8.13 (4H, m), 9.70 (1H, d, J=8 Hz).

(16) 7-[2-(2-Aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600 cm$^{-1}$

NMR ($D_2O$) δ: 3.65 (2H, d), 4.37 (3H, s), 5.17 (1H, d, J=5 Hz), 5.67 (1H, d, J=3 Hz), 6.50 (2H, s), 6.60 (1H, d, J=16 Hz), 7.13 (1H, d, J=16 Hz), 7.77–8.07 (1H, m), 8.30–8.77 (3H, m).

(17) 7-[2-Methoxyimino-2-(5-amino-1,2,4-oxadiazol-3-yl)acetamido]-3-[2-(1-methyl-3-pyridinio)thiovinyl]-3-cephem-4-carboxylate (syn isomer) (trans isomer).

IR (Nujol): 3300, 1760, 1660, 1600 cm$^{-1}$

NMR (DMSO-$d_6$/$D_2O$) δ: 3.53 (2H, s), 3.97 (3H, s), 4.37 (3H, s), 5.07 (1H, d, J=5 Hz), 5.67 (1H, dd, J=8 Hz, 5 Hz), 6.53 (1H, d, J=16 Hz), 7.47 (1H, d, J=16 Hz), 7.83–8.23 (1H, m), 8.33–9.10 (3H, m), 9.67 (1H, d, J=8 Hz).

(18) 7-[2-Ethoxyimino-2-(5-amino-1,2,4-thiadiazol-3-yl)acetamido]-3-[2-(1-methyl-3-pyridinio)thiovinyl]-3-cephem-4-carboxylate (syn isomer) (cis-trans isomer).

mp: 150°–155° C. (dec.)

IR (Nujol): 3300, 1750, 1670, 1600, 1520 cm$^{-1}$.

(19) 7-[2-Ethoxyimino-2-(5-amino-1,2,4-thiadiazol-3-yl)acetamido]-3-{2-[1-(3-N,N-dimethylaminopropyl)-3-pyridinio]thiovinyl}-3-cephem-4-carboxylate hydrochloride (syn isomer) (cis isomer).

IR (Nujol): 1770, 1665, 1620, 1520 cm$^{-1}$.

(20) 7-[2-Allyloxyimino-2-(2-aminothiazol-4-yl)acetamido]-3-{2-[1-(3-aminopropyl)-3-pyridinio]thiovinyl}-3-cephem-4-carboxylate hydrochloride (syn isomer) (cis isomer).

IR (Nujol): 3300, 1768, 1663, 1619 cm$^{-1}$.

(21) 7-[2-Methoxyimino-2-(2-aminothiazol-4-yl)acetamido]-3-{2-[1-(3-aminopropyl)-3-pyridinio]thiovinyl}-3-cephem-4-carboxylate hydrochloride (syn isomer) (cis isomer).

(22) 7-[2-Ethoxyimino-2-(5-amino-1,2,4-thiadiazol-3-yl)acetamido]-3-{2-[1-(2-aminoethyl)-3-pyridinio]thiovinyl}-3-cephem-4-carboxylate hydrochloride (syn isomer) (cis isomer).

mp: 115°–124° C. (dec.)

IR (Nujol): 1770, 1670, 1620, 1520 cm$^{-1}$.

(23) 7-[2-Ethoxyimino-2-(5-amino-1,2,4-thiadiazol-3-yl)acetamido]-3-{2-[1-(2-aminoethyl)-3-pyridinio]thiovinyl}-3-cephem-4-carboxylate hydrochloride (syn isomer) (trans isomer).

mp: 113°–122° C. (dec.)

IR (Nujol): 3320, 1765, 1660, 1620, 1520 cm$^{-1}$.

(24) 7-[2-Ethoxyimino-2-(5-amino-1,2,4-thiadiazol-3-yl)acetamido]-3-{2-[1-(2-N,N-dimethylaminoethyl)-3-pyridinio]-thiovinyl}-3-cephem-4-carboxylate hydrochloride (syn isomer) (cis isomer).

IR (Nujol): 3300, 1760, 1670, 1610, 1520 cm$^{-1}$.

(25) 7-[2-Methoxyimino-2-(2-aminothiazol-4-yl)acetamido]-3-{2-[1-(3-N,N-dimethylaminopropyl)-3-pyridinio]thiovinyl}-3-cephem-4-carboxylate hydrochloride (syn isomer) (trans isomer).

(26) 7-[2-Methoxyimino-2-(2-aminothiazol-4-yl)acetamido]-3-{2-[1-(2-aminoethyl)-3-pyridinio]thiovinyl}-3-cephem-4-carboxylate hydrochloride (syn isomer) (trans isomer).

(27) 7-[2-Methoxyimino-2-(2-aminothiazol-4-yl)acetamido]-3-{2-[1-(3-N,N-dimethylaminopropyl)-3-pyridinio]thiovinyl}-3-cephem-4-carboxylate hydrochloride (syn isomer) (cis isomer).

(28) 7-[2-Methoxyimino-2-(2-aminothiazol-4-yl)acetamido]-3-{2-[1-(3-aminopropyl)-3-pyridinio]thiovinyl}-3-cephem-4-carboxylate hydrochloride (syn isomer) (trans isomer).

IR (Nujol): 1770, 1670, 1620, 1560 cm$^{-1}$.

(29) 7-[2-Allyloxyimino-2-(2-aminothiazol-4-yl)acetamido]-3-{2-[1-(2-aminoethyl)-3-pyridinio]thiovinyl}-3-cephem-4-carboxylate hydrochloride (syn isomer) (cis isomer).

IR (Nujol): 3350, 1770, 1660, 1620 cm$^{-1}$.

(30) 7-[2-Allyloxyimino-2-(2-aminothiazol-4-yl)acetamido]-3-{2-[1-(3-N,N-dimethylaminopropyl)-3-pyridinio]thiovinyl}-3-cephem-4-carboxylate hydrochloride (syn isomer) (trans isomer).

IR (Nujol): 3350, 1770, 1660, 1613 cm$^{-1}$.

(31) 7-[2-Allyloxyimino-2-(2-aminothiazol-4-yl)acetamido]-3-{2-[1-(2-aminoethyl)-3-pyridinio]thiovinyl}-3-cephem-4-carboxylate hydrochloride (syn isomer) (trans isomer).

IR (Nujol): 3350, 1768, 1660, 1627 cm$^{-1}$.

(32) 7-[2-Methoxyimino-2-(5-amino-1,2,4-thiadiazol-3-yl)acetamido]-3-{2-[1-(3-aminopropyl)-3-pyridinio]-thiovinyl}-3-cephem-4-carboxylate hydrochloride (syn isomer) (trans isomer).

mp: 185°–190° C. (dec.)

IR (Nujol): 3350, 3150, 1765, 1670, 1615, 1595, 1560, 1525, 1490 cm$^{-1}$.

(33) 7-[2-Carboxymethoxyimino-2-(2-aminothiazol-4-yl)acetamido]-3-{2-[1-(3-aminopropyl)-3-pyridinio]thiovinyl}-3-cephem-4-carboxylate hydrochloride (syn isomer) (cis isomer).

IR (Nujol): 3350, 1780, 1710, 1673, 1627 cm$^{-1}$.

(34) 7-[2-Allyloxyimino-2-(5-amino-1,2,4-thiadiazol-3-yl)acetamido]-3-{2-[1-(3-aminopropyl)-3-pyridinio]thiovinyl}-3-cephem-4-carboxylate dihydrochloride (syn isomer) (trans isomer).

mp: 164°–168° C. (dec.)

IR (Nujol): 3400–3100, 1770, 1710, 1670, 1620, 1530 cm$^{-1}$.

(35) 7-[2-Allyloxyimino-2-(5-amino-1,2,4-thiadiazol-3-yl)acetamido]-3-{2-[1-(3-N,N-dimethylaminopropyl)-3-pyridinio]thiovinyl}-3-cephem-4-carboxylate hydrochloride (syn isomer) (trans isomer).

mp: 70°–75° C. (dec.)

IR (Nujol): 3300, 2700, 1760, 1660, 1610, 1520 Cm$^{-1}$.

(36) 7-[2-Allyloxyimino-2-(5-amino-1,2,4-thiadiazol-3-yl)acetamido]-3-{2-[1-(2-aminoethyl)-3-pyridinio]thiovinyl}-3-cephem-4-carboxylate dihydrochloride (syn isomer) (cis isomer).

mp: 125°–130° C. (dec.)

IR (Nujol): 1765, 1670, 1605, 1510 cm$^{-1}$.

(37) 7-[2-Allyloxyimino-2-(5-amino-1,2,4-thiadiazol-3-yl)acetamido]-3-{2-[1-(3-N,N-dimethylaminopropyl)-3-pyridinio]thiovinyl}-3-cephem-4-carboxylate hydrochloride (syn isomer) (cis isomer).

mp: 65°–70° C. (dec.)

IR (Nujol): 3350, 2700, 1765, 1670, 1600, 1525 cm$^{-1}$.

(38) 7-[2-Allyloxyimino-2-(5-amino-1,2,4-thiadiazol-3-yl)acetamido]-3-{2-[1-(3-aminopropyl)-3-pyridinio]thiovinyl}-3-cephem-4-carboxylate hydrochloride (syn isomer) (cis isomer).

mp: 65°–70° C. (dec.)

IR (Nujol): 3350, 3150, 1770, 1710, 1670, 1620, 1525 cm$^{-1}$.

(39) 7-[2-Allyloxyimino-2-(5-amino-1,2,4-thiadiazol-3-yl)acetamido]-3-{2-[1-(2-aminoethyl)-3-pyridinio]thiovinyl}-3-cephem-4-carboxylate dihydrochloride (syn isomer) (trans isomer).

mp: 170°–175° C. (dec.)

IR (Nujol): 1760, 1670, 1620 cm$^{-1}$.

(40) 7-[2-Ethoxyimino-2-(5-amino-1,2,4-thiadiazol-3-yl)acetamido]-3-{2-[1-(3-aminopropyl)-3-pyridinio]thiovinyl}-3-cephem-4-carboxylate hydrochloride (syn isomer) (cis isomer).

mp: 116°–126° C. (dec.)

IR (Nujol): 1770, 1670, 1610, 1510 cm$^{-1}$. (41) 7-[2-Ethoxyimino-2-(5-amino-1,2,4-thiadiazol-3-yl)acetamido]-3-{2-[1-(3-aminopropyl)-3-pyridinio]thiovinyl}-3-cephem-4-carboxylate hydrochloride (syn isomer) (trans isomer).

mp: 148°–157° C. (dec.)

IR (Nujol): 1770, 1670, 1620, 1530 cm$^{-1}$.

(42) 7-[2-Ethoxyimino-2-(5-amino-1,2,4-thiadiazol-3-yl)acetamido]-3-{2-[1-(3-N,N-dimethylaminopropyl)-3-pyridinio]thiovinyl}-3-cephem-4-carboxylate hydrochloride (syn isomer) (trans isomer).

mp: 121°–130° C. (dec.)

IR (Nujol): 3350, 2700, 1770, 1670, 1620, 1530 cm$^{-1}$.

(43) 7-[2-(1-Carboxy-1-cyclopentyloxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1650, 1590 cm$^{-1}$.

EXAMPLE 22

The following compounds were obtained according to a similar manner to those of Examples 14 and 15.

(1) 7-[2-Ethoxyimino-2-(5-amino-1,2,4-thiadiazol-3-yl)acetamido]-3-[2-(1-methyl-3-pyridinio)thiovinyl]-3-cephem-4-carboxylate (syn isomer) (trans isomer).

IR (Nujol): 3300 (broad), 1760, 1660, 1600, 1520 cm$^{-1}$.

(2) 7-[2-Ethoxyimino-2-(5-amino-1,2,4-thiadiazol-3-yl)acetamido]-3-[2-(1-methyl-2-pyridinio)thiovinyl]-3-cephem-4-carboxylate hydriodide (syn isomer) (trans isomer).

IR (Nujol): 3400, 3250, 1780, 1650–1680, 1620 cm$^{-1}$.

(3) 7-[2-Ethoxyimino-2-(5-amino-1,2,4-thiadiazol-3-yl)acetamido]-3-[2-(1-methyl-2-pyridinio)thiovinyl]-3-cephem-4-carboxylate (syn isomer) (trans isomer).

IR (Nujol): 3300, 3200, 1760, 1650, 1600 cm$^{-1}$.

(4) 7-[2-Methoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3400–3100 (broad), 1760, 1660, 1600, 1520 cm$^{-1}$

NMR (D$_2$O-DCl) δ: 3.90 (2H, d), 4.12 (3H, s), 4.50 (3H, s), 5.32 (1H, d, J=4 Hz), 5.80 (1H, d, J=4 Hz), 7.05 and 7.40 (2H, 2xd, J=16 Hz), 7.18 (1H, s), 7.8–9.0 (4H, m).

(5) Trifluoroacetic acid salt of 7-amino-3-[2-(1-methyl-2-pyridinio)thiovinyl]-3-cephem-4-carboxylate hydriodide (trans isomer)

IR (Nujol): 2550–2450, 1760, 1660, 1640, 1600 cm$^{-1}$

NMR (DMSO-d$_6$) δ: 3.75–4.3 (2H, m), 4.21 (3H, s), 5.0–5.47 (2H, m), 7.13 (1H, d, J=16 Hz), 7.3–8.3 (6H, m), 9.0 (1H, d, J=5 Hz).

(6) Trifluoroacetic acid salt of 7-amino-3-[2-(1-methyl-3-pyridinio)thiovinyl]-3-cephem-4-carboxylate hydriodide (trans isomer).

IR (Nujol): 3350, 2500–2600, 1780, 1670, 1620 cm$^{-1}$

NMR (DMSO-d$_6$) δ: 3.95 (2H, ABq, J=18 Hz), 4.30 (3H, s), 5.1–5.3 (2H, m), 6.5–7.3 (2H, m), 8.0–8.9 (5H, m), 9.13 (1H, broad s).

(7) Trifluoroacetic acid salt of 7-amino-3-[2-(4-methyl-2-pyrazinio)thiovinyl]-3-cephem-4-carboxylate hydriodide (trans isomer).

IR (Nujol): 3300, 1800, 1670 cm$^{-1}$.

(8) 7-[2-Methoxyimino-2-(2-aminothiazol-4-yl)acetamido]-3-[2-(1-methyl-2-pyridinio)thiovinyl]-3-cephem-4-carboxylate (syn isomer) (trans isomer).

IR (Nujol): 3300, 1765, 1670, 1611, 1562, 1533 cm$^{-1}$.

(9) 7-[2-Methoxyimino-2-(2-aminothiazol-4-yl)acetamido]-3-[2-(4-methyl-2-pyrazinio)thiovinyl]-3-cephem-4-carboxylate (syn isomer) (trans isomer).

IR (Nujol): 3300, 1765 (br.), 1660, 1600 cm$^{-1}$.

(10) 7-[2-Methoxyimino-2-(2-tritylaminothiazol-4-yl)acetamido]-3-[2-(1-methyl-2-pyridinio)thiovinyl]-3-cephem-4-carboxylate. (syn isomer) (trans isomer).

IR (Nujol): 3250, 1780, 1672, 1595 cm$^{-1}$.

(11) 7-[2-Methoxyimino-2-(2-tert-pentyloxycarbonylaminothiazol-4-yl)acetamido]-3-[2-(4-methyl-2-pyrazinio)thiovinyl]-3-cephem-4-carboxylate (syn isomer) (trans isomer).

IR (Nujol): 3350, 1762, 1700, 1660, 1530 cm$^{-1}$.

(12) 7-[2-Ethoxyimino-2-(5-amino-1,2,4-thiadiazol-3-yl)acetamido]-3-[2-(1,3-dimethyl-2-pyrimidinio)thiovinyl]-3-cephem-4-carboxylate iodide (syn isomer) (trans isomer)

IR (Nujol): 3350, 1770, 1663, 1605 cm$^{-1}$

NMR (D$_2$O) δ: 1.40 (3H, t, J=7 Hz), 3.80 (2H, br. s), 3.91 (3H, s), 4.14 (3H, s), 4.50 (2H, q, J=7 Hz), 5.30 (1H, d, J=5 Hz), 5.80 (1H, d, J=5 Hz), 6.73, 7.27 (2H, ABq, J=16 Hz), 7.77 (1H, m), 9.03 (2H, m).

(13) 7-[2-Ethoxyimino-2-(5-amino-1,2,4-thiadiazol-3-yl)acetamido]-3-[2-(4-methyl-2-pyrazinio)thiovinyl]-3-cephem-4-carboxylate (syn isomer) (trans isomer).

IR (Nujol): 3350, 1760 (br.), 1665, 1607 cm$^{-1}$

NMR (DMSO-d$_6$) δ: 1.20 (3H, t, J=7 Hz), 3.90 (2H, br.s), 4.13 (2H, q, J=7 Hz), 4.26 (3H, s), 5.17 (1H, d, J=5 Hz), 5.77 (1H, dd, J=5 Hz, 8 Hz), 7.22 (2H, br.s), 8.03 (2H, br. s), 8.80 (1H, br.s), 9.20 (2H, br.s), 9.50 (1H, d, J=8 Hz).

(14) 7-[2-Methoxyimino-2-(5-amino-1,2,4-thiadiazol-3-yl)acetamido]-3-[2-(1-methyl-2-pyridinio)thiovinyl]-3-cephem-4-carboxylate (syn isomer) (trans isomer).

IR (Nujol): 3250–3350, 1770, 1660, 1620, 1560, 1530 cm$^{-1}$.

(15) Trifluoroacetic acid salt of 7-amino-3-[2-(1-methyl-3-pyridinio)thiovinyl]-3-cephem-4-carboxylate hydriodide (cis isomer).

IR (Nujol): 3400 (broad), 2350 (broad), 1800, 1670, 1620, 1540–1520 cm$^{-1}$.

(16) 7-[2-Ethoxyimino-2-(5-amino-1,2,4-thiadiazol-3-yl)acetamido]-3-[2-(1-ethyl-3-pyridinio)thiovinyl]-3-cephem-4-carboxylate (syn isomer) (trans isomer).

IR (Nujol): 3300 (broad), 1770, 1675, 1600, 1520 cm$^{-1}$

NMR (DMSO-d$_6$) δ: 1.05–1.80 (4H, m, J=7 Hz), 3.13–3.8 (2H, m), 4.23 (3H, q, J=7 Hz), 4.68 (3H, q, J=7 Hz), 5.12 (1H, d, J=5 Hz), 5.68 (1H, d-d, J=5, 8 Hz), 6.64 (1H, d, J=16 Hz), 7.49 (1H, d, J=16 Hz), 7.80–9.30 (6H, m), 9.50 (1H, d, J=8 Hz).

(17) 7-[2-Ethoxyimino-2-(5-amino-1,2,4-thiadiazol-3-yl)acetamido]-3-[2-(1-methyl-3-pyridinio)thiovinyl]-3-cephem-4-carboxylate (syn isomer) (cis isomer).

IR (Nujol): 3300 (broad), 1760, 1665, 1600, 1520 cm$^{-1}$.

(18) 7-[2-Carboxymethoxyimino-2-(5-amino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3300 (broad), 1765, 1670, 1615, 1560, 1525 cm$^{-1}$.

(19) 7-[2-Allyloxyimino-2-(5-amino-1,2,4-thiadiazol-3-yl)acetamido]-3-[2-(1-methyl-3-pyridinio)thiovinyl]-3-cephem-4-carboxylate (syn isomer) (trans isomer).

IR (Nujol): 3300, 1760, 1670, 1620, 1600, 1530 cm$^{-1}$.

(20) 7-[2-(Tert-butoxycarbonylmethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3200–3300, 2400–2600, 1770, 1715, 1680, 1630 cm$^{-1}$

NMR (DMSO-d$_6$) δ: 1.50 (9H, s), 3.20–4.10 (2H, m), 4.43 (3H, s), 4.70 (2H, s), 5.30 (1H, d, J=5 Hz), 5.83 (1H, dd, J=5 Hz, 8 Hz), 7.00 (1H, s), 7.30 (2H, broad s), 8–9.00 (6H, m), 9.27 (1H, broad s), 9.77 (1H, d, J=8 Hz).

(21) 7-[2-Carboxymethoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1765, 1670, 1620 cm$^{-1}$

NMR (DMSO-d$_6$) δ: 3.50–4.10 (2H, m), 4.30 (3H, s), 4.63 (2H, broad s), 5.23 (1H, d, J=5 Hz), 5.90 (1H, dd, J=5 Hz, 8 Hz), 6.87 (1H, s), 6.95 (1H, d, J=15 Hz), 7.15 (2H, broad s), 7.47 (1H, d, J=15 Hz), 7.90–8.90 (3H, m), 9.13 (1H, broad s), 9.80 (1H, d, J=8 Hz).

(22) 7-[2-(3-Carboxy-2-propenyloxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535 cm$^{1}$

NMR (DMSO-d$_6$/D$_2$O) δ: 3.57–4.20 (2H, m), 4.37 (3H, s), 4.57–4.93 (2H, m), 5.10 (1H, d, J=5 Hz), 5.60 (1H, dd, J=5 Hz, 8 Hz), 5.98 (1H, d, J=16 Hz), 6.51 (1H, d, J=16 Hz), 7.48 (1H, d, J=16 Hz), 6.78 (1H, s), 7.76–9.17 (4H, m), 9.67 (1H, d, J=8 Hz).

(23) 7-[2-(1-Methyl-2-pyridiniomethoxyimino)-2-(2-aminothiazol-4-yl)acetamido]-3-[2-(1-methyl-3-pyridinio)thiovinyl]-3-cephem-4-carboxylate iodide (syn isomer) (trans isomer).

IR (Nujol): 3250, 1760, 1665, 1615 cm$^{-1}$

NMR (D$_2$O) δ: 7.9–9.00 (8H, m), 7.17 (1H, d, J=16 Hz), 7.10 (1H, s), 6.67 (1H, d, J=16 Hz), 5.90 (1H, d, J=5 Hz), 5.75 (2H, s), 5.34 (1H, d, J=5 Hz), 4.45 (6H, s), 3.5–4.25 (2H, m).

(24) 7-[2-(2-Pyridylmethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1620, 1590 cm$^{-1}$

NMR (DMSO-d$_6$) δ: 3.7–4.20 (2H, m), 4.47 (3H, s), 5.15 (1H, d, J=5 Hz), 5.25 (2H, s), 5.72 (1H, dd, J=5 Hz, 8 Hz), 6.48 (1H, d, J=14 Hz), 6.80 (1H, s), 7.1–9.0 (11H, m), 9.90 (1H, d, J=8 Hz).

(25) 7-[2-(3-Carboxypropoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535 cm$^{-1}$

NMR (DMSO-d$_6$/D$_2$O) δ: 1.5–2.73 (4H, m), 3.3–4.27 (4H, m), 4.37 (3H, s), 5.08 (1H, d, J=5 Hz), 5.63 (1H, dd, J=5 Hz, 8 Hz), 6.50 (1H, d, J=16 Hz), 7.48 (1H, d, J=16 Hz), 6.74 (1H, s), 7.76–9.13 (4H, m), 9.55 (1H, d, J=8 Hz).

(26) 7-[2-(1-Carboxypropoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1590 cm$^{-1}$

NMR (DMSO-d$_6$) δ: 1.08 (3H, t, J=7 Hz), 1.62–2.24 (2H, m), 3.2–3.9 (2H, m), 4.42 (3H, s), 4.47 (1H, t, J=6 Hz), 5.15 (1H, d, J=5 Hz), 5.77 (1H, dd, J=8 Hz, 5 Hz), 6.47 (1H, d, J=16 Hz), 6.87 (1H, s), 7.0 (1H, d, J=16 Hz), 7.02–9.3 (4H, m).

(27) 7-[2-Allyloxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1530 cm$^{-1}$

NMR (DMSO-d$_6$/D$_2$O) δ: 3.33–3.87 (4H, m), 4.37 (3H, s), 4.62 (2H, d, J=5 Hz), 6.50 (1H, d, J=16 Hz), 7.47 (1H, d, J=16 Hz), 6.73 (1H, s), 7.83–9.03 (4H, m), 9.57 (1H, d, J=8 Hz).

(28) 7-[2-(2-Hydroxyethoxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1535, 1500 cm$^{-1}$

NMR (DMSO-d$_6$/D$_2$O) δ: 3.20–3.83 (2H, m), 4.35 (3H, s).

(29) 7-[2-Ethoxyimino-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3300, 1760, 1665, 1600, 1535 cm$^{-1}$

NMR (DMSO-d$_6$/D$_2$O) δ: 1.25 (3H, t, J=7 Hz), 4.13 (2H, ABq, J=7 Hz), 4.37 (3H, s), 5.08 (1H, d, J=5 Hz), 5.65 (1H, dd, J=5 Hz), 6.48 (1H, d, J=16 Hz), 7.48 (1H, d, J=16 Hz), 7.73–7.93 (4H, m), 9.52 (1H, d, J=8 Hz), 6.73 (1H, s).

(30) 7-[2-(2-Propynyloxyimino)-2-(2-aminothiazol-4-yl)acetamido]-3-[2-(1-methyl-3-pyridinio)thiovinyl]-3-cephem-4-carboxylate (syn isomer) (trans isomer).

IR (Nujol): 3250, 1760, 1660, 1600, 1530 cm$^{-1}$

NMR (DMSO-d$_6$/D$_2$O) δ: 3.3–3.8 (3H, m), 4.37 (3H, s), 4.7 (2H, s), 5.09 (1H, d, J=5 Hz), 5.63 (1H, dd, J=5 Hz, 8 Hz), 6.53 (1H, d, J=16 Hz), 6.78 (1H, s), 7.50 (1H, d, J=16 Hz), 7.73–7.93 (4H, m), 9.05 (1H, s), 9.52 (1H, d, J=8 Hz).

(31) 7-[2-(Tert-butoxycarbonylmethoxyimino)-2-(2-formamidothiazol-4-yl)acetamido]-3-[2-(1-methyl-3-pyridinio)thiovinyl]-3-cephem-4-carboxylate (syn isomer) (trans isomer).

IR (Nujol): 3200–3400, 1760, 1720–1730, 1690, 1670 cm$^{-1}$

NMR (DMSO-d$_6$) δ: 1.50 (9H, s), 3.50–4.20 (2H, m), 4.37 (3H, s), 4.63 (2H, s), 5.27 (1H, d, J=5 Hz), 5.87 (1H, dd, J=5 Hz, 8 Hz), 7.00 (1H, d, J=16 Hz), 7.40 (1H, d, J=16 Hz), 7.45 (1H, s), 7.95-9.10 (4H, m), 8.53 (1H, s), 9.67 (1H, d, J=8 Hz), 12.70 (1H, broad s).

(32) 7-{2-(1-Tert-butoxycarbonyl)propoxyimino]-2-(2-formamidothiazol-4-yl)acetamido]}-3-[2-(1-methyl-3-pyridinio)thiovinyl]-3-cephem-4-carboxylate (syn isomer) (trans isomer).

IR (Nujol): 3250, 1760, 1720, 1680 cm$^{-1}$

NMR (DMSO-d$_6$) δ: 0.98 (3H, t, J=7 Hz), 1.45 (9H, s), 1.52-2.06 (2H, m), 3.67-4.17 (2H, m), 4.37 (3H, s), 4.5 (1H, t, J=6 Hz), 5.28 (1H, d, J=5 Hz), 5.93 (1H, dd, J=8 Hz, 5 Hz), 6.43 (1H, d, J=16 Hz), 7.22 (1H, s), 7.63 (1H, d, J=16 Hz), 7.83-9.33 (4H, m), 8.52 (1H, s), 9.6 (1H, d, J=8 Hz).

(33) 7-[2-(2-Pyridylmethoxyimino)-2-(2-formamidothiazol-4-yl)acetamido]-3-[2-(1-methyl-3-pyridinio)thiovinyl]-3-cephem-4-carboxylate (syn isomer) (trans isomer).

NMR (DMSO-d$_6$) δ: 3.3-4.00 (2H, m), 4.33 (3H, s), 5.13 (1H, d, J=5 Hz), 5.30 (2H, broad s), 5.83 (1H, dd, J=5 Hz, 8 Hz), 6.50 (1H, d, J=15 Hz), 7.20-9.00 (9H, m), 7.43 (1H, s), 8.50 (1H, s), 9.95 (1H, d, J=8 Hz).

(34) 7-[2-(3-Benzhydryloxycarbonyl-2-propenyloxyimino)-2-(2-tritylaminothiazol-4-yl)acetamido]-3-[2-(1-methyl-3-pyridinio)thiovinyl]-3-cephem-4-carboxylate (syn isomer) (trans isomer).

IR (Nujol): 3300, 1780, 1720, 1680, 1600, 1530, 1500 cm$^{-1}$

NMR (DMSO-d$_6$/D$_2$O) δ: 3.7-4.35 (2H, m), 4.40 (3H, s), 4.67-5.00 (2H, m), 5.27 (1H, d, J=5 Hz), 5.83 (1H, m), 6.25 (1H, d, J=16 Hz), 6.67-7.00 (3H, m), 7.33 (26H, m), 8.00-9.20 (5H, m), 9.80 (1H, d, J=8 Hz).

(35) 7-[2-Ethoxyimino-2-(2-tritylaminothiazol-4-yl)acetamido]-3-[2-(1-methyl-3-pyridinio)thiovinyl]-3-cephem-4-carboxylate (syn isomer) (trans isomer).

NMR (DMSO-d$_6$/D$_2$O) δ: 1.20 (3H, t, J=7 Hz), 3.6-4.0 (2H, m), 4.06 (2H, ABq, J=7 Hz), 4.37 (3H, s), 5.15 (1H, d, J=5 Hz), 5.67 (1H, dd, J=5 Hz, 8 Hs), 6.72 (1H, s), 7.17-7.50 (15H, m), 8.43-9.17 (4H, m), 9.51 (1H, d, J=5 Hz).

(36) 7-[2-(2-Propynyloxyimino)-2-(2-tritylaminothiazol-4-yl)acetamido]-3-[2-(1-methyl-3-pyridinio)thiovinyl]-3-cephem-4-carboxylate (syn isomer) (trans isomer).

NMR (DMSO-d$_6$/D$_2$O) δ: 3.4-3.7 (3H, m), 4.37 (3H, s), 5.21 (1H, d, J=5 Hz), 5.73 (1H, dd, J=5 Hz, 8 Hz), 6.78 (1H, s), 7.13-7.50 (15H, m), 9.65 (1H, d, J=8 Hz).

(37) 7-[2-(3-Benzhydryloxycarbonylpropoxyimino)-2-(2-tritylaminothiazol-4-yl)acetamido]-3-[2-(1-methyl-3-pyridinio)thiovinyl]-3-cephem-4-carboxylate (syn isomer) (trans isomer).

IR (Nujol): 3350, 1770, 1720, 1665, 1590, 1520 cm$^{-1}$

NMR (DMSO-d$_6$/D$_2$) δ: 1.53-2.10 (4H, m), 3.50-3.70 (2H, m), 3.83-4.27 (2H, m), 4.35 (3H, s), 5.17 (1H, d, J=8 Hz), 5.63 (1H, m), 6.78 (1H, s), 6.87 (1H, d, J=15 Hz), 6.90 (1H, s), 7.10-7.50 (26H, m), 7.80-9.17 (4H, m), 9.60 (1H, d, J=8 Hz).

(38) 7-[2-Carboxymethoxyimino-2-(thiazol-4-yl)acetamido]-3-[2-(1-methyl-3-pyridinio)thiovinyl]-3-cephem-4-carboxylate (syn isomer) (trans isomer).

IR (Nujol): 3350, 1760, 1660, 1600 cm$^{-1}$

NMR (D$_2$O-NaHCO$_3$) δ: 3.73 (2H, s), 4.35 (3H, s), 4.50-4.87 (2H, m), 5.32 (1H, d, J=5 Hz), 5.83 (1H, dd, J=5 Hz, 8 Hz), 6.63 (1H, d, J=16 Hz), 7.17 (1H, d, J=16 Hz), 7.80-8.80 (6H, m).

(39) 7-[2-Hydroxy-2-(2-aminothiazol-4-yl)acetamido]-3-[2-(1-methyl-3-pyridinio)thiovinyl]-3-cephem-4-carboxylate (trans isomer).

IR (Nujol): 3300, 1760, 1670, 1600 cm$^{-1}$

NMR (DMSO-d$_6$) δ: 3.42-4.04 (2H, m), 4.43 (3H, s), 5.00 (1H, s), 5.15 (1H, d, J=5 Hz), 5.70 (1H, dd, J=8 Hz, 5 Hz), 6.54 (1H, s), 6.6 (1H, d, J=16 Hz), 7.02 (2H, broad s), 7.53 (1H, d, J=16 Hz), 7.73-9.17 (4H, m).

(40) 7-[2-(1-Carboxy)ethoxyimino-2-(5-amino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3300, 1770, 1665, 1600, 1520 cm$^{-1}$

NMR (DMSO-d$_6$/D$_2$O) δ: 1.51 (3H, d, J=6 Hz), 3.80 (2H, broad s), 4.31 (3H, s), 4.75 (1H, d, J=6 Hz), 5.25 (1H, d, J=4 Hz), 5.85 (1H, d, J=4 Hz), 6.83 (1H, d, J=16 Hz), 7.50 (1H, d, J=16 Hz), 7.6-9.4 (4H, m).

(41) 7-[2-(1-Methyl-1-carboxyethoxyimino)-2-(5-amino-1,2,4-thiadiazol-3-yl)acetamido]-3-[2-(1-methyl-3-pyridinio)thiovinyl]-3-cephem-4-carboxylate (syn isomer) (trans isomer).

IR (Nujol): 3300, 1770, 1670, 1610, 1520 cm$^{-1}$

NMR (D$_2$O-NaHCO$_3$) δ: 1.60 (6H, s), 3.82 (2H, s), 4.42 (3H, s), 5.35 (1H, d, J=4 Hz), 5.90 (1H, d, J=4 Hz), 6.70 (1H, d, J32 16 Hz), 7.20 (1H, d, J=16 Hz), 7.5-8.9 (3H, m).

(42) 7-[2-Ethoxyimino-2-(5-amino-1,2,4-thiadiazol-3-yl)acetamido]-3-[2-(1-carboxymethyl-3-pyridinio)thiovinyl]-3-cephem-4-carboxylate (syn isomer) (trans isomer).

IR (Nujol): 3300, 1760, 1640-1680, 1610, 1520 cm$^{-1}$

NMR (DMSO-d$_6$) δ: 1.30 (3H, t, J=5 Hz), 3.33-3.90 (2H, m), 4.25 (2H, q, J=7 Hz), 4.95-5.20 (3H, m), 5.75 (1H, m), 6.60 (1H, d, J=16 Hz), 7.50 (1H, d, J=16 Hz), 8.00-9.00 (4H, m), 9.55 (1H, d, J=8 Hz).

(43) 7-[2-Ethoxyimino-2-(5-amino-1,2,4-thiadiazol-3-yl)acetamido]-3-[2-(2-trimethylammonioethyl)thiovinyl]-3-cephem-4-carboxylate (syn isomer) (trans isomer).

IR (Nujol): 3300, 1760, 1670, 1600, 1520 cm$^{-1}$

NMR (DMSO-d$_6$) δ: 1.25 (3H, t, J=5 Hz), 3.10-4.00 (6H, m), 4.20 (2H, q, J=7 Hz), 5.05 (1H, d, J=5 Hz), 5.60 (1H, m), 6.60 (1H, d, J=16 Hz), 7.03 (1H, d, J=16 Hz), 8.06 (2H, broad s), 9.50 (1H, d, J=8 Hz).

(44) 7-[(4-Carboxy-3-hydroxyisothiazol-5-yl)thioacetamido]-3-[2-(1-methyl-3-pyridinio)thiovinyl]-3-cephem-4-carboxylate (trans isomer).

IR (Nujol): 3300, 1760, 1670 cm$^{-1}$

NMR (DMSO-d$_6$) δ: 3.93 (2H, s), 3.83-4.00 (2H, m), 4.47 (3H, s), 5.27 (1H, d, J=5 Hz), 5.70 (1H, dd, J=8 Hz), 7.30 (6H, m), 9.50 (1H, d, J=8 Hz).

(45) 7-[2-Methoxyimino-2-(5,6-dihydro-1,4-oxathiin-2-yl)acetamido]-3-[2-(1-methyl-3-pyridinio)thiovinyl]-3-cephem-4-carboxylate (syn isomer) (trans isomer).

IR (Nujol): 3300, 1760, 1660, 1600, 1500 cm$^{-1}$

NMR (D$_2$O) δ: 3.0-3.23 (2H, m), 3.73 (2H, s), 4.33 (3H, s), 5.22 (1H, d, J=5 Hz), 5.71 (1H, d, J=5 Hz), 5.97 (1H, s), 6.58 (1H, d, J=16 Hz), 7.12 (1H, d, J=16 Hz).

(46) 7-[2-Methoxyimino-2-(1,2,3-thiadiazol-4-yl)acetamido]-3-[2-(1-methyl-3-pyridinio)thiovinyl]-3-cephem-4-carboxylate (syn isomer) (trans isomer).

IR (Nujol): 3200-3350, 1760, 1660, 1600, 1555 cm$^{-1}$

NMR (DMSO-d$_6$/D$_2$O) δ: 3.67 (2H, s), 4.02 (3H, s), 4.37 (3H, s), 5.13 (1H, d, J=5 Hz), 5.80 (1H, dd, J=5 Hz, 8 Hz), 6.50 (1H, d, J=16 Hz), 7.50 (1H, d, J=16 Hz), 7.83-9.10 (4H, m), 9.40 (1H, s), 9.78 (1H, d, J=8 Hz).

(47) 7-[2-Methoxyimino-2-(3-hydroxyphenyl)acetamido]-3-[2-(1-methyl-3-pyridinio)thiovinyl]-3-cephem-4-carboxylate (syn isomer) (trans isomer).

IR (Nujol): 1770, 1650, 1600, 1570, 1500 cm$^{-1}$

NMR (DMSO-d$_6$/D$_2$O) δ: 3.50-4.17 (5H, m), 4.17-4.67 (3H, m), 5.17 (1H, d, J=5 Hz), 5.77 (1H, dd,

J=5 Hz, 8 Hz), 6.60 (1H, d, J=16 Hz), 7.53 (1H, d, J=16 Hz), 6.83–7.40 (4H, m), 7.73–8.93 (4H, m).

(48) Trifluoroacetic acid salt of 7-amino-3-[2-(1-methyl-2-pyridinio)thiovinyl]-3-cephem-4-carboxylic acid iodide (cis isomer).

IR (Nujol): 2300–2500, 1780, 1670, 1610, 1560 cm$^{-1}$

NMR (DMSO-d$_6$) δ: 3.85 (2H, ABq, J=17 Hz), 4.20 (3H, s), 5.35 (2H, m), 6.67 (1H, d, J=10 Hz), 6.95–8.50 (4H, m), 9.10 (1H, broad s), 9.67 (2H, broad s).

(49) 7-[2-Methoxyimino-2-(2-aminothiazol-4-yl)acetamido]-3-[2-(1-methyl-2-pyridinio)thiovinyl]-3-cephem-4-carboxylate (syn isomer) (cis isomer).

IR (Nujol): 3400–3100, 1765, 1660, 1610, 1560, 1530 cm$^{-1}$

NMR (DMSO-d$_6$) δ: 3.67 (2H, ABq, J=16 Hz), 3.83 (3H, s), 4.17 (3H, s), 5.12 (1H, d, J=5 Hz), 5.63 (1H, dd, J=5 Hz, 8 Hz), 6.42 (1H, d, J=14 Hz), 6.73 (1H, s), 7.25 (2H, broad s), 7.63 (1H, d, J=14 Hz), 7.9–9.00 (4H, m), 9.57 (1H, d, J=8 Hz).

(50) 7-[(2-Methoxyimino-2-(2-aminothiazol-4-yl)acetamido]-3-[2-(1-methyl-3-pyridinio)thiovinyl-3-cephem-4-carboxylate (syn isomer) (cis isomer).

IR (Nujol): 3300, 1760, 1660, 1600, 1530 cm$^{-1}$

NMR (DMSO-d$_6$) δ: 3.72 (2H, ABq, J=16 Hz), 3.82 (3H, s), 4.33 (3H, s), 5.10 (1H, d, J=5 Hz), 5.65 (1H, dd, J=5 Hz, 8 Hz), 6.38 (1H, d, J=10 Hz), 6.73 (1H, s), 7.22 (1H, d, J=10 Hz), 7.18 (2H, broad s), 7.85–8.90 (3H, m), 9.17 (1H, broad s), 9.50 (1H, d, J=8 Hz).

(51) 7-[2-Methoxyimino-2-(2-tritylaminothiazol-4-yl)acetamido]-3-[2-(1-methyl-3-pyridinio)thiovinyl]-3-cephem-4-carboxylate (syn isomer) (trans isomer).

IR (Nujol): 3300–3400, 1770, 1675, 1620, 1600 cm$^{-1}$

NMR (DMSO-d$_6$) δ: 3.77 (3H, s), 3.80 (2H, m), 4.32 (3H, s), 5.17 (1H, d, J=5 Hz), 5.67 (1H, dd, J=5 Hz, 8 Hz), 6.70 (1H, s), 6.85–7.67 (17H, m), 8.00–9.03 (4H, m), 9.55 (1H, d, J=8 Hz).

(52) 7-[2-Methoxyimino-2-(2-tritylaminothiazol-4-yl)acetamido]-3-[2-(1-methyl-2-pyridinio)thiovinyl]-3-cephem-4-carboxylate (syn isomer) (cis isomer).

IR (Nujol): 3300–3200, 1775, 1680, 1660, 1615, 1600, 1570 cm$^{-1}$

NMR (DMSO-d$_6$) δ: 3.67–3.95 (2H, m), 3.78 (3H, s), 4.20 (3H, s), 5.17 (1H, d, J=5 Hz), 5.70 (1H, dd, J=5 Hz, 8 Hz), 6.70 (1H, s), 6.75 (1H, d, J=10 Hz), 7.00–7.50 (15H, m), 7.67–9.05 (4H, m), 9.52 (1H, d, J=8 Hz).

(53) 7-[2-Methoxyimino-2-(2-tritylaminothiazol-4-yl)acetamido]-3-[2-(1-methyl-3-pyridinio)thiovinyl]-3-cephem-4-carboxylate (syn isomer) (cis isomer).

IR (Nujol): 3350–3250, 1770, 1670, 1620, 1590 cm$^{-1}$

NMR (DMSO-d$_6$) δ: 3.70–4.00 (5H, m), 3.80 (3H, s), 4.30 (3H, s), 5.20 (1H, d, J=5 Hz), 5.70 (1H, dd, J=5 Hz, 8 Hz), 6.70 (1H, s), 6.73 (1H, d, J=11 Hz), 7.00 (1H, d, J=11 Hz), 7.15–7.50 (15H, m), 8.00–9.10 (5H, m), 9.50 (1H, d, J=8 Hz).

(54) 7-[2-(3-Carboxypropoxyimino)-2-(5-amino-1,2,4-thiodiazol-3-yl)acetamido]-3-[2-(1-methyl-3-pyridinio)-thiovinyl]-3-cephem-4-carboxylate (syn isomer).

IR (Nujol): 3300, 1765, 1665, 1600, 1530 cm$^{-1}$

NMR (DMSO-d$_6$) δ: 1.6–2.7 (4H, m), 3.75 (2H, broad s), 4.0–4.4 (2H, m), 4.40 (3H, s), 5.10 (1H, d, J=4 Hz), 5.72 (1H, dd, J=4, 8 Hz), 6.75 (1H, d, J=16 Hz), 7.44 (1H, d, J=16 Hz), 7.7–9.1 (4H, m), 9.60 (1H, d, J=8 Hz).

(55) 7-[2-Ethoxyimino-2-(5-amino-1,2,4-thiadiazol-3-yl)acetamido]-3-[2-(1-methyl-2-pyridinio)thiovinyl]-3-cephem-4-carboxylate (syn isomer) (cis isomer).

IR (Nujol): 3300, 1765, 1670, 1610, 1560 cm$^{-1}$

NMR (DMSO-d$_6$) δ: 1.27 (3H, t, J=5 Hz), 3.65–4.35 (4H, m), 5.10 (1H, d, J=5 Hz), 5.68 (1H, dd, J=5 Hz, 8 Hz), 6.42 (1H, d, J=14 Hz), 7.67 (1H, d, J=14 Hz), 6.95–9.00 (6H, m), 9.50 (1H, d, J=8 Hz).

(56) 7-[2-Ethoxyimino-2-(5-phosphonoamino-1,2,4-thiadiazol-3-yl)acetamido]-3-[2-(1-methyl-3-pyridinio)-thiovinyl]-3-cephem-4-carboxylate (syn isomer) (trans isomer).

IR (Nujol): 3200–3400 (broad), 1760, 1672, 1520 cm$^{-1}$

NMR (NaHCO$_3$-D$_2$O) δ: 1.33 (3H, t, J=7 Hz), 3.77 (2H, broad s), 4.35 (3H, s), 4.33 (2H, q, J=7 Hz), 5.30 (1H, d, J=5 Hz), 5.82 (1H, d, J=5 Hz), 6.60 (1H, d, J=15 Hz), 7.17 (1H, d, J=15 Hz), 7.85–8.80 (4H, m).

(57) 7-[2-Ethoxyimino-2-(5-phosphonoamino-1,2,4-thiadiazol-3-yl)acetamido]-3-[2-(1-methyl-2-pyridinio)-thiovinyl]-3-cephem-4-carboxylate (syn isomer) (trans isomer).

IR (Nujol): 3200, 1768, 1673, 1610, 1560, 1508, 1269, 1230 cm$^{-1}$

NMR (NaHCO$_3$-D$_2$O) δ: 1.33 (3H, t, J=7 Hz), 3.83 (2H, broad s), 4.23 (3H, s), 4.38 (2H, q, J=7 Hz), 5.30 (1H, d, J=5 Hz), 5.80 (1H, d, J=5 Hz), 6.60 (1H, d, J=14 Hz), 7.38 (1H, d, J=14 Hz), 7.4–8.8 (4H, m).

(58) 7-[2-Allyloxyimino-2-(2-aminothiazol-4-yl)acetamido]-3-{2-[1-(3-aminopropyl)-3-pyridinio)]thiovinyl}-3-cephem-4-carboxylate hydrochloride (syn isomer) (trans isomer).

IR (Nujol): 3350, 1770, 1665, 1618 cm$^{-1}$.

(59) 7-[2-Allyloxyimino-2-(2-aminothiazol-4-yl)acetamido]-3-{2-[1-(3-N,N-dimethylaminopropyl)-3-pyridinio]thiovinyl}-3-cephem-4-carboxylate hydrochloride (syn isomer) (cis isomer).

IR (Nujol): 3300, 1775, 1660, 1610 cm$^{-1}$.

EXAMPLE 23

The following compounds were obtained according to similar manners to those of Examples 1, 4, 6, 8, 14 and 15.

(1) 7-[2-Ethoxyimino-2-(2-aminothiazol-4-yl)acetamido]-3-{2-[1-(3-N,N-dimethylaminopropyl)-3-pyridinio]-thiovinyl}-3-cephem-4-carboxylate hydrochloride (syn isomer) (trans isomer).

IR (Nujol): 3250, 1770, 1670, 1630, 1550 cm$^{-1}$

NMR (D$_2$O) δ: 1.33 (3H, t, J=7 Hz), 2.51 (2H, m), 2.92 (6H, s), 3.32 (2H, m), 3.79 (2H, broad s), 4.34 (2H, q, J=7 Hz), 4.79 (2H, m), 5.26 (1H, d, J=5 Hz), 5.79 (1H, d, J=5 Hz), 6.93 (2H, ABq, J=16 Hz), 7.08 (1H, s), 7.97 (1H, dd, J=6 Hz, 8 Hz), 8.48 (1H, d, J=8 Hz), 6.87 (1H, d, J=6 Hz), 8.80 (1H, broad s).

(2) 7-[2-Ethoxyimino-2-(2-aminothiazol-4-yl)acetamido]-3-{2-[1-(3-aminopropyl)-3-pyridinio]thiovinyl}-3-cephem-4-carboxylate hydrochloride (syn isomer) (trans isomer).

IR (Nujol): 3250, 1770, 1670, 1630, 1550 cm$^{-1}$

NMR (D$_2$O) δ: 1.34 (3H, t, J=7 Hz), 2.42 (2H, m), 3.17 (2H, m), 3.81 (2H, broad s), 4.32 (2H, q, J=7 Hz), 4.79 (2H, m), 5.28 (1H, d, J=5 Hz), 5.75 (1H, d, J=5 Hz), 7.03 (2H, ABq, J=16 Hz), 7.08 (1H, s), 7.97 (1H, dd, J=6 Hz, 8 Hz), 8.48 (1H, d, J=8 Hz), 8.68 (1H, d, J=6 Hz), 8.85 (1H, broad s).

(3) 7-[2-Methoxyimino-2-(5-amino-1,2,4-thiadiazol-3-yl)-acetamido]-3-{2-[1-(3-dimethylaminopropyl)-3-pyridinio thiovinyl}-3-cephem-4-carboxylate hydrochloride (syn isomer) (trans isomer). m.p. 140°–145° C. (dec.).

IR (Nujol): 3350, 2650, 1770, 1670, 1610, 1550, 1525, 1490 cm$^{-1}$

NMR (D$_2$O) δ: 2.30–2.72 (2H, m), 2.92 (6H, s), 3.15–3.50 (2H, m), 3.77 (2H, broad s), 4.07 (3H, s), 4.50–4.85 (2H, m), 5.27 (1H, d, J=5 Hz), 5.82 (1H, d, J=5 Hz), 6.80 (1H, d, J=16 Hz), 7.20 (1H, d, J=16 Hz), 7.90–8.17 (1H, m), 8.38–8.58 (1H, m), 8.67–8.80 (1H, m), 8.88 (1H, s).

EXAMPLE 24

The following compound was obtained according to a similar manner to that of Example 20.

7-[2-Allylox-imino-2-(5-amino-1,2,4-thiadiazol-3-yl)acetamido]-3-{2-[1-(3-formimidoylaminopropyl)-3-pyridinio]thiovinyl}-3-cephem-4-carboxylate (syn isomer) (trans isomer).

IR (Nujol): 3250, 1760, 1710, 1660, 1590, 1530 cm$^{-1}$
NMR (D$_2$O) δ: 2.13–2.68 (2H, m), 3.48 (2H, t, J=7 Hz), 3.73 (2H, m), 5.26 (1H, d, J=5 Hz), 5.79 (1H, d, J=5 Hz), 5.15–6.08 (3H, m), 6.62 (1H, d, J=14 Hz), 7.08 (1H, d, J=14 Hz), 7.83 (1H, s), 7.95 (1H, m), 8.43 (1H, d, J=8 Hz), 8.69 (1H, d, J=6 Hz), 8.79 (1H, s).

EXAMPLE 25

The following compound was obtained according to similar manners to those of Examples 1,4,6,8,14 and 15.

7-[2-Propargyloxyimino-2-(2-aminothiazol-4-yl)acetamido]-3-{2-[1-(3-aminopropyl)-3-pyridinio]thiovinyl}-3-cephem-4-carboxylate hydrochloride (syn isomer) (trans isomer).

IR (Nujol): 1760, 1650, 1580, 1520 cm$^{-1}$.

What we claim is:

1. A cephem compound of the formula:

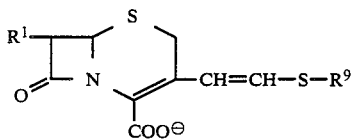

wherein R$^1$ is alkanoylamino;
  amino thiazolyl(lower)alkanoylamino having a lower alkoxyimino;
  aminothiazolyl(lower)alkanoylamino having a lower alkenyloxyimino;
  aminothiazolyl(lower)alkanoylamino having a lower alkynyloxyimino;
  aminothiazolyl(lower)alkanoylamino having a carboxy-(lower)alkoxyimino;
  aminothiazolyl(lower)alkanoylamino having a lower alkoxycarbonyl(lower)alkoxyimino;
  thiazolyl(lower)alkanoylamino having a amino- ar(-lower)alkoxycarbonyl(lower)alkoxyimino;
  aminothiazolyl(lower)alkanoylamino having a hydroxy-(lower)alkoxyimino;
  aminothiazolyl(lower)alkanoylamino having a carboxy-(lower)alkenyloxyimino;
  aminothiazolyl(lower)alkanoylamino having an ar(-lower)alkoxycarbonyl(lower)alkenyloxyimino;
  aminothiazolyl(lower)alkanoylamino having a pyridyl(lower)alkoxyimino;
  aminothiazolyl(lower)alkanoylamino having a 1-(lower)alkyl pyridinio(lower)alkoxyimino;
  lower alkanoylaminothiazolyl(lower)alkanoylamino having a lower alkoxyimino;
  ar(lower)alkylaminothiazolyl(lower)alkanoylamino having a lower alkoxyimino;
  ar(lower)alkylaminothiazolyl(lower)alkanoylamino having a lower alkynyloxyimino;
  lower alkanoylaminothiazolyl(lower)alkanoylamino having a lower alkoxycarbonyl(lower)alkoxyimino;
  ar(lower)alkylaminothiazolyl(lower)alkanoylamino having an ar(lower)alkoxycarbonyl(lower)alkoxyimino;
  ar(lower)alkylaminothiazolyl(lower)alkanoylamino having an ar(lower)alkoxycarbonyl(lower)alkenyloxyimino;
  lower alkanoylaminothiazolyl(lower)alkanoylamino having a pyridyl(lower)alkoxyimino;
  aminothiadiazolyl(lower)alkanoylamino having a lower alkoxyimino;
  aminothiadiazolyl(lower)alkanoylamino having a lower alkenyloxyimino;
  aminothiadiazolyl(lower)alkanoylamino having a lower alkynyloxyimino;
  aminothiadiazolyl(lower)alkanoylamino having a hydroxy(lower)alkoxyimino;
  aminothiadiazolyl(lower)alkanoylamino having a carboxy(lower)alkoxyimino;
  phosphonoaminothiadiazolyl(lower)alkanoylamino having a lower alkoxyimino;
  thiazolyl(lower)alkanoylamino having a carboxy(lower)alkoxyimino;
  thiadiazolyl(lower)alkanoylamino having a lower alkoxyimino;
  isothiazolylthio(lower)alkanoylamino substituted with hydrogen and carboxy;
  aminothiazolyl hydroxy substituted(lower)alkanoyl amino;
  dihydrooxathiinyl(lower)alkanoylamino having a lower alkoxyimino;
  hydroxy ar(lower)alkanoylamino having a lower alkoxyimino;
  aminopyrimidinyl(lower)alkanoylamino having a lower alkenyloxyimino;
  aminopyridyl(lower)alkanoylamino having a lower alkoxyimino;
  lower alkanoylaminopyridyl(lower)alkanoylamino having a lower alkoxyimino;
  aminothiazolyl(lower)alkanoylamino having a carboxycyclo(lower)alkoxyimino; or
  ar(lower)alkylaminothiazolyl(lower)alkanoylamino having a lower alkoxycarbonylcyclo(lower)alkoxyimino;
and
R$^9$ is a group of the formula:

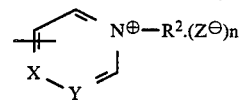

wherein R$^2$ is lower alkyl, amino(lower)alkyl, hydroxy(lower)alkyl, carboxy(lower)alkyl, di(lower)alkylamino(lower)alkyl, morpholino(lower)alkyl, lower alkylpiperazinyl(lower)alkyl, lower alkylpiperazinylcarbonyl(lower)alkyl or formimidoylamino(lower)alkyl,
X is CH or N,
Z is alkanoyloxy, azido or halogen,
Y is CH or N and n is 0; or
Y is N⊕—R$^2$ wherein R$^2$ is as defined above and n is 1, or a group of the formula:

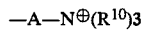

wherein R[10] is lower alkyl and
A is lower alkylene, and pharmaceutically acceptable salts thereof.

2. Syn isomer of a compound of claim 1, wherein R[1] is 2-methoxyimino-2-(2-aminothiazol-4-yl)acetamido, 2-ethoxyimino-2-(2-aminothiazol-4-yl)acetamido, 2-carboxymethoxyimino-2-(2-aminothiazol-4-yl)acetamido, 2-allyloxyimino-2-(2-aminothiazol-4-yl)acetamido, 2-(2-propynyloxyimino)-2-(2-aminothiazol-4-yl)acetamido, 2-methoxyimino-2-(5-amino-1,2,4-thiadiazol-3-yl)acetamido, 2-ethoxyimino-2-(5-amino-1,2,4-thiadiazol-3-yl)acetamido, or 2-allyloxyimino-2-(5-amino-1,2,4-thiadiazol-3-yl)acetamido, and
R[9] is a group of the formula:

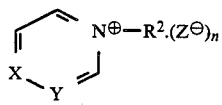

wherein
R[2] is methyl, ethyl, 3-aminopropyl, 2-aminoethyl, 3-N,N-dimethylaminopropyl or 2-N,N-dimethylaminoethyl, and
Y is CH or N and n is 0.

3. A compound of claim 1, which is selected from the group consisting of:
trifluoroacetic acid salt of 7-amino-3-[2-(1-methyl-3-pyridinio)thiovinyl]-3-cephem-4-carboxylate (cis isomer or trans isomer) or its hydriodide, and
trifluoroacetic acid salt of 7-amino-3-[2-(1-methyl-2-pyridinio)thiovinyl]-3-cephem-4-carboxylate cis isomer, trans isomer) or its hydriodide.

4. A compound of claim 3, which is selected from the group consisting of:
7-[2-ethoxyimino-2-(5-amino-1,2,4-thiadiazol-3-yl)acetamido]-3-[2-(1-methyl-3-pyridinio)thiovinyl]-3-cephem-4-carboxylate (syn isomer) (cis isomer or trans isomer),
7-[2-allyloxyimino-2-(5-amino-1,2,4-thiadiazol-3-yl)acetamido]-3-[2-(1-methyl-3-pyridinio)thiovinyl]-3-cephem-4-carboxylate (syn isomer) (cis isomer or trans isomer),
7-[2-allyloxyimino-2-(5-amino-1,2,4-thiadiazol-3-yl)acetamido]-3-{2-[1-(3-aminopropyl)-3-pyridinio]thiovinyl}-3-cephem-4-carboxylate (syn isomer) (cis isomer or trans isomer) or its hydrochloride,
7-[2-allyloxyimino-2-(5-amino-1,2,4-thiadiazol-3-yl)acetamido]-3-{2-[1-(3-N,N-dimethylaminopropyl)-3-pyridinio]thiovinyl}-3-cephem-4-carboxylate (syn isomer) (cis isomer or trans isomer) or its hydrochloride,
7-[2-ethoxyimino-2-(5-amino-1,2,4-thiadiazol-3-yl)acetamido]-3-{2-[1-(3-aminopropyl)-3-pyridinio]thiovinyl}-3-cephem-4-carboxylate (syn isomer) (cis isomer or trans isomer) or its hydrochloride,
7-[2-ethoxyimino-2-(5-amino-1,2,4-thiadiazol-3-yl)acetamido]-3-{2-[1-(3-N,N-dimethylaminopropyl)-3-pyridinio]thiovinyl}-3-cephem-4-carboxylate (syn isomer) (cis isomer or trans isomer) or its hydrochloride,
7-[2-allyloxyimino-2-(2-aminothiazol-4-yl)acetamido]-3-{2-[1-(3-aminopropyl)-3-pyridinio]thiovinyl}-3-cephem-4-carboxylate (syn isomer) (cis isomer or trans isomer) or its hydrochloride, and
7-[2-allyloxyimino-2-(2-aminothiazol-4-yl)acetamido]-3-{2-[1-(3-N,N-dimethylaminopropyl)-3-pyridinio]thiovinyl}-3-cephem-4-carboxylate (syn isomer) (cis isomer or trans isomer) or its hydrochloride.

5. A pharmaceutical antimicrobial composition comprising an effective amount of a compound of claim 1 or pharmaceutically acceptable salt thereof in association with a pharmaceutically acceptable, substantially non-toxic carrier or excipient.

6. A compound of the formula:

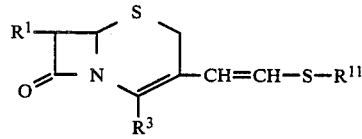

wherein R[1] is alkanoylamino;
amino thiazolyl(lower)alkanoylamino having a lower alkoxyimino;
aminothiazolyl(lower)alkanoylamino having a lower alkenyloxyimino;
aminothiazolyl(lower)alkanoylamino having a lower alkynyloxyimino;
aminothiazolyl(lower)alkanoylamino having a carboxy-(lower)alkoxyimino;
aminothiazolyl(lower)alkanoylamino having a lower alkoxycarbonyl(lower)alkoxyimino;
thiazolyl(lower)alkanoylamino having a amino-ar-(lower)alkoxycarbonyl(lower)alkoxyimino;
aminothiazolyl(lower)alkanoylamino having a hydroxy-(lower)alkoxyimino;
aminothiazolyl(lower)alkanoylamino having a carboxy-(lower)alkenyloxyimino;
aminothiazolyl(lower)alkanoylamino having an ar(-lower)alkoxycarbonyl(lower)alkenyloxyimino;
aminothiazolyl(lower)alkanoylamino having a pyridyl(lower)alkoxyimino;
aminothiazolyl(lower)alkanoylamino having a 1-(lower)alkyl pyridinio(lower)alkoxyimino;
lower alkanoylaminothiazolyl(lower)alkanoylamino having a lower alkoxyimino;
ar(lower)alkylaminothiazolyl(lower)alkanoylamino having a lower alkoxyimino;
ar(lower)alkylaminothiazolyl(lower)alkanoylamino having a lower alkynyloxyimino;
lower alkanoylaminothiazolyl(lower)alkanoylamino having a lower alkoxycarbonyl(lower)alkoxyimino;
ar(lower)alkylaminothiazolyl(lower)alkanoylamino having an ar(lower)alkoxycarbonyl(lower)alkoxyimino;
ar(lower)alkylaminothiazolyl(lower)alkanoylamino having an ar(lower)alkoxycarbonyl(lower)alkenyloxyimino;
lower alkanoylaminothiazolyl(lower)alkanoylamino having a pyridyl(lower)alkoxyimino;
aminothiadiazolyl(lower)alkanoylamino having a lower alkoxyimino;
aminothiadiazolyl(lower)alkanoylamino having a lower alkenyloxyimino;
aminothiadiazolyl(lower)alkanoylamino having a lower alkynyloxyimino;

aminothiadiazolyl(lower)alkanoylamino having a hydroxy(lower)alkoxyimino;
aminothiadiazolyl(lower)alkanoylamino having a carboxy(lower)alkoxyimino;
phosphonoaminothiadiazolyl(lower)alkanoylamino having a lower alkoxyimino;
thiazolyl(lower)alkanoylamino having a carboxy(lower)alkoxyimino;
thiadiazolyl(lower)alkanoylamino having a lower alkoxyimino;
isothiazolylthio(lower)alkanoylamino substituted with hydrogen and carboxy;
aminothiazolyl hydroxy substituted(lower)alkanoyl amino;
dihydrooxathiinyl(lower)alkanoylamino having a lower alkoxyimino;
hydroxy ar(lower)alkanoylamino having a lower alkoxyimino;
aminopyrimidinyl(lower)alkanoylamino having a lower alkenyloxyimino;
aminopyridyl(lower)alkanoylamino having a lower alkoxyimino;
lower alkanoylaminopyridyl(lower)alkanoylamino having a lower alkoxyimino;
aminothiazolyl(lower)alkanoylamino having a carboxycyclo(lower)alkoxyimino; or
ar(lower)alkylaminothiazolyl(lower)alkanoylamino having a lower alkoxycarbonylcyclo(lower)alkoxyimino;

$R^3$ is a protected carboxy; and
$R^{11}$ is a group of the formula:

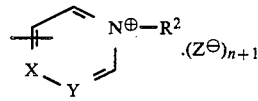

wherein $R^2$ is lower alkyl, amino(lower)alkyl, hydroxy(lower)alkyl, carboxy(lower)alkyl, di(lower)alkylamino(lower)alkyl, morpholino(lower)alkyl, lower alkylpiperazinyl(lower)alkyl, lower alkylpiperazinylcarbonyl(lower)alkyl or formimidoylamino(lower)alkyl,
X is CH or N,
Z is alkanoyloxy, azido or halogen,
Y is CH or N and n is 0; or
Y is $N^{\oplus}$—$R^2$ wherein $R^2$ is as defined above and n is 1, or a group of the formula:

wherein $R^{10}$ is lower alkyl and A is lower alkylene, and pharmaceutically acceptable salts thereof.

* * * * *